US007117108B2

(12) United States Patent
Rapp et al.

(10) Patent No.: US 7,117,108 B2
(45) Date of Patent: Oct. 3, 2006

(54) SYSTEM AND METHOD FOR CATEGORICAL ANALYSIS OF TIME DEPENDENT DYNAMIC PROCESSES

(76) Inventors: Paul Ernest Rapp, 22 Avon Rd., Narberth, PA (US) 19072; Christopher Joseph Cellucci, 2014 St. Andrew's Dr., Berwyn, PA (US) 19312; Tanya Schmah, 2/13 Lucinda Road, Marsfield, N.S.W. (AU) 2122

( * ) Notice: Subject to any disclaimer, the term of this patent is extended or adjusted under 35 U.S.C. 154(b) by 0 days.

(21) Appl. No.: 10/854,700

(22) Filed: May 26, 2004

(65) Prior Publication Data

US 2004/0243328 A1  Dec. 2, 2004

Related U.S. Application Data

(60) Provisional application No. 60/473,788, filed on May 28, 2003.

(51) Int. Cl.
    G06F 19/00 (2006.01)
(52) U.S. Cl. .................... 702/71; 600/544; 600/509; 702/179
(58) Field of Classification Search .................. None
    See application file for complete search history.

(56) References Cited

U.S. PATENT DOCUMENTS

| | | | | |
|---|---|---|---|---|
| 6,278,961 B1 * | 8/2001 | Kadtke et al. | ............... | 702/189 |
| 6,484,132 B1 * | 11/2002 | Hively et al. | ............... | 702/190 |
| 6,564,176 B1 * | 5/2003 | Kadtke et al. | ............... | 702/189 |
| 6,658,287 B1 * | 12/2003 | Litt et al. | ................... | 600/544 |
| 6,678,548 B1 * | 1/2004 | Echauz et al. | ............... | 600/544 |
| 6,731,975 B1 * | 5/2004 | Viertio-Oja et al. | ........ | 600/544 |
| 6,775,645 B1 * | 8/2004 | Daw et al. | ................... | 702/188 |
| 6,901,351 B1 * | 5/2005 | Daw et al. | ................... | 702/188 |
| 6,920,349 B1 * | 7/2005 | Schreck | ....................... | 600/512 |
| 6,925,324 B1 * | 8/2005 | Shusterman | ................ | 600/509 |
| 6,954,700 B1 * | 10/2005 | Higashida et al. | ............ | 702/19 |
| 2003/0055343 A1 * | 3/2003 | Korhonen | .................... | 600/481 |
| 2003/0167019 A1 * | 9/2003 | Viertio-Oja et al. | ........ | 600/544 |
| 2003/0181821 A1 * | 9/2003 | Greenwald et al. | .......... | 600/544 |
| 2004/0002661 A1 * | 1/2004 | Schreck | ....................... | 600/509 |
| 2004/0068199 A1 * | 4/2004 | Echauz et al. | .............. | 600/544 |
| 2004/0082876 A1 * | 4/2004 | Viertio-Oja et al. | ........ | 600/544 |
| 2004/0230105 A1 * | 11/2004 | Geva et al. | .................. | 600/301 |
| 2005/0182338 A1 * | 8/2005 | Huiku | ......................... | 600/544 |

OTHER PUBLICATIONS

P.E. Rapp et al., "Nonlinear Signal Classification", International Journal of Bifurcation and Chaos, vol. 12, No. 6, Jun. 2002.

Neumeister et al., "Dynamical Analysis Reveals Individuality of Locomotion in Goldfish", The Journal of Experimental Biology 207, Nov. 24, 2003, pp. 697-708.

Watanabe et al., "The Algorithmic Complexity of Multichannel EEGs is Sensitive to Changes in Behavior", Psychophysiology, 40, 2003, pp. 77-97.

Cellucci et al., "Quantitative Determination of Abrupt Changes in Dynamical Systems: Illustration Via Identification of Seizure Termination in Generalized Tonic-Clonic Seizure EEG Data", International Journal of Bifurcation and Chaos, vol. 13, No. 9, 2003.

* cited by examiner

*Primary Examiner*—Patrick J. Assouad
(74) *Attorney, Agent, or Firm*—Volpe and Koenig, P.C.

(57) ABSTRACT

A system and method for performing a categorical analysis on one or more time dependent dynamic processes is provided. A reference library of data pertaining to multiple characteristics of time series reflective of the dynamic process is created and used to define selected categories for performing the categorical analysis.

32 Claims, 18 Drawing Sheets

|       | VDP | Lor      | Rös      | Hénon    | Uni      | F(Uni)   | Nor      | F(Nor)   | Co              |
|-------|-----|----------|----------|----------|----------|----------|----------|----------|-----------------|
| VDP   |     | $<10^{-8}$ | $<10^{-8}$ | $<10^{-8}$ | $<10^{-8}$ | $<10^{-8}$ | $<10^{-8}$ | $<10^{-8}$ | $<10^{-8}$      |
| Lor   |     |          | $<10^{-8}$ | $<10^{-8}$ | $<10^{-8}$ | $<10^{-8}$ | $<10^{-8}$ | $<10^{-8}$ | $<10^{-8}$      |
| Rös   |     |          |          | $<10^{-8}$ | $<10^{-8}$ | $<10^{-8}$ | $<10^{-8}$ | $<10^{-8}$ | $<10^{-8}$      |
| Hénon |     |          |          |          | $<10^{-8}$ | $<10^{-8}$ | $<10^{-8}$ | $<10^{-8}$ | $<10^{-8}$      |
| Uni   |     |          |          |          |          | $<10^{-8}$ | $<10^{-8}$ | $<10^{-8}$ | $<10^{-8}$      |
| F(Uni)|     |          |          |          |          |          | $<10^{-8}$ | $<10^{-8}$ | $<10^{-8}$      |
| Nor   |     |          |          |          |          |          |          | $<10^{-8}$ | $0.6\times10^{-5}$ |
| F(Nor)|     |          |          |          |          |          |          |          | $<10^{-8}$      |
| Co    |     |          |          |          |          |          |          |          |                 |

FIGURE 5a

|       | VDP | Lor      | Rös      | Hénon    | Uni      | F(Uni)   | Nor      | F(Nor)   | Co              |
|-------|-----|----------|----------|----------|----------|----------|----------|----------|-----------------|
| VDP   |     | $<10^{-8}$ | $<10^{-8}$ | $<10^{-8}$ | $<10^{-8}$ | $<10^{-8}$ | $<10^{-8}$ | $<10^{-8}$ | $<10^{-8}$      |
| Lor   |     |          | $<10^{-8}$ | $<10^{-8}$ | $<10^{-8}$ | $<10^{-8}$ | $<10^{-8}$ | $<10^{-8}$ | $<10^{-8}$      |
| Rös   |     |          |          | $<10^{-8}$ | $<10^{-8}$ | $<10^{-8}$ | $<10^{-8}$ | $<10^{-8}$ | $<10^{-8}$      |
| Hénon |     |          |          |          | $<10^{-8}$ | $<10^{-8}$ | $<10^{-8}$ | $<10^{-8}$ | $<10^{-8}$      |
| Uni   |     |          |          |          |          | $<10^{-8}$ | $<10^{-8}$ | $<10^{-8}$ | $<10^{-8}$      |
| F(Uni)|     |          |          |          |          |          | $<10^{-8}$ | $<10^{-8}$ | $<10^{-8}$      |
| Nor   |     |          |          |          |          |          |          | $<10^{-8}$ | $0.6\times10^{-2}$ |
| F(Nor)|     |          |          |          |          |          |          |          | $<10^{-8}$      |
| Co    |     |          |          |          |          |          |          |          |                 |

FIGURE 5b

|       | VDP | Lor | Rös | Hénon | Uni | F(Uni) | Nor | F(Nor) | Co |
|-------|-----|-----|-----|-------|-----|--------|-----|--------|----|
| VDP   | 10  |     |     |       |     |        |     |        |    |
| Lor   |     | 10  |     |       |     |        |     |        |    |
| Rös   |     |     | 10  |       |     |        |     |        |    |
| Hénon |     |     |     | 10    |     |        |     |        |    |
| Uni   |     |     |     |       | 10  |        |     |        |    |
| F(Uni)|     |     |     |       |     | 10     |     |        |    |
| Nor   |     |     |     |       |     |        | 10  |        |    |
| F(Nor)|     |     |     |       |     |        |     | 10     |    |
| Co    |     |     |     |       |     |        |     |        | 10 |

FIGURE 5c

|        | VDP | Lor | Rös | Hénon | Uni | F(Uni) | Nor | F(Nor) | Co |
|--------|-----|-----|-----|-------|-----|--------|-----|--------|----|
| VDP    | 10  |     |     |       |     |        |     |        |    |
| Lor    |     | 10  |     |       |     |        |     |        |    |
| Rös    |     |     | 10  |       |     |        |     |        |    |
| Hénon  |     |     |     | 10    |     |        |     |        |    |
| Uni    |     |     |     |       | 10  |        |     |        |    |
| F(Uni) |     |     |     |       |     | 10     |     |        |    |
| Nor    |     |     |     |       |     |        | 10  |        |    |
| F(Nor) |     |     |     |       |     |        |     | 10     |    |
| Co     |     |     |     |       |     |        |     |        | 10 |

FIGURE 5d

|        | VDP | Lor | Rös | Hénon | Uni | F(Uni) | Nor | F(Nor) | Co |
|--------|-----|-----|-----|-------|-----|--------|-----|--------|----|
| VDP    |     | $0.5 \times 10^{-7}$ | $< 10^{-8}$ | $< 10^{-8}$ | $< 10^{-8}$ | $< 10^{-8}$ | $< 10^{-8}$ | $< 10^{-7}$ | $< 10^{-8}$ |
| Lor    |     |     | $< 10^{-8}$ | $< 10^{-8}$ | $< 10^{-8}$ | $< 10^{-8}$ | $< 10^{-8}$ | $0.3 \times 10^{-2}$ | $< 10^{-8}$ |
| Rös    |     |     |     | $< 10^{-8}$ | $< 10^{-8}$ | $< 10^{-8}$ | $< 10^{-8}$ | $< 10^{-8}$ | $< 10^{-8}$ |
| Hénon  |     |     |     |       | $0.6 \times 10^{-7}$ | $< 10^{-8}$ | $< 10^{-7}$ | $< 10^{-8}$ | $0.3 \times 10^{-7}$ |
| Uni    |     |     |     |       |     | $< 10^{-8}$ | $0.2 \times 10^{-5}$ | $< 10^{-8}$ | $< 10^{-8}$ |
| F(Uni) |     |     |     |       |     |        | $< 10^{-8}$ | $0.6 \times 10^{-7}$ | $< 10^{-8}$ |
| Nor    |     |     |     |       |     |        |     | $< 10^{-8}$ | $0.5 \times 10^{-4}$ |
| F(Nor) |     |     |     |       |     |        |     |        | $< 10^{-8}$ |
| Co     |     |     |     |       |     |        |     |        |    |

FIGURE 5e

|        | VDP | Lor | Rös | Hénon | Uni | F(Uni) | Nor | F(Nor) | Co |
|--------|-----|-----|-----|-------|-----|--------|-----|--------|----|
| VDP    |     | $0.9 \times 10^{-4}$ | $< 10^{-8}$ | $< 10^{-8}$ | $< 10^{-8}$ | $0.5 \times 10^{-5}$ | $< 10^{-8}$ | 0.0002 | $< 10^{-8}$ |
| Lor    |     |     | $< 10^{-8}$ | $< 10^{-8}$ | $< 10^{-8}$ | $0.7 \times 10^{-5}$ | $< 10^{-8}$ | 0.0742 | $< 10^{-8}$ |
| Rös    |     |     |     | $< 10^{-8}$ | $< 10^{-8}$ | $< 10^{-8}$ | $< 10^{-8}$ | $< 10^{-8}$ | $< 10^{-8}$ |
| Hénon  |     |     |     |       | $10^{-4}$ | $< 10^{-8}$ | 0.0002 | $< 10^{-8}$ | $0.6 \times 10^{-4}$ |
| Uni    |     |     |     |       |     | $< 10^{-8}$ | 0.0030 | $< 10^{-8}$ | $10^{-6}$ |
| F(Uni) |     |     |     |       |     |        | $< 10^{-8}$ | $10^{-4}$ | $< 10^{-8}$ |
| Nor    |     |     |     |       |     |        |     | $< 10^{-8}$ | 0.0166 |
| F(Nor) |     |     |     |       |     |        |     |        | $< 10^{-8}$ |
| Co     |     |     |     |       |     |        |     |        |    |

FIGURE 5f

|       | VDP | Lor | Rös | Hénon | Uni | F(Uni) | Nor | F(Nor) | Co |
|-------|-----|-----|-----|-------|-----|--------|-----|--------|-----|
| VDP   | 10  |     |     |       |     |        |     |        |     |
| Lor   |     | 10  |     |       |     |        |     |        |     |
| Rös   |     |     | 10  |       |     |        |     |        |     |
| Hénon |     |     |     | 10    |     |        |     |        |     |
| Uni   |     |     |     |       | 10  |        |     |        |     |
| F(Uni)|     |     |     |       |     | 10     |     |        |     |
| Nor   |     |     |     |       |     |        | 9   |        | 1  |
| F(Nor)|     | 1   |     |       |     |        |     | 9      |     |
| Co    |     |     |     |       |     |        |     |        | 10 |

FIGURE 5g

|       | VDP | Lor | Rös | Hénon | Uni | F(Uni) | Nor | F(Nor) | Co |
|-------|-----|-----|-----|-------|-----|--------|-----|--------|-----|
| VDP   | 10  |     |     |       |     |        |     |        |     |
| Lor   |     | 10  |     |       |     |        |     |        |     |
| Rös   |     |     | 10  |       |     |        |     |        |     |
| Hénon |     |     |     | 10    |     |        |     |        |     |
| Uni   |     |     |     |       | 10  |        |     |        |     |
| F(Uni)|     |     |     |       |     | 10     |     |        |     |
| Nor   |     |     |     |       |     |        | 10  |        |     |
| F(Nor)|     | 1   |     |       |     |        |     | 9      |     |
| Co    |     |     |     |       |     |        |     |        | 10 |

FIGURE 5h

|       | VDP | Lor | Rös | Hénon | Uni | F(Uni) | Nor | F(Nor) | Co |
|-------|-----|-----|-----|-------|-----|--------|-----|--------|-----|
| VDP   |     | $0.5 \times 10^{-5}$ | $< 10^{-8}$ | $< 10^{-8}$ | $< 10^{-8}$ | 0.0032 | $< 10^{-8}$ | $0.4 \times 10^{-5}$ | $< 10^{-8}$ |
| Lor   |     |     | $< 10^{-8}$ | $< 10^{-8}$ | $< 10^{-8}$ | 0.0016 | $< 10^{-8}$ | 0.0007 | $< 10^{-8}$ |
| Rös   |     |     |     | $< 10^{-8}$ | $< 10^{-8}$ | $< 10^{-8}$ | $< 10^{-8}$ | $< 10^{-8}$ | $< 10^{-8}$ |
| Hénon |     |     |     |     | $10^{-6}$ | $< 10^{-8}$ | 0.0007 | $< 10^{-8}$ | $0.2 \times 10^{-4}$ |
| Uni   |     |     |     |     |     | $< 10^{-8}$ | 0.0006 | $< 10^{-8}$ | $0.8 \times 10^{-6}$ |
| F(Uni)|     |     |     |     |     |     | $< 10^{-8}$ | 0.0154 | $< 10^{-8}$ |
| Nor   |     |     |     |     |     |     |     | $< 10^{-8}$ | 0.0003 |
| F(Nor)|     |     |     |     |     |     |     |     | $< 10^{-8}$ |
| Co    |     |     |     |     |     |     |     |     |     |

FIGURE 5i

|  | VDP | Lor | Rös | Hénon | Uni | F(Uni) | Nor | F(Nor) | Co |
|---|---|---|---|---|---|---|---|---|---|
| VDP |  | 0.0049 | $< 10^{-8}$ | $< 10^{-8}$ | $< 10^{-8}$ | 0.0796 | $< 10^{-8}$ | 0.0043 | $< 10^{-8}$ |
| Lor |  |  | $< 10^{-8}$ | $< 10^{-8}$ | $< 10^{-8}$ | 0.0641 | $< 10^{-6}$ | 0.0494 | $< 10^{-8}$ |
| Rös |  |  |  | $< 10^{-5}$ | $< 10^{-8}$ | $< 10^{-8}$ | $< 10^{-8}$ | $< 10^{-8}$ | $< 10^{-8}$ |
| Hénon |  |  |  |  | 0.0019 | $< 10^{-8}$ | 0.0485 | $< 10^{-8}$ | 0.0110 |
| Uni |  |  |  |  |  | $< 10^{-8}$ | 0.0459 | $< 10^{-8}$ | 0.0013 |
| F(Uni) |  |  |  |  |  |  | $< 10^{-8}$ | 0.1229 | $3 \times 10^{-6}$ |
| Nor |  |  |  |  |  |  |  | $< 10^{-8}$ | 0.0339 |
| F(Nor) |  |  |  |  |  |  |  |  | $0.9 \times 10^{-5}$ |
| Co |  |  |  |  |  |  |  |  |  |

FIGURE 5j

|  | VDP | Lor | Rös | Hénon | Uni | F(Uni) | Nor | F(Nor) | Co |
|---|---|---|---|---|---|---|---|---|---|
| VDP | 10 |  |  |  |  |  |  |  |  |
| Lor |  | 9 |  |  |  |  |  | 1 |  |
| Rös |  |  | 10 |  |  |  |  |  |  |
| Hénon |  |  |  | 10 |  |  |  |  |  |
| Uni |  |  |  |  | 10 |  |  |  |  |
| F(Uni) |  | 1 |  |  |  |  | 8 | 1 |  |
| Nor |  |  |  | 1 |  |  | 9 |  |  |
| F(Nor) |  |  |  |  |  |  |  | 10 |  |
| Co |  |  |  |  |  |  |  |  | 10 |

FIGURE 5k

|  | VDP | Lor | Rös | Hénon | Uni | F(Uni) | Nor | F(Nor) | Co |
|---|---|---|---|---|---|---|---|---|---|
| VDP | 10 |  |  |  |  |  |  |  |  |
| Lor |  | 9 |  |  |  |  |  | 1 |  |
| Rös |  |  | 10 |  |  |  |  |  |  |
| Hénon |  |  |  | 10 |  |  |  |  |  |
| Uni |  |  |  |  | 10 |  |  |  |  |
| F(Uni) |  |  |  |  |  | 9 |  | 1 |  |
| Nor |  |  |  | 1 | 1 |  | 8 |  |  |
| F(Nor) |  |  |  |  |  |  |  | 10 |  |
| Co |  |  |  |  |  |  |  |  | 10 |

FIGURE 5l

|       | VDP | Lor    | Rös              | Hénon            | Uni              | F(Uni)           | Nor              | F(Nor)           | Co               |
|-------|-----|--------|------------------|------------------|------------------|------------------|------------------|------------------|------------------|
| VDP   |     | 0.0447 | $0.2 \times 10^{-7}$ | $0.4 \times 10^{-6}$ | $0.3 \times 10^{-6}$ | 0.0047           | $0.9 \times 10^{-5}$ | 0.1917           | $10^{-6}$        |
| Lor   |     |        | $< 10^{-8}$      | $10^{-7}$        | $10^{-8}$        | 0.0774           | $0.6 \times 10^{-6}$ | 0.1960           | $0.3 \times 10^{-5}$ |
| Rös   |     |        |                  | $< 10^{-8}$      | $< 10^{-8}$      | $0.2 \times 10^{-7}$ | $< 10^{-8}$      | $< 10^{-8}$      | $< 10^{-8}$      |
| Hénon |     |        |                  |                  | 0.0009           | $< 10^{-8}$      | 0.0183           | $0.7 \times 10^{-7}$ | 0.0125           |
| Uni   |     |        |                  |                  |                  | $< 10^{-8}$      | 0.7698           | $0.8 \times 10^{-7}$ | 0.0022           |
| F(Uni)|     |        |                  |                  |                  |                  | $0.7 \times 10^{-7}$ | 0.0544           | $< 10^{-8}$      |
| Nor   |     |        |                  |                  |                  |                  |                  | $0.8 \times 10^{-6}$ | 0.0391           |
| F(Nor)|     |        |                  |                  |                  |                  |                  |                  | $0.5 \times 10^{-6}$ |
| Co    |     |        |                  |                  |                  |                  |                  |                  |                  |

FIGURE 5m

|       | VDP | Lor    | Rös              | Hénon  | Uni              | F(Uni)           | Nor              | F(Nor)           | Co               |
|-------|-----|--------|------------------|--------|------------------|------------------|------------------|------------------|------------------|
| VDP   |     | 0.0890 | $0.3 \times 10^{-4}$ | 0.0007 | 0.0006           | 0.0889           | 0.0070           | 0.2277           | 0.0018           |
| Lor   |     |        | $0.8 \times 10^{-5}$ | 0.0003 | $0.2 \times 10^{-4}$ | 0.1830           | 0.0011           | 0.2289           | 0.0032           |
| Rös   |     |        |                  | $< 10^{-8}$ | $< 10^{-8}$ | $0.3 \times 10^{-4}$ | $0.3 \times 10^{-7}$ | $0.2 \times 10^{-4}$ | $< 10^{-8}$      |
| Hénon |     |        |                  |        | 0.0534           | $0.2 \times 10^{-5}$ | 0.1284           | 0.0001           | 0.1163           |
| Uni   |     |        |                  |        |                  | $0.6 \times 10^{-5}$ | 0.3439           | 0.0002           | 0.0710           |
| F(Uni)|     |        |                  |        |                  |                  | 0.0001           | 0.1681           | $0.5 \times 10^{-5}$ |
| Nor   |     |        |                  |        |                  |                  |                  | 0.0014           | 0.1552           |
| F(Nor)|     |        |                  |        |                  |                  |                  |                  | 0.0010           |
| Co    |     |        |                  |        |                  |                  |                  |                  |                  |

FIGURE 5n

|        | VDP | Lor | Rös | Hénon | Uni | F(Uni) | Nor | F(Nor) | Co |
|--------|-----|-----|-----|-------|-----|--------|-----|--------|----|
| VDP    | 9   |     |     |       |     |        |     | 1      |    |
| Lor    |     | 9   |     |       |     | 1      |     |        |    |
| Rös    |     |     | 10  |       |     |        |     |        |    |
| Hénon  |     |     |     | 10    |     |        |     |        |    |
| Uni    |     |     |     |       | 6   |        | 4   |        |    |
| F(Uni) |     | 2   |     |       |     | 7      |     | 1      |    |
| Nor    |     |     |     | 1     | 1   |        | 7   |        | 1  |
| F(Nor) | 3   | 1   |     |       |     |        |     | 6      |    |
| Co     |     |     |     |       | 1   |        | 1   |        | 8  |

FIGURE 5o

|        | VDP | Lor | Rös | Hénon | Uni | F(Uni) | Nor | F(Nor) | Co |
|--------|-----|-----|-----|-------|-----|--------|-----|--------|----|
| VDP    | 9   |     |     |       |     |        |     | 1      |    |
| Lor    |     | 6   |     |       |     | 3      |     | 1      |    |
| Rös    |     |     | 10  |       |     |        |     |        |    |
| Hénon  |     |     |     | 9     | 1   |        |     |        |    |
| Uni    |     |     |     |       | 6   |        | 4   |        |    |
| F(Uni) |     | 1   |     |       |     | 9      |     |        |    |
| Nor    |     |     |     |       | 1   |        | 8   |        | 1  |
| F(Nor) | 1   | 1   |     |       |     | 2      |     | 6      |    |
| Co     |     |     |     | 1     |     |        | 1   |        | 8  |
FIGURE 5p
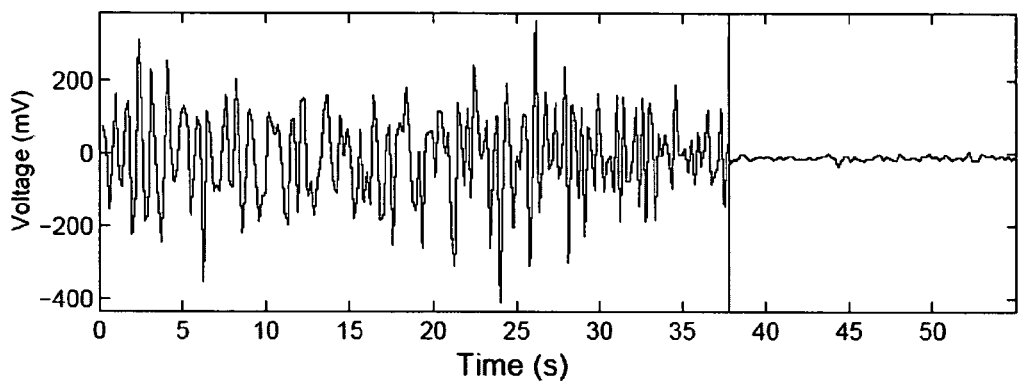
FIGURE 6a
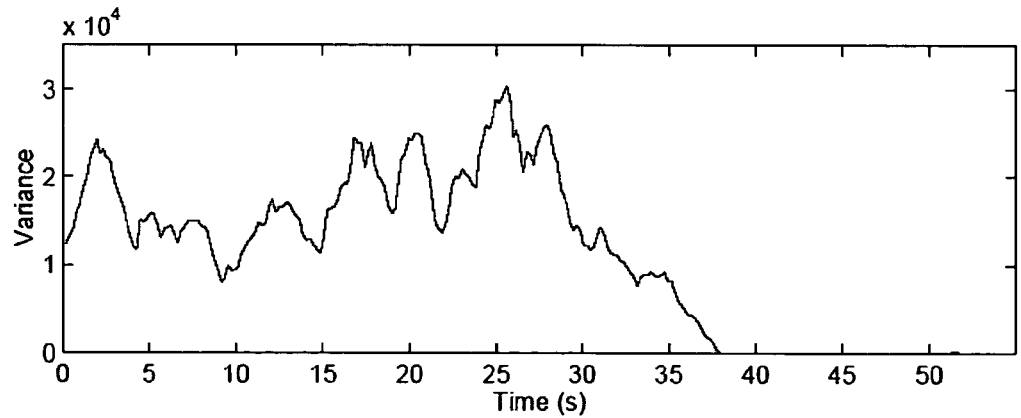
FIGURE 6b

SYSTEM AND METHOD FOR CATEGORICAL ANALYSIS OF TIME DEPENDENT DYNAMIC PROCESSES

CROSS REFERENCE TO RELATED APPLICATION

This application claims the benefit of U.S. Provisional Patent Application Ser. No. 60/473,788, filed May 28, 2003, which is incorporated by reference as if fully set forth herein.

STATEMENT REGARDING FEDERALLY SPONSORED RESEARCH OR DEVELOPMENT

This invention was supported in part by Contract No. N66001-00-C-8012 from the Space and Naval Warfare Systems Center and Award No. H235J000001 from the U.S. Department of Education. The U.S. Government may have certain rights in the invention.

FIELD OF INVENTION

The present invention relates to a system and method for categorical analysis of time dependent dynamic processes such as classifying a signal into a library composed of several distinct groups.

BACKGROUND

The classification of a signal, the detection of an event or change in a system through the analysis of a signal, or the prediction of a change or event are all classical problems in many areas of engineering.

The classification of a signal into a library composed of several distinct groups is a classical problem in the signal processing literature. The objective can be stated simply: Given a test signal, it is desired to know if the signal is likely to be a member of previously characterized groups that comprise the library. Also, it is desired to know the accuracy (confidence) of the assignment of the signal. This problem presents itself in most areas of engineering practice. This problem is also encountered in the analysis of biological data, particularly behavioral data, and in clinical applications. For example, in the course of investigations of animal behavior, one often wants to characterize the degree of similarity in the behavior of a specific animal against previously observed control data and against data obtained after the administration of drugs.

Clinically, the classification problem is encountered during diagnostic procedures. Given a patient's ECG or EEG, it is desirable to know the probability that the signal correlates with healthy, age-matched control subjects and/or the probability that the signal correlates with a set of well characterized clinical signals of a particular abnormality or condition.

In general, it would be desirable to provide a system and method for categorizing measurable time dependent data with a relatively high probability correlation with one or more sets from among a group of sets that define a library of well characterized conditions or groups.

SUMMARY

A system and method for performing a categorical analysis on one or more time dependent dynamic processes is provided. A reference library of data pertaining to multiple characteristics of time series reflective of the dynamic process is used to define selected categories for performing the categorical analysis.

The categorical analysis method preferably includes capturing a time series associated with a selected type of dynamic process. Based on the selected type of dynamic process, a reference library of data of different quantifiable dynamic characteristics of reference time series is selected wherein the data is segmented into at least one classification of groups. Preferably, each classification's segmentation into groups represents a correlation of quantified dynamic data of a predefined set of a plurality of quantifiable dynamic classification characteristics from among the different quantifiable dynamic characteristics. Quantified dynamic data of the captured time series is processed for the predefined set of quantifiable dynamic classification characteristics of a selected classification of groups within the reference library. The captured time series is then classified with respect to the groups of the selected classification based on the processed quantified dynamic data of the captured time series.

The time series may be bio-metric related signals based on things such as brain waves, heart beat, locomotive behavior, but can be based on any dynamic event that changes over time. Many common tests produce time series which provide data that may form the basis of a categorical analysis using the invention. Examples include electroencephalograms (EEGs) and electrocardiograms (ECGs). Alternatively, one may readily devise a customized method capturing time series data such as described below in connection with categorizing locomotive behavior based on characteristics of movement trajectories of goldfish.

Preferably, a first set of quantifiable dynamic classification characteristics for a first classification of groups includes characteristics such as characteristic fractal dimension, Richardson dimension, Lempel-Ziv complexity, Hurst exponent and/or relative dispersion. The processing of quantified dynamic data of the captured time series is then done for the first set of quantifiable dynamic classification characteristics of the first classification of groups within the reference library. The classifying of the captured time series is accordingly made with respect to the groups of the first classification.

Additional sets of quantifiable dynamic classification characteristics for additional classification of groups may be defined in the reference library. The processing of quantified dynamic data of the captured time series may then also be done for the additional sets of quantifiable dynamic classification characteristics of the respective classification of groups within the reference library. The classifying of the captured time series may then also be made with respect to the groups of one or more of the additional classifications.

The classifying of the captured time series with respect to the groups of the selected classification based on the processed quantified dynamic data of the captured time series preferably includes calculating the probabilities that the processed quantified dynamic data of the captured time series is a member of each group of the selected classification. Calculating of the probabilities that the processed quantified dynamic data of the captured time series is a member of each group of the selected classification preferably includes calculating probabilities using minimum Mahalanobis distance and/or maximum Bayesian likelihood.

The captured time series is preferably classified in the group for which a highest probability of membership is calculated. Alternatively, the captured time series may be classified as a member of each group for which a calculated probability of membership exceeds a membership threshold. Further alternatives are available such as classifying the captured time series as not a member of each group for which a calculated probability of membership does not exceed a membership threshold.

A preferred system for categorical analysis of time dependent dynamic processes includes a processor and a memory unit coupled with the processor. The processor preferably has an input for receiving data of quantified dynamic characteristics of a captured time series associated with a selected type of dynamic process. The memory unit preferably includes a reference library of data of different quantifiable dynamic characteristics of reference time series associated with the selected type of dynamic process. The data is segmented into at least one classification of groups where each classification's segmentation into groups represents a correlation of quantified dynamic data of a predefined set of a plurality of quantifiable dynamic classification characteristics from among the different quantifiable dynamic characteristics. The processor is preferably configured to process quantified dynamic characteristic data of the captured time series for the set of classification characteristics of a selected classification of groups within the reference library to classify the captured time series with respect to the groups of the selected classification based on the processed quantified dynamic characteristic data.

The processor is preferably configured to process quantified dynamic data of the captured time series for a first set of quantifiable dynamic classification characteristics of a first classification of groups within the reference library to classify the captured time series with respect to the groups of the first classification by calculating the probabilities that the processed quantified dynamic data of the captured time series is a member of each group of the first classification. The processor configuration in calculating such probability preferably is based upon using minimum Mahalanobis distance and/or maximum Bayesian likelihood.

The processor configuration for classifying the captured time series is preferably set to classify it in the group for which a highest probability of membership is calculated. Alternatively, the processor may be configured to classify the captured time series as a member or mot a member of a group based on a threshold comparison.

A method for creating a reference library of data for use in performing categorical analysis of time dependent dynamic processes preferably includes capturing reference time series associated with a selected type of dynamic process. Data of selected quantifiable dynamic characteristics for each reference time series is derived. The data is segmented into at least one classification of groups where each classification's segmentation into groups represents a correlation of data of a predefined set of quantified dynamic classification characteristics from among the selected quantified dynamic characteristics. This enables the above classification method to be used such that a subject captured time series of the selected type of dynamic process can be classified into a group of the selected classification based on correlating quantified dynamic data derived from the subject captured time series corresponding to the predefined set of quantified dynamic classification characteristics of the selected classification of groups.

Preferably, a first set of quantifiable dynamic classification characteristics for a first classification of groups is defined by deriving data for at least three quantifiable dynamic characteristics for at least a selected minimum number of reference time series from each group of the first classification of groups. Effectiveness with respect to each quantifiable dynamic characteristic can be calculated based on the respective data derived for the reference time series of each respective group. At least two quantifiable dynamic characteristics that have the highest calculated effectiveness are then selected for inclusion in the first set of quantifiable dynamic classification characteristics for the first classification of groups.

Further sets of quantifiable dynamic classification characteristics for additional classifications of groups can be defined by deriving data for at least three quantifiable dynamic characteristics for at least a selected minimum number of reference time series from each group of the additional classifications of groups. For the respective groups of each additional classification, effectiveness with respect to each quantifiable dynamic characteristic can be calculated based on the respective data derived for the reference time series of each respective group of the respective classification of groups. Preferably, at least two quantifiable dynamic characteristics that have highest calculated effectiveness are then selected for inclusion in the respective additional set of quantifiable dynamic classification characteristics for each additional classification of groups.

For efficiency, data derived for defining the one set of quantifiable dynamic classification characteristics is also used for defining other sets of quantifiable dynamic classification characteristics where a reference time series is included in a group of the both classifications of groups. Preferably, data is derived for quantifiable dynamic characteristics such as fractal dimension, Richardson dimension, Lempel-Ziv complexity, Hurst exponent and/or relative dispersion.

One preferred method for calculating effectiveness with respect to each quantifiable dynamic characteristic based on the respective data derived for the reference time series of each respective group includes calculating partial F-values with respect to each quantifiable dynamic characteristic based on the respective data derived for the reference time series of each respective group.

The present invention provides a novel approach of incorporating multiple nonlinear dynamical measures into a multivariate discrimination that results in a signal classification system which is highly sensitive and robust to additive noise. More specifically, computationally generated signals and radioactive decay data have been used by the inventors to demonstrate that the incorporation of nonlinear dynamical measures into a multivariate discrimination can provide a signal classification system that is robust against additive noise to a signal to noise ratio of 0 dB.

Other objects and advantages of the invention will be apparent to those skilled in the art from the following description, given by way of example and to be understood in conjunction with the accompanying drawings.

BRIEF DESCRIPTION OF THE DRAWINGS

FIGS. 5a through 5p are tables illustrating the results obtained in validating a classification system of a first example constructed in accordance with the teachings of the present invention.

FIG. 6a is a graphic illustration of an ECT time series with clinician's indication of seizure termination derived in a second example of a system constructed in accordance with the teachings of the present invention.

FIG. 6b is a graphic illustration of a corresponding variance measure for successive epochs with respect to the ECT time series of FIG. 6a.

FIG. 7b is a graphic illustration of a corresponding correlation integral measure for successive epochs with respect to the ECT time series of FIG. 7a.

FIG. 8b is a graphic illustration of a corresponding return map during the seizure with respect to the ECT time series of FIG. 8a.

FIG. 8c is a graphic illustration of a corresponding return map after seizure termination with respect to the ECT time series of FIG. 8a.

DETAILED DESCRIPTION OF THE PREFERRED EMBODIMENT

Figure 1:
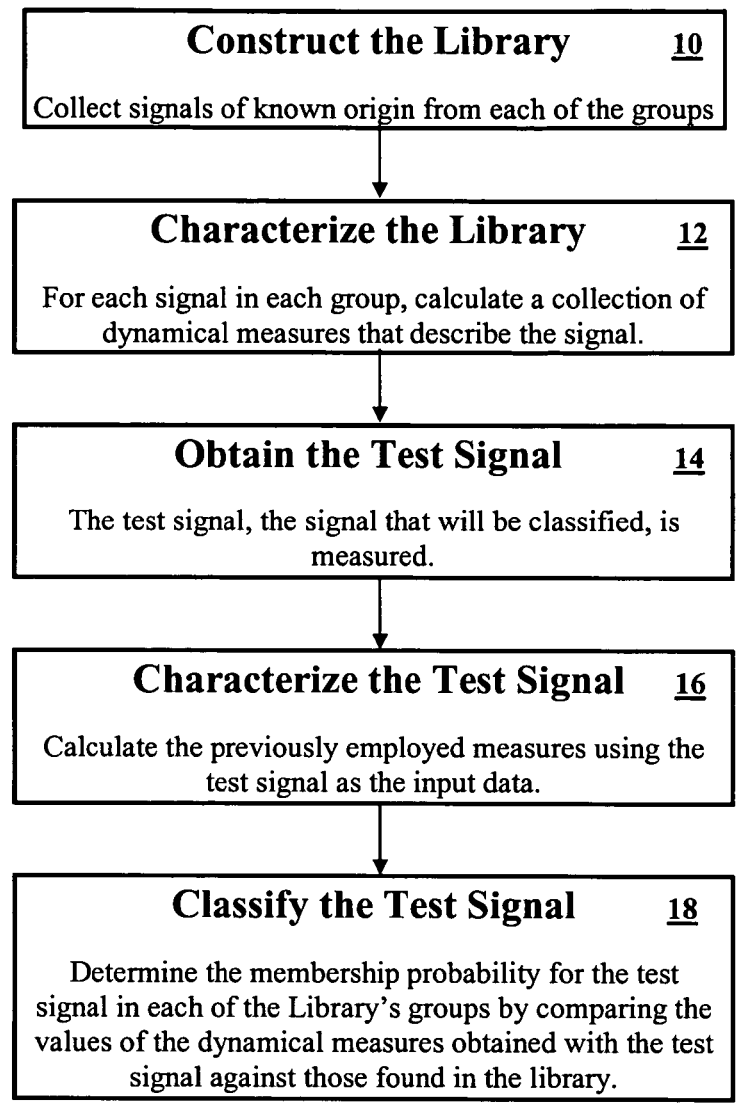
FIG. 1 is an overall flowchart of the processes related to a dynamic signal classification system made in accordance with the teachings of the present invention.
Figure 2:
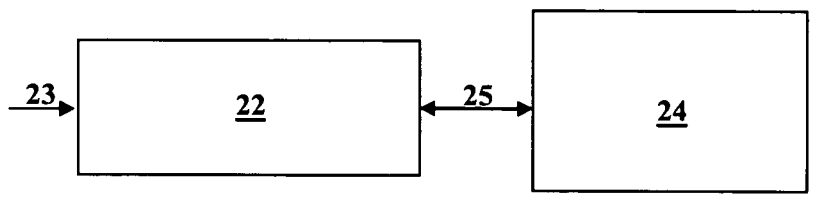
FIG. 2 is a block diagram of a dynamic signal classification system made in accordance with the teachings of the present invention.
Figure 3A:
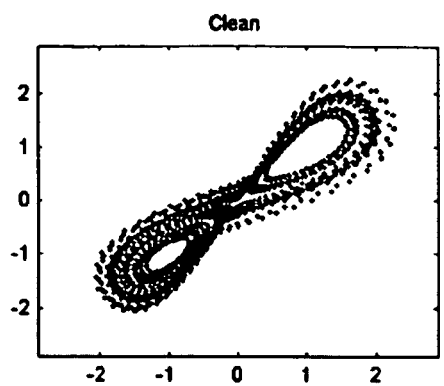
FIGS. 3a–3d are graphs illustrating the effect of additive noise on the structure of deterministic signals.
Figure 3B:
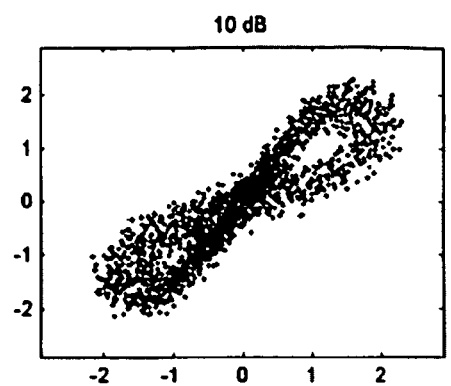
Figure 3C:
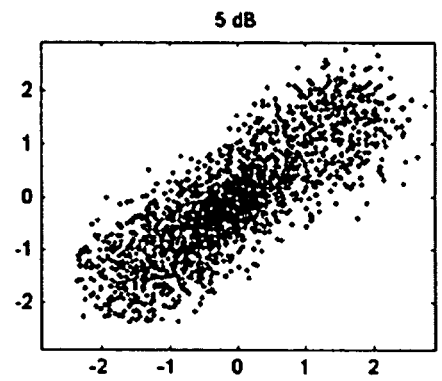
Figure 3D:
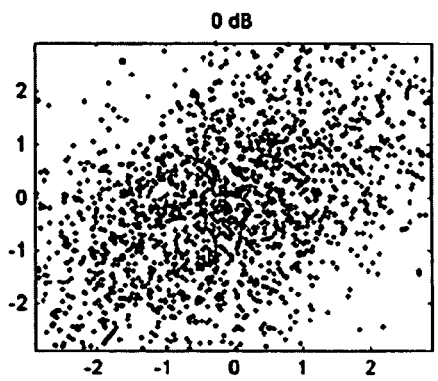

In general, the invention involves two parts: the creation of a selectively defined library of reference data with classification segmentation or indexing and the categorical analysis of a subject based on data derived therefrom. With reference to FIG. 1, a flow chart of the complete methodology is provided with the first two steps 10, 12 reflecting the steps for the creation of the selectively defined library and the last three steps 14, 16, 18 reflecting the categorical analysis. The methodology can be readily implemented using a computer system. For example, a preferred system includes a processor 22 having a data input 23 and a data storage device 24 connected with the processor through an interface 25 as illustrated in FIG. 2.

A library is created to form the basis of categorical analysis of a selected dynamic process based on reference signals obtained from control groups that define the categories with respect to which the categorical analyses will be made. Signals are generally in the form of some type of a time series of data. The signals are typically the recorded observations of a physical or biological dynamical system. Examples include almost any electromagnetic signal, such as electroencephalograms (EEG), electrocardiograms (ECG), radar, or an acoustic signal like sonar. Alternatively, one may readily devise a customized method capturing time series data such as described below in connection with categorizing locomotive behavior based on characteristics of movement trajectories of goldfish. More abstract time series such as the price of a commodity traded on a market can be made the subject of categorical analysis in accordance with the invention.

As an initial step 10, signals are collected of known origin for each of the groups defined in a selected classification of groups. Time series data of such signals may be input to the system 20 and stored as files of raw data in the memory device 24. Multiple classifications for the same types of signals may be defined so that the raw data can be efficiently utilized for multiple types of categorical analysis. Preferably, each time series data record contains an indication of each classification and respective group of the classification to which it pertains. The number of signals and their characteristics, such as sampling rate, or filtering parameters is dependent on the classification problem.

The second step 12 in the library creation involves characterizing and segmenting the files of raw time series data from the reference signals. Each signal in the library is "characterized" using a plurality of nonlinear measures which are chosen according to the characteristics of the signal and the parameters of the classification problem. These nonlinear measures can be relatively standard, such as the measurement of the Lempel-Ziv Complexity, or much more convoluted. Examples of the latter generally begin with a time-delayed embedding of the signal into a higher dimensional space.

One procedure is based on the Takens-Mane Embedding Theorem. This embedding creates a geometrical object, or "attractor" in a higher dimensional space which then can be characterized using the tools of geometry. The estimation of the largest Lyapunov Exponent would be an example of such a tool. The theory behind this approach is that when a signal is recorded from a dynamical system, only a single variable, or at most a small subset, of all the variables of the system is being measured.

As an example, when an EEG is recorded, the signal measured is the collective electromagnetic activity of millions of neurons. This signal is measured over only a very small subset of the brain. However, there is the assumption that the variables, in this case neurons, in this system are coupled. If they are coupled, then the resulting "attractor" of the system will contain information not only about the variables measured, but also about the overwhelming number of variables that were not measured. Applying the principles of the Takens-Mane Embedding Theorem in nonlinear dynamical analysis results in the ability to make classifications at a very sensitive level.

Preferably, a first set of quantifiable dynamic classification characteristics for a first classification of groups is defined by deriving data for at least three quantifiable dynamic characteristics for at least a selected minimum number of reference time series from each group of the first classification of groups. Preferred quantifiable dynamic characteristics include characteristics such as fractal dimension, Richardson dimension, Lempel-Ziv complexity, Hurst exponent and/or relative dispersion.

In the example system illustrated in FIG. 2, the processor 22 is used to calculate the characteristics from raw time series data records stored in the memory device 24 and the resultant characteristic values are stored in the memory device. The calculated characteristic values can be stored in the same data record with the raw data from which the characteristic values are derived or in separate records. After all characteristic values are determined the raw data can be removed from the data storage device 24 and archived for further use, if desired. Preferably, each time series characteristic values data record contains an indication of each classification and respective group of the classification to which it pertains.

One way to select the characteristics that are used for a specific classification is to determine the relative effectiveness of each characteristic. Effectiveness with respect to each quantifiable dynamic characteristic can be calculated based on the respective data derived for the reference time series of each respective group. At least two quantifiable dynamic characteristics that have the highest calculated effectiveness are then selected for inclusion in the first set of quantifiable dynamic classification characteristics for the first classification of groups. If two or more of the initially used characteristics do not demonstrate sufficient classification effectiveness, additional characteristics can be derived and their effectiveness determined.

One preferred method for calculating effectiveness with respect to each quantifiable dynamic characteristic based on the respective data derived for the reference time series of each respective group includes calculating partial F-values with respect to each quantifiable dynamic characteristic based on the respective data derived for the reference time series of each respective group. Partial F statistics can be used to examine the contribution of a single quantifiable characteristic known in statistical terminology as regressors. For example, in a linear model with p regressors (x) and p partial regression coefficients ($\beta$):

$$\mu_Y = \beta_0 + \beta_1 x_1 + \beta_2 x_2 + \beta_3 x_3 + \ldots + \beta_p x_p$$

which represents a "full" model, can be compared with a reduced model:

$$\mu_Y = \beta_0 + \beta_1 x_1 + \beta_2 x_2 + \beta_3 x_3 + \ldots + \beta_{p-1} x_{p-1}$$

(i.e., $\beta_p = 0$). This allows testing of the redundancy of the $p^{th}$ variable. The first step is to compute the two minimum sums of squares $S^p$ (full model) and $S^{p-1}$ (reduced model). The partial F-statistic is constructed as:

$$F = (S^{p-1} - S^p) / (S^p / (n-p-1))$$

By comparing the realized F-value with the $(1-\alpha)$ quantile of the corresponding F-distribution, the partial hypothesis $\beta_p = 0$ can be tested.

Further sets of quantifiable dynamic classification characteristics for additional classifications of groups can be defined by deriving data for at least three quantifiable dynamic characteristics for at least a selected minimum number of reference time series from each group of the additional classifications of groups. For the respective groups of each additional classification, effectiveness with respect to each quantifiable dynamic characteristic can be calculated based on the respective data derived for the reference time series of each respective group of the respective classification of groups. Preferably, at least two quantifiable dynamic characteristics that have highest calculated effectiveness are then selected for inclusion in the respective additional set of quantifiable dynamic classification characteristics for each additional classification of groups. For efficiency, data derived for defining the one set of quantifiable dynamic classification characteristics is also used for defining other sets of quantifiable dynamic classification characteristics where a reference time series is included in a group of both classifications of groups.

Once the classification library is created, the categorical analysis of a subject can be performed such as by performing steps 14, 16 and 18 of FIG. 1. The initial step 14 for the analysis is to capture time series data for the subject which is to be classified. Typically, this entails the measurement of a test or subject signal of the type used to construct the library.

In step 16, the subject test signal is characterized, preferably by using the same nonlinear measures which were used in the creation of the library classification group or groups of the type of signal being classified. This enables classification of the subject test signal to be performed in step 18.

The characterizing step 16 is customized for the selected type of dynamic process which the test signal represents. Based on the selected type of dynamic process, a reference library of data of different quantifiable dynamic characteristics of reference time series is selected wherein the data is segmented into at least one classification of groups. As noted above, each classification's segmentation into groups preferably represents a correlation of quantified dynamic data of a predefined set of a plurality of quantifiable dynamic classification characteristics from among the different quantifiable dynamic characteristics. Quantified dynamic data of the captured time series is processed for the predefined set of quantifiable dynamic classification characteristics of a selected classification of groups within the reference library. The captured time series is then classified with respect to the groups of the selected classification based on the processed quantified dynamic data of the captured time series.

Preferably, a first set of quantifiable dynamic classification characteristics for a first classification of groups includes characteristics such as fractal dimension, Richardson dimension, Lempel-Ziv complexity Hurst exponent and/or relative dispersion. The processing of quantified dynamic data of the captured time series is then done for the first set of quantifiable dynamic classification characteristics of the first classification of groups within the reference library. The classifying of the captured time series is accordingly made with respect to the groups of the first classification.

Where additional sets of quantifiable dynamic classification characteristics for additional classification of groups are defined in the reference library, the processing of quantified dynamic data of the captured time series may then also be done for the additional sets of quantifiable dynamic classification characteristics of the respective classification of groups within the reference library. The classifying of the captured time series may then also be made with respect to the groups of one or more of the additional classifications.

Preferably in step 18, the classifying of the captured time series with respect to the groups of the selected classification based on the processed quantified dynamic data of the captured time series preferably includes calculating the probabilities that the processed quantified dynamic data of the captured time series is a member of each group of the selected classification. Calculating of the probabilities that the processed quantified dynamic data of the captured time series is a member of each group of the selected classification preferably includes calculating probabilities using minimum Mahalanobis distance and/or maximum Bayesian likelihood.

The captured time series is preferably classified in the group for which a highest probability of membership is calculated. Alternatively, the captured time series may be classified as a member of each group for which a calculated probability of membership exceeds a membership threshold. Further alternatives are available such as classifying the captured time series as not a member of each group for which a calculated probability of membership does not exceed a membership threshold. A signal can have a low probability of membership in any of the groups which can then be interpreted as a unique signal of a new group.

FIG. 2 illustrates a prefer system for categorical analysis of time dependent dynamic processes that includes the processor 22 and memory unit 24 coupled with the processor. The processor 22 preferably uses its input 24 for receiving data of quantified dynamic characteristics of a captured time series associated with a selected type of dynamic process. The memory unit 24 preferably includes the reference library of data of different quantifiable dynamic characteristics of reference time series associated with the selected type of dynamic process. The data is segmented into at least one classification of groups where each classification's segmentation into groups represents a correlation of quantified dynamic data of a predefined set of a plurality of quantifiable dynamic classification characteristics from among the different quantifiable dynamic characteristics. The processor 22 is preferably configured to process quantified dynamic characteristic data of the captured time series for the set of classification characteristics of a selected classification of groups within the reference library to classify the captured time series with respect to the groups of the selected classification based on the processed quantified dynamic characteristic data.

The processor 22 is preferably configured to process quantified dynamic data of the captured time series for a first set of quantifiable dynamic classification characteristics of a first classification of groups within the reference library to classify the captured time series with respect to the groups of the first classification by calculating the probabilities that the processed quantified dynamic data of the captured time series is a member of each group of the first classification. The processor configuration in calculating such probability preferably is based upon using minimum Mahalanobis distance and/or maximum Bayesian likelihood.

The processor configuration for classifying the captured time series is preferably set to classify it in the group for which a highest probability of membership is calculated. Alternatively, the processor may be configured to classify the captured time series as a member or not a member of a group based on a threshold comparison.

EXAMPLE 1

Validation of Methodology

The present invention incorporates nonlinear dynamical measures into a multivariate discrimination to provide a signal classification system that is robust to additive noise. The sample signal library was constructed composed of nine groups of signals. Four groups were generated computationally from deterministic systems (van der Pol, Lorenz, Rössler and Hénon). Four groups were generated computationally from different stochastic systems. The ninth group contained inter-decay interval sequences from radioactive cobalt. Two classification criteria (minimum Mahalanobis distance and maximum Bayesian likelihood) were tested.

In the absence of additive noise, no errors occurred in a within-library classification. Normally distributed random numbers were added to produce signal to noise ratios of 10, 5 and 0 dB. When the minimum Mahalanobis distance was used as the classification criterion, the corresponding error rates were 2.2%, 4.4% and 20% (Expected Error Rate=89%). When Bayesian maximum likelihood was the criterion, the error rates were 1.1%, 4.4% and 21% respectively. Using nonlinear measures, an effective discrimination was achieved in cases where spectral measures are known to fail.

Most classification errors occurred at low signal to noise ratios when a stochastic signal was misclassified into a different group of stochastic signals. When the within-library classification exercise was limited to the four groups of deterministic signals, no classification errors occurred with clean data, at SNR=10 dB, or at SNR=5 dB. A single classification error (Observed Error Rate=2.5%, Expected Error Rate=75%) occurred with both classification criteria at SNR=0 dB.

1. Sample Signal Library
Nine groups of signals were incorporated:
Group 1: the periodic van der Pol equation;
Group 2: the Lorenz equations;
Group 3: the Rössler equations;
Group 4: the Hénon system;
Group 5: uniformly distributed random numbers;

Group 6: filtered uniformly distributed random numbers;
Group 7: normally distributed random numbers;
Group 8: filtered normally distributed random numbers; and
Group 9: the time intervals between successive beta emissions from $Co^{60}$.

In the case of van der Pol, Lorenz, Rössler and Hénon data, the equations were iterated for ten thousand time steps from the initial values before data were recorded. The van der Pol, Lorenz, and Rössler equations were integrated using a sixth-order Runge-Kutta-Huta algorithm. The governing equations for the van der Pol system were:

$$\frac{dx}{dt} = y + 2\left[x - \frac{x^3}{3}\right]$$

$$\frac{dy}{dt} = -x$$

The sampling interval was h=0.05.

The governing equations for the Lorenz system were:

$$\frac{dx}{dt} = -\sigma(x-y)$$

$$\frac{dy}{dt} = -xz + rx - y$$

$$\frac{dz}{dt} = xy - bz$$

where $\sigma=10$, $b=8/3$ and $r=28$. The sampling interval was h=0.01.

The governing equations for the Rössler equations were:

$$\frac{dx}{dt} = -y - z$$

$$\frac{dy}{dt} = x + ay$$

$$\frac{dz}{dt} = b + xz - cz$$

where a=0.2, b=0.4 and c=5.7. The sampling interval was h=0.10.

The Hénon data sets were produced by iterating the Hénon map, a=1.4 and b=0.3.

$$x_{n+1} = 1 - ax_n^2 + y_n$$

$$y_{n+1} = bx_n$$

The sets of uniformly distributed random numbers were generated using a Park-Miller random number generator that incorporated a Bays-Durham shuffle. Data sets of uniformly distributed random numbers were filtered to produce an additional group. The Fourier transform of 8,192 uniformly distributed random numbers was calculated. The coefficient of the jth harmonic was multiplied by:

$$F_j = \max|0, 1 - kj^2| \; k = 0.37 \times 10^{-6}$$

The corresponding inverse transform was used in subsequent calculations.

Group 7 consisted of normally distributed random numbers that were produced by transforming random data generated by the Park-Miller random number generator to a normal distribution. The mean of each data set was approximately zero and the standard deviation was approximately one.

An additional group of data sets, Group 8, was produced by filtering the normally distributed random numbers of Group 7. The calculations began with 16,384 normally distributed random numbers. The Fourier transform of this time series was calculated. The coefficients of the jth harmonic were multiplied by one for j=1, ..., 192 and by zero for j=193, ..., 8,192. The inverse transform was then calculated giving a time series of 16,384 elements. In order to minimize the end effects produced by using a step function filter, a final filtered data set was constructed by extracting the middle 8,192 elements of the inverse transform.

These data sets of filtered random numbers differ from the previous sets (Group 6) in two ways. First, the input to the filter was uniformly distributed in the case of Group 6 and normally distributed in the case of Group 8. Additionally, the filter in Group 8 was far more severe. In the case of Group 6, the first 1,643 coefficients of 4,096 harmonics made a nonzero contribution to the inverse transform. In the case of Group 8, only 192 coefficients of 8,192 were retained.

The final group of time series, Group 9, consists of the successive inter-decay intervals recorded from $Co^{60}$.

Since the classification system can be used with biological signals, an assessment of the system's robustness to noise is desirable. A distinction can be made between different types of noise. Three classes can be considered: additive or observational noise introduced by simply adding random numbers after the entire signal was computed; dynamic noise introduced by adding random numbers to the dependent variables after each iteration of the computation; and parametric noise introduced into the system by replacing a parameter in the governing equations.

In the case of dynamic noise, where, for example, values of x, y and z at the ith time step have been determined a random number can be added to each of these values before computing the system's position at the next time point. In contrast, parametric noise can be introduced into the system by replacing a parameter in the governing equations, for example, parameter $\sigma$ in the Lorenz equations, with a time dependent stochastic term $\sigma + \epsilon_i$, where $\{\epsilon_i\}$ is a set of random numbers satisfying some specification.

In the computations example presented here, only observational noise was considered. This form of noise is the least destructive to signal integrity. In order to test the classification system's robustness to additive noise, each data set was used to produce three additional time series. Normally distributed random numbers (mean=0) were added to produce signals with a signal to noise ratio of 10 dB, 5 dB and 0 dB. The impact of additive noise can be assessed subjectively by examining the content of FIGS. 3a–3d. Those respective graphs illustrate two-dimensional embeddings of Lorenz data (xi; xi+5) at four different noise levels: clean data, SNR=10 dB, SNR=5 dB, and SNR=0. At SNR=0 dB, the signal variance is equal to the noise variance and the visually discernable geometrical structure of the data is lost.

2. Dynamical Characteristics

Five dynamical measures were used in this example: the characteristic fractal dimension, the Richardson dimension, Lempel-Ziv complexity, the Hurst exponent and the relative dispersion. The number of measures that can be applied is enormous. As a matter of computational practicality, choices must be made. The choice of measures is not arbitrary. An unnecessary failure to classify data can result from inappropriate choices. The selection preferably reflects the known properties of the data and the objectives of the classification process. The results of this example can be used in the analysis of animal motor behavior. This anticipated subsequent application influenced the choice of measures selected. As noted above, the effectiveness of any given measure in the classification process can be assessed quantitatively.

The characteristic fractal dimension, CFD, measures the degree to which a trajectory in an arbitrary dimension departs from a straight-line path. The CFD is greater than or equal to one and has the value one in the case of a straight line. Let $\{p_i, i=1, \ldots, N_{Data}\}$ be a trajectory, that is an ordered sequence of points in $\Re^m$, where $m \geq 2$. In the case of single channel data, $\{x_i, i=1, \ldots, N_{Data}\}$, points are created in $\Re^m$ by embedding, $p_j=(x_j, x_{j+L}, \ldots, x_{j+(m-1)L})$, where $L \in I^+$ is the lag.

Let $d_j=|p_{j+1}-p_j|$, $j=1, \ldots, N_{Data}-1$ where the Euclidean distance is used. Other distance metrics can be used, but the Euclidean metric was selected since Euclidean distances are invariant under an orthogonal transformation. This is helpful when the orthogonal transformation generated by the singular value decomposition is used to reduce noise.

Let:

$$D_{sum} = \sum_{j=1}^{N_{Data}-1} d j$$

and let $$D_{max} = \max |p_i - p_j|, \text{ for all } i, j \text{ pairs}$$

$D_{max}$ is found by considering all possible i, j pairs, not just sequential, i to i+1 pairs. Then $$CFD = \frac{\log D_{sum}}{\log D_{max}}$$

where, since it is expressed as a ratio, the base of the logarithm is immaterial.

The procedure used to apply the CFD to the data sets in the test library was as follows. In the case of the van der Pol data (Group 1), 1024 two-dimensional points, $(x_i, y_i)$, were used in the calculations. The same procedure was used for the Lorenz data (Group 2), the Rössler data (Group 3), and the Hénon data (Group 4). The z values of the Lorenz and Rössler trajectories were not used. In the case filtered uniformly distributed random numbers (Group 6) and the filtered normally distributed random numbers (Group 8), which are univariate data sets, 1024 two-dimensional points of the form $(x_i, x_{i+1})$ were used in the calculations. For uniformly distributed random numbers (Group 5), normally distributed random numbers (Group 7) and cobalt disintegrations (Group 9), 1024 two-dimensional points of the form $(x_i, x_{i+1024})$ were used in the calculations. A different procedure was used for filtered and unfiltered random numbers because the filtered random numbers have a nonzero autocorrelation time.

As in the case of the CFD, the Richardson dimension ($D_R$) is a measure of the degree to which a trajectory departs from a straight-line path. Additionally, it provides a quantitative characterization of how the estimate of the length of a curve changes with the precision of the measurement. This is the classical coastline of Britain problem. $D_R$, like the CFD, is greater than or equal to one, and has the value $D_R=1$ in the case of a straight line.

Let $p_i$, $i=1, \ldots, N_{Data}$ be a trajectory in $\Re^m$. Let $\tau$ denote a step length, $\tau \in I+$. Let $$d(\tau)_j = |p(j-1)_{\tau+1} - p(j)_{\tau+1}|, j = 1, \ldots J_{max}$$

$$J_{max} = Int\left(\frac{N_{Data}}{\tau}\right) - 1$$

where Int(z) is the least integer greater than or equal to z. $d(\tau)_j$ is the distance between two consecutive points measured in step length $\tau$. Let $$D_{sum}(\tau) = \sum_{j=1}^{J_{max}} d(\tau) j$$

$D_{sum}(\tau)$ is the length of the curve measured in step lengths of $\tau$. As $\tau$ gets bigger, $D_{sum}(\tau)$ decreases. Thus, if $D_{sum}(\tau)$ is plotted as a function of $\tau$, the curve will be monotone decreasing. For many processes, it can be shown that the decreasing function of $D_{sum}(\tau)$ versus has a straight line segment called the scaling region. Let S denote the slope of log $D_{sum}(\tau)$ versus log $\tau$ in the scaling region. The Richardson dimension is then defined by:

$$D_R = |S| + 1$$

where |S| is the absolute value.

A complication is encountered when estimating $D_R$ from finite, noisy data sets; namely, the lower and upper bound of the scaling region must be determined. A numerical procedure can be employed that search for the scaling region by finding the largest range of $\tau$ in which the derivative of log $D_{sum}(\tau)$ versus log $\tau$ is constant to some specified tolerance. In this example, a less demanding procedure was implemented. $D_{sum}(\tau)$ was calculated for $\tau=1, \ldots, 10$ and the slope of the best fit straight line was used to estimate $D_R$. It was recognized that the resulting value was only a very approximate estimate of the true dimension. However, the procedure resulted in a numerically robust measure that has been shown to have empirical value in classifying dynamical systems. The embedding procedures used when calculating the CFD were also used when calculating the Richardson dimension. That is, points were created in two-dimensional space by using the x and y coordinates of multivariate data (van der Pol, Lorenz, Rössler and Hénon) or by embedding univariate data in two dimensions.

The Lempel-Ziv complexity as used in this example is a measure of complexity restricted to the quantitative examination of structure in symbol sequences. Specifically, this complexity measure was a sequence-sensitive measure of a symbol string that gives an indirect measure of the structure of the dynamical system that generated the signal or provides a measure of the degree to which the observed symbol string differs from a random sequence that has the same symbol distribution. By sequence-sensitive, it is meant a measure that changes when the order of the symbols is changed, in contrast with distribution-determined measures. Several different definitions of complexity that satisfy this definition have been constructed. It is possible to construct a taxonomy of complexity measures based on their mathematical properties. In this example, only one of the many complexity possibilities was considered, namely, the Lempel-Ziv measure of complexity which is a nonprobabilistic, model-based, randomness-finding measure.

Two processes preferably precede the application of a complexity measure to dynamical data. First, in the case of a multivariate record, the signal should be expressed in a single channel. Second, the univariate time series of dynamical data should be re-expressed as a symbol sequence. There are a variety of procedures for accomplishing each process. Relatively simple procedures were employed in this example. In the case of the van der Pol data (Group 1), the x and y values form two-dimensional points, $(x_i, y_i)$. A time series $d_j$, $j=1, \ldots, 1024$ was constructed by calculating the distance between consecutive points:

$$d_j = |(x_{j+1}, y_{j+1}) - (x_j, y_j)|$$

where the Euclidean distance is used. The time series $\{d_j\}$ was partitioned into a binary symbol sequence about its median. The complexity of this symbol sequence was then calculated.

The same procedure was used for the Lorenz data (Group 2), the Rössler data (Group 3) and the Hénon data (Group 4). The z values of the Lorenz and Rössler trajectories were not used. In the case of filtered uniformly distributed random numbers (Group 6), and filtered normally distributed random numbers (Group 8), a 1024 point time series $\{d_j\}$ was calculated from the trajectory of two-dimensional points of the form $(x_j, x_{j+1})$. As before, the complexity was calculated after $\{d_j\}$ was partitioned into a binary symbol sequence about its median. For uniformly distributed random numbers (Group 5), normally distributed random numbers (Group 7), and cobalt disintegrations (Group 9), $d_j$, $j=1, \ldots, 1024$ was calculated from successive points of the form $(x_j, x_{j+1024})$.

Once the original data was represented by a symbol sequence, a quantitative measure was constructed that was able to characterize the complexity of the sequence. As stated previously, several candidate measures are available. In this example the Lempel-Ziv measure of complexity, $C_{LZ}$, was used.

A specification of $C_{LZ}$ is preceded by the presentation of necessary definitions and notation. Let message M be a sequence of symbols of length $L_M$.

$$M = \lambda_1 \lambda_2 \ldots \lambda_{LM}$$

If, for example, M=abacedge, then $L_M=8$. The index of a symbol in a message is the positive integer indicating its position. The index of symbol "c" in the preceding example is four. The vocabulary of a symbol sequence, denoted $\upsilon(M)$, is the set of its subsequences. By definition, a symbol sequence is an element of its own vocabulary. If M=abcc, then:

$$\upsilon(M) = \{a, b, c, ab, bc, cc, abc, bcc, abcc\}$$

A symbol string X is said to be an element of M, $X \in m$, if X is an element of the vocabulary of M, $X \in \upsilon(M)$. The concatenation of string X and Y, denoted by $X \oplus Y$, is the symbol sequence formed by appending sequence Y to X. Let Y be a symbol sequence of length $L_Y$. $Y^\pi$, is the symbol sequence of length $L_Y-1$ formed by deleting the last symbol from sequence Y. The notation $\Sigma X_\pi$, denotes $$\Sigma X_\pi = (X_1 \oplus X_2 \oplus \ldots X_J)_\pi$$

The Lempel-Ziv algorithm restates the original symbol sequence M by the concatenation of a uniquely defined series of subsequences.

$$M = X_1 \oplus X_2 \oplus \ldots X_k \oplus X_k \oplus X_{k+1} \ldots \oplus X_N$$

The complexity, $C_{LZ}$, is the positive integer N which is equal to the number of subsequences required by this process. Thus, a crucial element in understanding the algorithm is an understanding of the rule used to specify the subsequences.

The Lempel-Ziv algorithm is initialized with $X_1$ consisting of the first symbol of M only. The length of $X_1$ is always equal to one. Successive subsequences, $X_J$ are constructed by following the previous subsequence and sequentially adding symbols to until $$X_J \notin \{(X_1 \oplus X_2 \ldots \oplus X_J)_\pi\}$$

at which point the generation of $X_J$ is terminated and the construction of $X_{J+1}$ begins.

The process is most effectively presented by considering a specific example such as follows as where M=0 0 0 1 1 0 1 0, then

| | |
|---|---|
| $X_1 = 0$ | |
| $X_2 = 0$ | $X_2 \in (X_1 X_2)_\pi$ |
| $X_2 = 00$ | $X_2 \in (X_1 X_2)_\pi$ |
| $X_2 = 001$ | $X_2 \notin (X_1 X_2)_\pi$ |
| $X_3 = 1$ | $X_3 \in (X_1 X_2 X_3)_\pi$ |
| $X_3 = 1$ | $X_3 \in (X_1 X_2 X_3)_\pi$ |
| $X_3 = 10$ | $X_3 \notin (X_1 X_2 X_3)_\pi$ |
| $X_4 = 1$ | $X_4 \in (X_1 X_2 X_3 X_4)_\pi$ |
| $X_4 = 10$ | $\Sigma_J X = M$ Decomposition Complete |
| | $M = X_1 \oplus X_2 \oplus X_3 \oplus X_4$ |
| | $M = 0 \oplus 001 \oplus 10 \oplus 10$ |

Under this definition, the complexity of symbol sequence M is 4.

By construction, the symbol sequence consisting of the first $L_{J-1}$ elements of subsequence $X_J$ is an element of the vocabulary $\upsilon(\Sigma X_\pi)$. This means that there is an index $I_J$ such that the first $L_J-1$ elements of $X_J$ can be reproduced exactly by copying symbols $\lambda_{I_J} \ldots \lambda_{I_J-(L_{J-1})}$. Therefore, three values can determine $X_J$ exactly. They are (i) $L_J$, its length, (ii) $I_J$, the starting position earlier in the message of the first $L_{J-1}$ elements, and (iii) $S_J$, the identity of the last symbol of subsequence $X_J$. This is true irrespective of the length of $X_J$. Substring $X_J$ could, in the case of a very long message, be ten thousand elements long. Nonetheless, it is fully specified by these three elements. This is the basis of Lempel-Ziv data compression algorithms.

The Hurst exponent characteristic provided a quantitative measure of persistence (like is followed by like: an increase is followed by an increase, a decrease is followed by a decrease) and antipersistence (an increase is followed by a decrease, a decrease is followed by an increase). Persistence is indicated by a value of $H > \frac{1}{2}$, and anti-persistence is indicated by a value $H < \frac{1}{2}$.

Let $\{x_1, x_2, \ldots, x_{N_{Data}}\}$ denote a time series in $\Re^1$. Positive integer $\tau$ is specified. In this example, $\tau$ was varied from $\tau=10$ to $\tau=N_{Data}/2$ in steps of one. The time series is partitioned into sequential, nonoverlapping subepochs containing $\tau$ elements. The Kth subepoch is, therefore, $\{x_{(K-1)\tau+1}, \ldots, x_{K\tau}\}$.

Let $\{x'_1, x'_2, \ldots, x'_\tau\}$ denote the elements of the Kth subepoch following mean normalization within the subepoch. Let $\{S_1, S_2, \ldots S_\tau\}$ denote the sequence generated by calculating the cumulative sum in the Kth subepoch following mean normalization.

$$S_j \sum_{i=1}^{j} x'_i$$

Let $R(\tau)_K$ denote the range of the cumulative sum for the Kth subepoch specified by this value of $\tau$, that is, $$R(\tau)K = \max|S_i - S_j|, \; i,j = 1, \ldots, \tau$$

and let $\sigma_K$ denote the standard deviation of $\{x'_1, x'_2, \ldots, x'_\tau\}$ in subepoch K.

$\langle R^*(\tau) \rangle$ is the average of $R(\tau)_K / \sigma_K R(T)K/QK$ over all subepochs of length $\tau$. It is the average value of the range of the cumulative sum normalized against the variability of the signal. For many dynamical systems, the function log $\langle R^*(\tau) \rangle$ versus log $\tau$ has a linear scaling region. The slope of that line is the Hurst coefficient. As previously noted, T is varied from $\tau = 10$ to $\tau = N_{Data}/2$ in steps of one in our implementation. The estimated value of H is the slope of the best-fit straight line.

The procedures used in the complexity calculations to express multivariate data as a single channel time series were used in the calculations of the Hurst exponent. In the case of van der Pol data, Lorenz data, Rössler data and Hénon data, consecutive (x, y) points were used to calculate the distance function $\{dj\}$. In the case of filtered uniformly distributed random numbers and filtered normally distributed random numbers, $\{d_j\}$ is calculated from two-dimensional points $(x_j, x_{j+1})$. For uniformly distributed random numbers, normally distributed random numbers and cobalt disintegration data, $\{d_j\}$ is calculated from $(x_j, x_{j+1024})$. However, in contrast with complexity calculations, the Hurst exponent was calculated with these time series of real numbers and not with their symbolic reduction.

The relative dispersion characteristic quantified the dependency of variance on the length of the data set. It is expressed as a dimension, $D_{RD}$, and in the case of a straight line $D_{RD+1}$. Let $\{x_1, x_2, \ldots x_{N_{Data}}\}$ denote the time series. In an iterative process, the time series is partitioned into sequential, nonoverlapping subepochs of length $2^1, 2^2, \ldots, 2^{n_{max}}$ where $n_{max}$ is the greatest positive integer such that $2^{n_{max}} \leq N_{Data}/4$.

The following computation is performed in the Kth subepoch of length $\tau$. Let $\langle x(\tau) \rangle_K$ denote the mean of $\{x\}$ in the Kth subepoch. Let $\sigma(\tau)$ denote the standard deviation of the means obtained in subepochs of length $\tau$. That is, $\sigma(\tau)$ is the standard deviation of the set $\{\langle x(\tau) \rangle_1, \langle x(\tau) \rangle_2, \ldots\}$. $\sigma(\tau)$ is a normalization of $\sigma'(\tau)$ defined by:

$$\sigma'(\tau) = \frac{\sigma(\tau)\{\text{number of subepochs of length } \tau - 1\}}{\{\text{number of subepochs of length } \tau\}}$$

Let $\langle x \rangle$ denote the mean of the entire time series. The relative dispersion, $RD(\tau)$ is defined by $$RD(\tau) = \frac{\sigma'(\tau)}{\langle x \rangle}$$

The function log $RD(\tau)$ versus log $\tau$ is a decreasing function. Let S denote the slope of the linear scaling region. Then, $$D_{RD} = 1 + |S|$$

The data reduction protocols used to reduce multivariate data to a single channel in the calculation of the Hurst exponent were also used in the calculation of the relative dispersion.

3. Characterization and Classification Procedures

Four statistical procedures were employed in this example. The first two, calculation of $P_{SAME}(G_A, G_B)$ and $P_{ERROR}(G_A, G_B)$, provided a global characterization of the signal library and the discriminatory capacity of the dynamical measures. The third and fourth procedures, calculation of $P_{ABS}(\chi_{Test}|G_A)$ and $P_{BAYES}(\chi_{Test}|G_A)$, provide two methods for classifying signals within the library. These methods only consider the problem of classification of a test signal amongst previously specified groups.

The first statistical calculation examined two groups and addressed the question, what is the probability that the two groups are the same? For example, where the library has a set of K groups and there are $N_A, N_B, \ldots N_K$ signals in each group, Z dynamical measures are calculated for each signal in each group. The motivating question can now be stated with greater precision. Given these signals and these dynamical measures, what is the probability that two groups in the library, denoted Group A and Group B, are the same? This probability is denoted by $P_{SAME}(G_A, G_B)$.

$\hat{\mu}_A$ is the Z-dimensional vector containing the average values of the discriminating variables using members of Group A.

$$\hat{\mu}_A = (\hat{\mu}_{A1}, \hat{\mu}_{A2}, \ldots, \hat{\mu}_{AZ})$$

$$\hat{\mu}_{Ai} = \frac{1}{N_A} \sum_{m=1}^{N_A} x_i(m)$$

where $x_i(m)$ is the mth value of discriminating variable i in Group A. $(\sigma_A^2)_{i,j}$ is element (i, j) of the Group A covariance matrix.

$$(\sigma_A^2)_{i,j} = \frac{1}{N_A - 1} \sum_{m=1}^{N_A} (x_i(m) - \hat{\mu}_{Ai})(x_j(m) - \hat{\mu}_{Aj})$$

$\Sigma_A$ denotes the $Z \times Z$ matrix of elements $(\sigma_A^2)_{i,j}$. $\Sigma_A^{-1}$ denotes its inverse. These variables are defined analogously for Group B. $(\sigma_{A,B}^2)_{i,j}$ is element (i, j) of the between-Group covariance matrix for Groups A and B.

$$(\sigma_{A,B}^2)_{i,j} = \frac{(N_A - 1)(\sigma_A^2)_{i,j} + (N_B - 1)(\sigma_B^2)_{i,j}}{N_A + B_B - 2}$$

$\Sigma_{A,B}$ denotes the matrix formed by these elements, and $\Sigma^{A,B,-1}$ is its inverse. The between-group Mahalanobis distance, $D_{A,B}^2$, is defined by $$D_{A,B}^2 = \begin{pmatrix} \hat{\mu}_{A1} - \hat{\mu}_{B1} \\ \hat{\mu}_{A2} - \hat{\mu}_{B2} \\ \vdots \\ \hat{\mu}_{AZ} - \hat{\mu}_{BZ} \end{pmatrix}^T \sum_{A,B}^{-1} \begin{pmatrix} \hat{\mu}_{A1} - \hat{\mu}_{B1} \\ \hat{\mu}_{A2} - \hat{\mu}_{B2} \\ \vdots \\ \hat{\mu}_{AZ} - \hat{\mu}_{BZ} \end{pmatrix}$$

The probability that the two groups are the same is given by an F-test.

$$P_{SAME}(G_A, G_B) = I_{\frac{v_2}{v_2 + v_1 F}}\left(\frac{v_2}{2}, \frac{v_1}{2}\right)$$

where $v_1 = Z$, the number of discriminating variables, is the number of degrees of freedom in the numerator, and $v_2 = N_A + N_B - Z - 1$, is the degrees of freedom in the denominator.

$$F = \frac{N_A N_B \lfloor (N_A + N_B - Z - 1) D_{A,B}^2 \rfloor}{(N_A + N_B)(N_A + N_B - 2)Z}$$

$I_x(a,b)$ is the incomplete $\beta$ function.

$$I_x(a, b) = \frac{1}{B(a, b)} \int_o^x t^{a-1}(1-t)^{b-1} dt$$

and $B(a,b)$ is the beta function $$B(a, b) = \int_0^1 t^{a-1}(1-t)^{b-1} dt$$

which is seen to be monotone decreasing with the Mahalanobis distance. From the numerator of F, it is seen that $N_A + N_B > Z + 1$ is an absolute requirement of the analysis.

The sensitivity of $P_{SAME}(G_A, G_B)$ to the choice of dynamical measures should be explicitly recognized. The failure to reject the null hypothesis does not mean that it will invariably be impossible to distinguish between the two groups. This remains an open question because it is always possible that the introduction of additional measures will result in a statistically significant discrimination.

Use of $P_{ERROR}$ is an additional desirable characterization/classification tool. It is sometimes supposed that if $P_{SAME}$ is small, then the dynamical measures provide an effective means of classifying the signals between groups. This is not necessarily the case. A small value of $P_{SAME}$ is desirable for discrimination, but it is not always sufficient. If the distributions of the two groups overlap, it is possible for $P_{SAME}$ to be small even though there is a high error rate when signals are classified.

A more immediately pertinent measure of discrimination is $P_{ERROR}$ $(G_A, G_B)$ which is the probability of an error in pairwise discriminations between the two groups. A precise definition of $P_{ERROR}$ $(G_A, G_B)$ can be expressed in terms of a minimum Mahalanobis distance classification criterion. Suppose a test signal is selected at random from either Group A or Group B. Let $\chi$ Test be the Z-dimensional vector of dynamical measures obtained from the test case.

$$\chi\text{Test} = (\chi 1\text{-Test}, \chi 2\text{-Test}, \ldots, \chi Z\text{-Test})$$

The Mahalanobis distance between $\chi$Test and Group A, denoted $D_{Test,A}^2$, is given by:

$$D_{Test,A}^2 = \begin{pmatrix} x_{1-Test} - \hat{\mu}_{A1} \\ x_{2-Test} - \hat{\mu}_{A2} \\ \vdots \\ x_{z-Test} - \hat{\mu}_{AZ} \end{pmatrix}^T \sum_A^{-1} \begin{pmatrix} x_{1-Test} - \hat{\mu}_{A1} \\ x_{2-Test} - \hat{\mu}_{A2} \\ \vdots \\ x_{z-Test} - \hat{\mu}_{AZ} \end{pmatrix}$$

where $\hat{\mu}_A$ and $\Sigma_A$ are as previously defined. $D_{Test,B}^2$ is defined analogously for Group B. Under this criterion $\chi$Test will be deemed to be a member of the group corresponding to the smaller Mahalanobis distance. $P_{ERROR}(G_A, G_B)$ is the overall error rate of this pairwise discrimination. Mahalanobis has shown that $P_{ERROR}$ can be approximated by $$P_{ERROR}(G_A, G_B) = 1 - \Phi\left(\frac{\sqrt{D_{A,B}^2}}{2}\right) = \Phi\left(-\frac{\sqrt{D_{A,B}^2}}{2}\right)$$

As in the case of $P_{SAME}$, the Mahalanobis distance is calculated using the between-group covariance matrix. $\Phi$ is the cumulative normal distribution.

$$\Phi(x) = \frac{1}{\sqrt{2\pi}} \int_{-\infty}^x e^{-u^2/2} du - \frac{1}{2}\left[1 + \text{erf}\left(\frac{x}{\sqrt{2}}\right)\right]$$

where erf is the error function.

$$\text{erf}(x) = \frac{2}{\sqrt{2\pi}} \int_o^x e^{-t^2} dt$$

Figure 4:
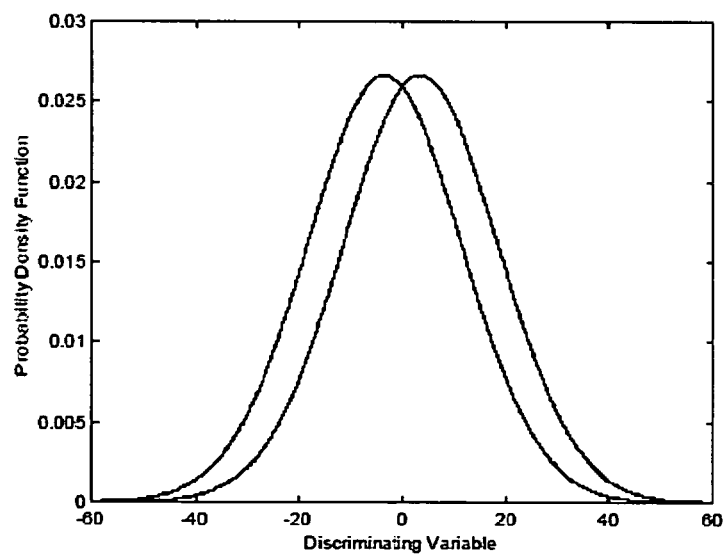
FIG. 4 is a graph illustrating two normal distributions in which $P_{SAME}$ is low ($P_{SAME}=3.2\times10^{-13}$) and $P_{ERROR}$ is high ($P_{ERROR}=0.32$).

A numerical example of the distinction between $P_{SAME}$ and $P_{ERROR}$ is illustrated in the graph of FIG. 4 which shows two normal distributions in which $P_{SAME}$ is low and $P_{ERROR}$ is high.

Consider the case where a single discriminating variable (Z=1) is used in a pairwise discrimination between Group A and Group B. The mean value of the discriminating variable in Group A is $\hat{\mu}_A$, and its variance is $\sigma_A^2$. $\hat{\mu}_B$ and $\sigma_B^2$ are defined analogously. For a one-dimensional discrimination, the between-group covariance is a single element.

$$(\sigma_{A,B}^2) = \frac{(N_A - 1)\sigma_A^2 + (N_B - 1)\sigma_B^2}{N_A + N_B - 2}$$

The corresponding Mahalanobis distance for the Z=1 case is given by $$D_{A,B}^2 = \frac{(\hat{\mu}_A - \hat{\mu}_B)^2}{\sigma_{A,B}^2}$$

This expression for $D_{A,B}^2$ can be used in the previously presented expressions for $P_{SAME}$ and $P_{ERROR}$. It is possible to produce cases in which $P_{SAME}$ is small while $P_{ERROR}$ approaches the maximum possible error rate in a pairwise discrimination of $P_{ERROR}=0.5$. This correlates with the graph of FIG. 4 where $P_{SAME}=3.2*10^{-13}$, $P_{ERROR}=0.32$, $\hat{\mu}_A=-3.5$, $\hat{\mu}_B=3.5$, $\sigma_A=\sigma_B=15$ and $N_A=N_B=500$.

Classification was performed by calculation of a priori membership probabilities. The minimum Mahalanobis distance classification criterion presented in the definition of the pairwise $P_{ERROR}$ generalizes to an arbitrary number of groups. In a library of K groups, the test signal is classified into Group J if $$D_{Test,J}^2 = \min(D_{Test,I}^2, I=1, 2, \ldots, K)$$

However, it is also important to estimate the confidence of a classification.

One way to estimate the confidence of a classification is to calculate the probability that $\chi_{Test}$ is an element of the distribution formed by members of Group A. Informally, this is the probability that $\chi_{Test}$ is a member of Group A. This probability is denoted by $P_{ABS}(\chi_{Test}|G_A)$, where 'ABS' in $P_{ABS}$ indicates that this is the absolute or a priori probability. The probability $P_{ABS}(\chi_{Test}|G_A)$ is given by:

$$P_{ABS}(x_{Test}|G_A) = I_{\frac{v_2}{v_2=v_1F}}\left(\frac{v_2}{2}, \frac{v_1}{2}\right)$$

where $v_1=Z$ is the number of discriminating variables. $v_2=N_A-Z$, here $N_A$ is the number of members in Group A and F is given by $$F = \frac{N_A(N-Z)D_{Test,A}^2}{(N_A^2-1)Z}$$

As before, $I_x(a,b)$ is the incomplete beta function, and $B(a,b)$ is the beta function. It is seen that this is equivalent to $P_{SAME}(G_A,G_B)$ for the special case where $$N_B=1 \text{ and } \hat{\mu}_B = \chi_{Test}$$

Calculation of Bayesian membership probabilities is an alternative classification procedure derived from Bayes' theorem. The group-specific density estimate at $\chi_{Test}$ from Group A is $$f_A(x_{Test}) = \frac{1}{(2\pi)^{Z/2}(\det \Sigma_A)^{1/2}} \exp\left\{-\frac{1}{2}\begin{pmatrix} x_{1-Test} - \hat{\mu}_{A1} \\ x_{2-Test} - \hat{\mu}_{A2} \\ \vdots \\ x_{Z-Test} - \hat{\mu}_{AZ} \end{pmatrix}^T \Sigma_A^{-1} \begin{pmatrix} x_{1-Test} - \hat{\mu}_{A1} \\ x_{2-Test} - \hat{\mu}_{A2} \\ \vdots \\ x_{Z-Test} - \hat{\mu}_{AZ} \end{pmatrix}\right\}$$

Using Bayes' theorem, the posterior probability of $\chi_{Test}$ belonging to Group A is:

$$P_{BAYES}(x_{Test}|G_A) = \frac{P'_A f_A(x_{Test})}{\sum_{M=1}^{K} P'_A f_M(x_{Test})}$$

where $P'_M$ is the prior probability of membership in Group M. $\ddot{x}_{Test}$ is deemed to be a member of the group corresponding to the maximum value of $P_{BAYES}$ When calculating $P_{SAME}(G_A,G_B)$ and $P_{ERROR}(G_A,G_B)$, the Mahalanobis distance calculated with $\Sigma_{A,B}$, the between-group covariance matrix was used. Also, $P_{ABS}$ and $P_{BAYES}$ were calculated with $D_{Test,A}^2$ which was computed using $\Sigma_A$, the Group A covariance matrix. An alternative practice particularly favored in the earlier literature replaces $\Sigma_{A,B}$ and $\Sigma_A$ with $\Sigma_{Pool}$, the pooled covariance matrix computed using all K groups $$\sigma_{Pool}^2 = \frac{(N_A-1)\sigma_A^2 + (N_B-1)\sigma_B^2 + \cdots + (N_K-1)\sigma_K^2}{N_A + N_B + \cdots + N_K - K}$$

When compared against computations performed with $\Sigma_{Pool}$, we found a lower incidence of classification error with our test signals using $\Sigma_A$ computed separately for each group. All of the results presented in FIGS. 3-18 were obtained by separately computed $\Sigma_{A,B}$ and $\Sigma_A$ matrices. An examination of the expressions for $P_{ABS}(\chi_{Test}|G_A)$ and $P_{ABS}(\chi_{Test}|G_A)$ indicates that if $\Sigma_A$ is replaced by $\Sigma_{pool}$, then the same classifications are obtained with minimum Mahalanobis distance and with maximum Bayesian likelihood criteria. In the computations using our signal library, the results are usually the same. Operationally, both classifications were computed and disagreements between the methods and the accompanying low membership probabilities were used as a warning of uncertainty in the classification.

4. Classification Results

Detailed tabulated representations of the results are provided in FIGS. 5a–5p. FIG. 5a is a table illustrating the probability that two groups are the same, zero noise case, average $P_{SAME}=0.174\times10^{-6}$. FIG. 5b is a table illustrating the probability of errors in a pairwise discriminations, zero noise case average $P_{ERROR}=0.155\times10^{-3}$. FIG. 5c is a table illustrating a classification matrix, minimum Mahalanobis distance criterion, zero noise case, percent incorrect=0%. FIG. 5d is a table illustrating a classification matrix, maximum Bayesian likelihood criterion, zero noise case, percent incorrect=0%. FIG. 5e is a table illustrating the probability that two groups are the same, SNR=10 dB, average $P_{SAME}=0.718\times10^{-4}$. FIG. 5f is a table illustrating the probability of errors in a pairwise discrimination, SNR=10 dB, average $P_{ERROR}=0.263\times10^{-2}$. FIG. 5g is a table illustrating a classification matrix, minimum Mahalanobis distance criterion, SNR=10 dB, percent incorrect=2.2%. FIG. 5h is a table illustrating a classification matrix, maximum Bayesian likelihood criterion, SNR=10 dB, percent incorrect=1.1%. FIG. 5i is a table illustrating the probability that two groups are the same, SNR=5 dB, average $P_{SAME}=0.0006$. FIG. 5j is a table illustrating the probability of errors in a pairwise discrimination, SNR=5 dB, average $P_{ERROR}=0.0130$. FIG. 5k is a table illustrating a classification matrix, minimum Mahalanobis distance criterion, SNR=5 dB, percent incorrect=4.4%. FIG. 5l is a table illustrating a classification matrix, maximum Bayesian likelihood criterion, SNR=5 dB, percent incorrect=4.4%. FIG. 5m is a table illustrating the probability that two groups are the same, SNR=0 dB, average $P_{SAME}$=0.0381. FIG. 5n is a table illustrating the probability of errors in a pairwise discrimination, SNR=0 dB, average $P_{ERROR}$=0.0520. FIG. 5o is a table illustrating a classification matrix, minimum Mahalanobis distance criterion, SNR=0 dB, percent incorrect=20%. FIG. 5p is a table illustrating a classification matrix, maximum Bayesian likelihood criterion, SNR=0 dB, percent incorrect=21%.

Since there were nine groups in this example, the expected classification error rate based on random assignment was 89%. The observed within-library classification error rates at each noise level are presented in Table 1.

TABLE 1

Within-Library Classification Errors - Nine Groups, Including Stochastic Signals.

| | Error rate expected | Error rate minimum Mahalanobis distance | Error rate maximum Bayesian Likelihood |
|---|---|---|---|
| Clean Data | 89% | 0% | 0% |
| SNR = 10 dB | 89% | 2.2% | 1.1% |
| SNR = 5 dB | 89% | 4.4% | 4.4% |
| SNR = 0 dB | 89% | 20% | 21% |

In the case of clean data there was a statistically significant separation between all groups. The average value of $P_{SAME}$ is $0.174 \times 10^{-6}$. The largest single contribution was $P_{SAME}$=$0.6 \times 10^{-5}$. The probabilities of errors in pairwise discriminations were also low. The average value of $P_{ERROR}$ was $0.155 \times 10^{-3}$ and the largest single value was $0.6 \times 10^{-2}$. No classification errors were made using either minimum Mahalanobis distance or maximum Bayesian likelihood as the classifying criterion when clean time series were examined. Also, the confidence of the classification was high. In the case of correct classifications, $P_{ABS}$ is 0.797 and the average value of $P_{BAYES}$ is 0.999. As shown in FIGS. 5c and 5d, these measures were able to discriminate successfully between uniformly and normally distributed random numbers. This discrimination cannot be achieved with spectral measures.

The introduction of additive noise to SNR=10 dB results in two classification errors when the minimum Mahalanobis distance was the classification criterion (Error Rate=2.2%) and one classification error (Error Rate=1.1%) when the maximum Bayesian likelihood was used to classify the signals. At this noise level, the average value of $P_{SAME}$ was $0.718 \times 10^{-4}$ with a maximum value of $0.3 \times 10^{-2}$. The average predicted error rate in pairwise discriminations was $\langle P_{ERROR} \rangle = 0.263 \times 10^{-2}$ with a maximum value of 0.0742.

When the noise level was increased to SNR=5 dB, the average value of $P_{SAME}$ is 0.0006, with a maximum value of 0.0154. This maximum value was obtained when filtered, uniformly distributed random numbers were compared against filtered, normally distributed random numbers. One would expect this distinction to be obscured by additive normally distributed noise. The same pattern was observed when the values of $P_{ERROR}$ were examined. At this noise level, $(P_{ERROR})$=0.0130, and again the maximum value $(P_{ERROR}$=0.1229) was obtained when filtered, uniformly distributed noise was compared with filtered, normally distributed noise. At SNR=5 dB, there was a 4.4% classification error when the minimum Mahalanobis distance criterion was used compared to the expectation rate of 89%. The observed error rate was also 4.4% when the maximum Bayesian likelihood was used to classify signals.

When the variance of added noise was equal to the variance of the original signal (SNR=0 dB), the classification error rate was approximately one quarter of the expectation rate of 89%. When the minimum Mahalanobis distance criterion was applied, the error rate was 20%. When the Bayesian maximum likelihood was the assignment criterion, the error rate was 21%. The average value of $P_{SAME}$ was 0.0381, and the average value of $P_{ERROR}$ was 0.0520. In operational terms, however, the system's performance was better than these numbers alone would suggest. A disagreement between a minimum Mahalanobis distance classification and a Bayesian likelihood classification provided a warning of an uncertain classification. Also, for any given test case, low values of $P_{ABS}$ and $P_{BAYES}$ provided an indication of reduced confidence. The average values of $P_{ABS}$ and $P_{BAYES}$ in the case of correct classifications are shown in Table 1. The case by case probabilities are presented by FIGS. 5a–5p.

The results reflect that most classification errors occur when stochastic signals that have been obscured by high levels of additive noise are misclassified into an incorrect stochastic signal group. For example, at SNR=0 dB, four errors (out of ten test cases) occur when a time series obtained by adding normally distributed noise to uniformly distributed random numbers was classified as belonging to the group consisting of normally distributed random time series. This was not surprising since at SNR=0 dB the test case was composed by adding equal elements of each signal category. At high noise levels a more valid measure of the system's robustness is obtained when only deterministic signals are considered.

Table 2 shows the results obtained from a four-group study consisting of the van der Pol oscillator and the Lorenz, Rössler and Hénon attractors.

TABLE 2

Within-Library Classification Errors - Four Groups, Deterministic Signals only.

| | Error rate expected | Error rate minimum Mahalanobis distance | Error rate maximum Bayesian Likelihood |
|---|---|---|---|
| Clean Data | 75% | 0% | 0% |
| SNR = 10 dB | 75% | 0% | 0% |
| SNR = 5 dB | 75% | 0% | 0% |
| SNR = 0 dB | 75% | 2.5% | 2.5% |

When the classification was limited to four groups of deterministic systems, no errors occurred with clean data, at SNR=10 dB or at SNR=5 dB. A single error occurred at SNR=0 dB.

The results in Tables 1 and 2 illustrate that the classification system shows a capacity to discriminate between dynamical systems, and that it is robust to additive noise. The number of cases in a group determines the accuracy of the within-group average value estimates. These numbers appear in the equation specifying the Mahalanobis distance. Additionally, the number of cases in each group has an impact on the determination of the covariance matrix and its inverse. If the number of members in a reference group is too low, the inverse of the within-group covariance matrix is adversely affected.

The introduction of additional dynamical measures can be provided. The identification of appropriate measures is not a question with a single answer. Dynamical measures useful in one classification problem may be nondisclosing in another. For example, the measures that can successfully discriminate between classes of waveform data may not be particularly helpful when inter-event interval data are to be classified.

By definition the performance obtained in the nine-group and four-group classification of this example is the worst case for this signal library. If the introduction of an additional measure does not improve performance, it does not have to be incorporated into the system. The question: "Is a given dynamical measure helpful?" can be resolved mathematically. As noted above, the contribution of each dynamical measure can be determined by first calculating the partial F-value associated with each variable and then eliminating those variables with small partial F-values.

As indicated in the introduction, signal classification has been applied in medical diagnosis, for example the differential diagnosis of neuropathies and myopathies and in clinical monitoring. Psychiatric diagnosis based on EEGs and ERPs has received significant effort and has generated a large literature. Prediction of treatment outcome is a pressing problem in all areas of medicine and most particularly in psychiatry. Early classification between groups of treatment responders and nonresponders is valuable. Examples of outcome prediction based on electroencephalographic measures include the use of acute challenge ERPs as a prognostic of response/nonresponse to methylphenidate treatment of attention deficit-hyperactivity disorder and the analysis of EEGs and the prediction of treatment outcome for cocaine dependent males.

The example presented here provides a dynamical and statistical methodology that is applicable to a broad range of problems. To an approximation, applied dynamical analysis addresses four problems: signal classification, detection of change, prediction and optimal control of dynamical behavior. This example specifically addresses the first problem but generalizations to the remaining three problems can be constructed on this foundation. Detection of change is the central problem of smart alarm technology and is particularly important in medical applications. Detection of change can be addressed by treating the Mahalanobis distance as a function of time. The distance of the signal's immediate past from preceding observations or from a standardized baseline can be calculated. For example, this example can be used to create a procedure to detect seizure onset and termination based on electroencephalographic and/or cardiovascular variables. The problem of detecting change is closely related to the problem of prediction. This example shows that one can use the time-dependent Mahalanobis distance to predict changes in dynamical behavior. Prediction based on the time-dependent Mahalanobis distance has a significant advantage over conventional methods based on a single dynamical measure, because this method provides a systematic statistical procedure for optimally combining several complementary dynamical measures and for combining different classes of observed variables. For example, a combination of electroencephalographic and cardiovascular variables can be used to define a set of groups in a library for a single type of discrimination classification.

A further application of dynamical analysis is system control. For example, dynamical diseases are disorders that result from parameter-dependent bifurcations in physiological control systems. An intervention to a dynamical disease is constructed by altering accessible system parameters, usually with medication, until acceptable dynamical behavior is restored. A response is optimal if this restoration is achieved in a minimum time with a minimum intervention, the smallest pharmacological impact. Through application of the present invention, it is possible to introduce multiple dynamical measures into this process by incorporating the Mahalanobis distance into the objective function.

EXAMPLE 2

Identification of Seizure Termination in Generalized Tonic-Clonic Seizure EEG Data A procedure was developed for identifying one particular transition, the end-point of seizures in two-channel electroencephalographic data recorded during generalized tonic-clonic seizures. Data from twenty-eight seizures were available and used to develop and test the procedure in terms of the agreement between the computationally identified seizure end-point compared against the ratings of an expert clinical electroencephalographer. Generalizations to multivariate seizure onset detection and to seizure prediction are described.

The procedure detected transitions in physiological time series. The particular time series were electroencephalographic (EEG) data recorded during generalized tonic-clonic seizures. The procedure was developed in order to achieve maximal agreement with an expert EEG rater in the identification of the point at which the seizure ends. There is clinical relevance to the determination of the seizure end-point in this type of data.

Segmentation methods began by subdividing the time series into epochs of a predetermined size. These epochs were then characterized using one of several candidate measures. The value of the candidate measure for an epoch of interest was compared with the values derived from previous epochs. If this comparison indicated that the change in the candidate measure exceeded a predetermined threshold, the result was identified as the point where a transition occurred in the time series. Thus, the procedure can be characterized as a series of binary decisions (transition or no-transition) based on a series of single numbers which are indices of the degree of change of the candidate measure for an epoch of interest with the measure derived from the prior epochs.

Candidate measures were chosen based on experience with the particular application at hand and the type of transition that it was desired to identify. Consideration was given to both linear and nonlinear methods since their attributes differ. The advantages of the linear methods are that they are generally computationally economical, easy to implement, and well suited to characterizing a time series. A disadvantage is that they are usually statistical in nature and therefore insensitive to information which can be gained from the dynamical structure of the time series.

Many nonlinear methods begin with a time delayed embedding of the data. If properly constructed, the embedding reproduces many of the dynamical properties of the original system. Changes in the dynamical behavior of a system will be reflected by a change in the geometry of the embedded time series. For example, let $(V_1, V_2, V_3, \ldots)$ denote successive measurements obtained from the dynamical system of interest. Symbol V is used to denote the observational data since, in this example, the observed variables are voltages. These scalar values are used to construct a set of points $\{X_i\}$ in m-dimensional space by embedding the original data.

$$X_i = (V_i, V_{i+L}, V_{i+2L}, \ldots V_{i+(m-1)L})$$

The parameter m is the embedding dimension and parameter L is the lag. The analysis continued with an examination of the geometry of set $\{X_i\}$. There were several measures available that could be used to characterize the geometry of a cloud of points in m-dimensional space. A difficulty associated with the application of nonlinear measures, was choosing proper embedding criteria. The use of a candidate measure or a set of candidate measures to separate data into epochs where transitions had occurred and to epochs where no transition had occurred was a simple two-state discrimination task.

There are a number of techniques which can be used to assess the capacity for measures to accomplish this discrimination and to determine optimal coefficients for making the discrimination. Among the simplest and most popular are discriminant analysis and logistic regression. These techniques employ linear or nonlinear combinations of candidate measures to compute a likelihood that a transition has taken place. Techniques which minimize squared error are used to calculate the coefficients of the terms in the linear combinations which will achieve the best separation of groups. The capacity of candidate measures to perform this separation forms the basis of a method for detecting transitions. Without a high capacity for discrimination, performance can be extremely poor as can easily be seen in a simple analysis.

The probability of success in the process of sequentially assessing whether a transition has occurred or not in a series of epochs can be approximated as a classic independent Bernoulli trial, examples of which are a series of coin tosses or rolls of dice. The probability that in analysis of n epochs of data, a method will have k successes and n–k failures is given by:

$$P(n, k, s) = \binom{n}{k} s^k (1-s)^{n-k}$$

where s is the probability for success for each epoch and f is the probability of failure (f=1−s). For the idealized situation where a measure can achieve perfect discrimination between epochs with and without transitions, s=1 and k=n for each epoch. In this case P(n, k, s)=1 no matter how many epochs are tested. In the case of sequential trials, a simpler relationship applies. Here the probability of n consecutive trials being correct is given by $P(n)=s^n$, where s is the probability of success for each epoch. Sustained success is highly unlikely because its probability decays exponentially with the number of epochs. The probability of any kind of sustained success rapidly decreases as s degrades from 1.0 due to measure weakness or noisy data. Even with an excellent measure, say one that has a 95% accuracy (s=0.95), there is only a 49% chance of making the correct discrimination for twelve consecutive epochs.

In many applications, however, even though accurate epoch-by-epoch discrimination may not have occurred, the performance may still be satisfactory. This can occur when a transition is detected in an epoch that is close enough to the true transition epoch that the detection is useful. Allowing success to include a multiple epoch window around the true transition greatly increases the effective success rate of the procedure. If one assumes that there is one transition in a series of n epochs studied and allows a q epoch success window on either side of the transition, the probability of achieving sustained success is substantially increased as it is approximated by the following equation:

$$p(n) = \{1 - sf^{2q}\} s^{(n-2q-1)}$$

With a measure of an accuracy of 95%, for twelve epochs, using a success window of three epochs on both sides of the actual transition increases the likelihood of success to approximately 75%.

Another approach is to treat the estimate of the epoch at which the transition occurred as a continuous variable. This amounts to assigning a time value to the identified epoch, such as the midpoint of the epoch. In this case, model performance is assessed by comparisons of the transition time estimates of the model and of the actual transition times. A number of techniques have been used for this purpose, including correlation, intra-class correlation (correlation corrected for the degree of chance agreement), and the sum of the squared difference between the ratings. While the transition time estimates are treated as continuous variables, the error is still dependent on epoch-by-epoch dichotomous transition determinations. The probability of success within q epochs is given by above equation. Converting q to the continuous variable, time, by a method such as using the epoch midpoint, this equation can be used to estimate the expected degree of error in the continuous case by computing q for particular values of accuracy (s and t), number of epochs, n, and a probability of confidence that the error will be q or less. Examination of this equation indicates that, for a given confidence level, frequently chosen to be 95%, larger errors are associated with larger number of epochs examined, and lower accuracy. However, the dependence on these factors is not simple.

Another way in which the performance of a procedure may be improved in practice is the incorporation of estimates of the relative risks associated with particular types of errors in identifying transitions. Certain types of errors are antagonistic, that is, increasing the likelihood of one will decrease the likelihood of the other. For sequential segmentation-based transition detection, an antagonism exists between premature identification of a transition and late identification. For some applications it may be much more problematic if the procedure identifies a transition before an actual transition has occurred than if no transition is identified. In other applications the reverse will be true. The way this information may be incorporated into the procedure is by adjusting the threshold to decrease the likelihood of the most undesirable outcome.

For a situation where a known transition occurs after t epochs without transitions, an increase in the threshold for identifying transitions will increase the likelihood that no transition will be identified prior to epoch t and decrease the likelihood that the transition will be detected. A threshold, T can be defined which reflects these relative risks as follows:

$$T = (P_{n,n} R_t) / (P_{n,n} R_t + P_{n,t} B_t)$$

In this equation, $P_{n,n}$ is the probability that an epoch without a transition will be correctly identified as having no transition, $P_{n,t}$ is the probability that an epoch with a transition will not be detected, $B_t$ is the utility of correctly identifying a transition, and $R_t$ is the risk of identifying a transition prematurely. $B_t$ and $R_t$ are assigned values from 0 to 1 based on the subjective perceived benefits and risks. A high value for $B_t$ prioritizes detecting any transition that is present and decreases the threshold, whereas a high value for $R_t$ relatively prioritizes not identifying a transition prematurely and commensurate with this priority leads to a relatively higher threshold, i.e. closer to 1.

There are competing factors which should be considered in defining the size of the epoch. Firstly, different candidate measures used to detect transitions may differ in their requirements for minimum epoch size. For example, with dynamical measures the epoch size needs to be large enough to reconstruct adequately the system's attractor.

For linear statistical measures the epoch should be large enough to allow a reasonable estimate of the parameter of interest. Another consideration is that for a real-time algorithm, an epoch size which is too large limits how quickly the knowledge of identified abrupt changes is available. As reflected above, the smaller the epoch size used, the greater is the likelihood that an error will occur given the same degree of accuracy in identifying transitions. All of these factors are preferably considered and optimized for each application.

Similarly, there are competing considerations in the choice of step size, which is the time period between the start of subsequent epochs. The size of the epoch shift defines an upper limit on the average accuracy of each measure. Even with a perfect candidate measure, the difference between the actual and estimated seizure termination can range from zero seconds to the length of the epoch shift. The larger the epoch shift the larger this average error. Epoch shifts which are too small are also troublesome. As the length of the epoch shift becomes shorter than the epoch size, the number of common elements between successive epochs increases. Therefore, as the epoch shift decreases, the sensitivity requirement of the candidate measure increases. The same consideration as using a small epoch size also applies in terms of increasing the likelihood of errors.

Accordingly, both theoretical and practical considerations were used in the development of a segmentation-based procedures to detect transitions in the dynamical systems. These included the choice of candidate measures, the choice of the decision threshold, the epoch size, and the step size.

In this example, EEG data were derived from twenty-eight subjects who received electroconvulsive therapy (ECT) at Duke University Medical Center for the treatment of major depression. Informed consents were obtained from each patient. The ECT procedures involved administering short-acting barbiturate anesthesia intravenous methohexital (1 mg/kg) and then achieving neuromuscular paralysis with intravenous succinylcholine (1 mg/kg). A generalized tonic-clonic seizure was then elicited with the administration of a train of brief electrical pulses. EEG data were collected from left and right prefrontal to ipsilateral mastoid sites using Ag/AgCl electrodes. A conductive gel was applied at the electrode site in order to insure a low electrode/scalp impedance. The data were digitized at 256 Hz with 12 bit accuracy using the EEGSYS system (Friends of Medical Science, Inc.). The data were manually screened for artifact by A.D.K. Seizures were only included in analysis if they were artifact-free. The end of the seizure was identified by A.D.K., a board-certified electroencephalographer, highly experienced with identifying the endpoint of generalized tonic-clonic seizures.

From a set of twenty eight seizures, fourteen were randomly chosen to be a training set and identified as e1–e14. That is, they were used to optimize the parameters for each method. The remaining fourteen, identified as t1–t14 were then used as a test set to evaluate the performance of each method.

The epoch size was fixed at 512 points (2 secs) and the step size was set equal to 50 points (~0.2 secs.). The epoch size and step size were smaller than necessary for the goals of this example. However, several candidate measures were evaluated, this restriction helped to discriminate between the different methods. Once the best candidate measures are identified, those parameters can be varied to improve performance.

Candidate measures were chosen on the basis of two considerations. The first was evidence that the amplitude of EEG tends to decrease at the time that the seizure ends. The other was the desire to include both linear and nonlinear measures as described above. Originally six methods were investigated: autocorrelation time and its first derivative, variance, standard distance, power spectrum, and a correlation integral based measure. However, two of these methods, correlation integral and variance, significantly outperformed the others. Only the results of using those methods are provided in this example which is discussed in conjunction with FIGS. 6a–9e.

The first measure considered was based on changes in the variance of successive epochs. FIGS. 6a and 6b reflect an ECT time series with clinician's indication of seizure termination and the corresponding variance measure for successive epochs, respectively. FIG. 6a is a plot of one of the original data sets along with a vertical line indicating where a clinician has determined the seizure endpoint. FIG. 6b is a corresponding plot of the value of the variance of each epoch throughout this same data set.

Generally the variance increased, or at least remained at a relatively large value, during the seizure and then decreased abruptly about the point where the seizure terminated. The resulting criterion for estimating the termination of a seizure was based on comparisons of the variance between successive epochs. As the variance of each epoch was determined, it was compared with previous values while also keeping track of the maximum value calculated up to that point in time. The seizure was deemed to have ended at the time corresponding to the midpoint of the epoch where the drop in variance exceeded the threshold value. The threshold was defined as a percentage of the maximum value. This percentage, and hence the threshold, was found by optimizing the agreement between the termination epoch as determined by the expert rater and the termination epoch determined by the algorithm. Let $R_i$ be the index of the termination epoch determined by the rater, and let $M_i$ be the index of the termination epoch determined by the algorithm. $M_i$ is a function of the threshold. Therefore, the error function is:

$$E = \{\Sigma(M_i - R_i)^2\}^{1/2}$$

where this sum is taken over the fourteen members of the training set, is also a function of the threshold. In those instances where the algorithm came to the end of the seizure record without triggering seizure termination, $M_i$ was set equal to zero, and $R_i^2$ was contributed to the sum in E.

The optimal threshold was determined by minimizing the error function with a numerical procedure. The minimization algorithm used was a one-dimensional search by the golden section method. This method began by bracketing the minimum, that is, a triplet of points, a<b<c, was identified such that f(b)<f(a) and f(b)<f(c). Therefore the function has a minimum in the interval [a, c]. Since the optimization parameter for this characteristic measure is a percentage, the global minimum lies in the interval [0, 1]. Suppose, for example, a point x is chosen either between a and b, or between b and c. To illustrate, assume x is chosen between a and b. If f(x)<f(b), then the new bracketing triplet of points becomes (a, x, b); otherwise if f(b)<f(x), then the triplet of points becomes (x, b, c). In either case the middle point of the triplet is the best minimum achieved thus far. The process is continued until |f(a)−f(c)|→0.

The second measure employed was based on the correlation integral. The correlation integral is one of the most fundamental quantities in dynamical time series analysis. It is a measure of spatial organization, and is often used to characterize the set $\{X_i\}$ formed by embedding the observed voltage data $\{V_1, V_2, \ldots\}$. The correlation integral used was defined as:

$$C(r, N, b) = \frac{2}{(N-b+1)(N-6)} \sum_{i=1}^{N-b} \sum_{j=i+b}^{N} \Theta(r - |X_i - X_j|)$$

where N is the number of points in the embedding space, b is the blind, and r is the length variable. The inclusion of a blind requires that $|i-j| \geq b$, ensuring that points which are temporally close to each other are not included in the calculation. $\Theta$ is the Heaviside function, that is, $\Theta=1$ if the argument is non-negative and 0 otherwise. For a given set $\{X_i\}$ of N embedded points, C specifies the probability that two points $X_i$ and $X_j$ are within a distance r of each other. In these calculations, the distance between vectors was given by the metric:

$$|X_i - X_j| = \max\{|V_i - V_j|, \ldots, |V_{i+(M-1)L} - V_{j+(m-1)L}|\}$$

Other distance metrics, for example, the Euclidean distance, can be used. The correlation integral is most commonly encountered in dynamical analysis in measurements of the correlation dimension. In that procedure, the correlation integral is determined as a function of r for fixed values of N and b. A search is made for a linear scaling region in the log C versus log(r) function. The slope of this scaling region is the correlation dimension. The implementation of the procedure introduced by Lerner is simpler. The value of C at a single specified value of r, $r=r^*$, is used. While this has the advantage of simplicity, it is recognized that using a single value of C means that a great deal of potentially important dynamical information has been discarded.

Figure 7A:
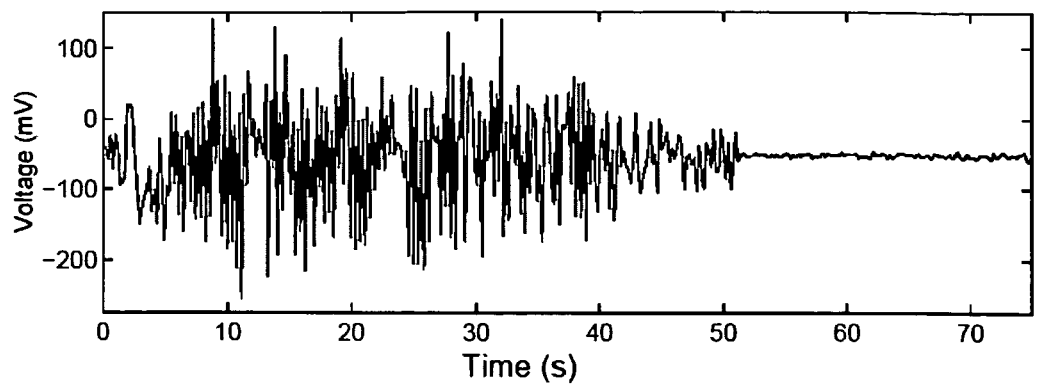
FIG. 7a is a graphic illustration of an ECT time series derived in a second example of a system constructed in accordance with the teachings of the present invention.
Figure 7B:
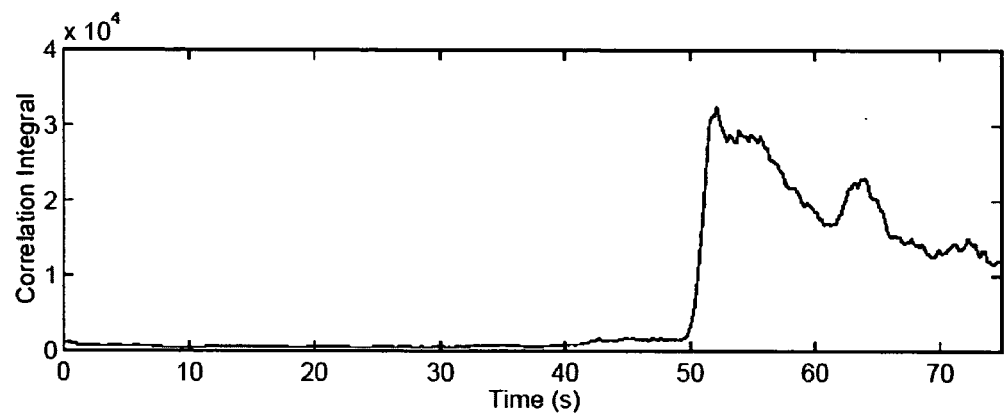

For example, FIGS. 7a and 7b illustrate an ECT time series and corresponding correlation integral measure for successive epochs, respectively. FIG. 7a shows a plot of a seizure where the termination time has been clinically determined to occur at t=51:32 secs. FIG. 7b is a corresponding plot of $C(r^*)$ as a function of time, where $r^*$ is set equal to 2% of the standard deviation of the first epoch.

Figure 8A:
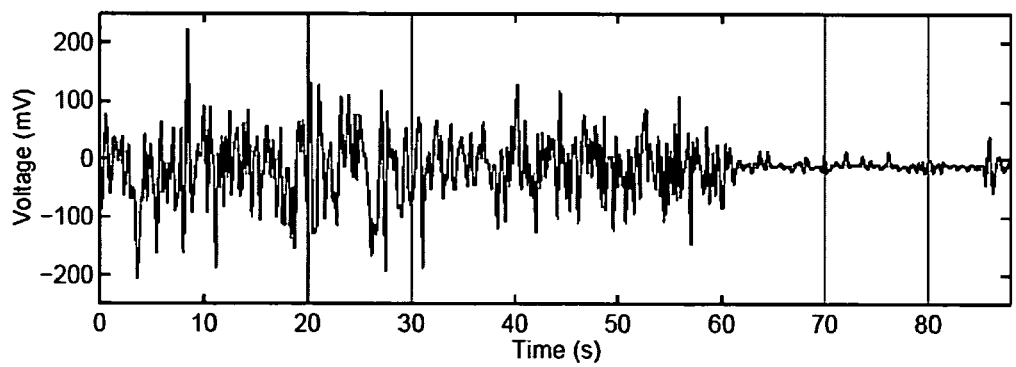
FIG. 8a is a graphic illustration of an ECT time series derived in a second example of a system constructed in accordance with the teachings of the present invention.
Figure 8B:
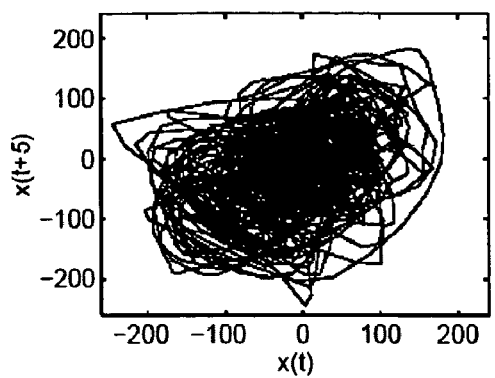
Figure 8C:
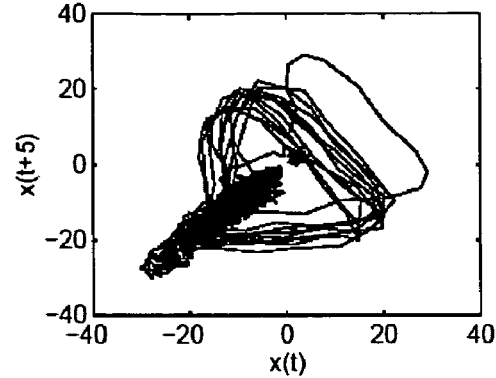

The correlation integral was generally relatively small in value during the seizure and then increased dramatically around the time that the seizure ended. The cause for this sudden change in the correlation integral becomes apparent when comparing plots of the data both during and after the seizure. FIGS. 8a–8c illustrate a plot of the original EEG time series along with two return maps, respectively. The return maps were constructed by plotting $(V_i, V_{i+k})$ pairs on an x-y plot. In the case of FIGS. 8a–8c, k=5. The FIG. 8b map is 2048 points (8 secs) beginning 20 secs into the time series, indicated by the first set of vertical lines. The FIG. 8c return map is 2048 points beginning 70 secs into the time series, indicated by the second set of vertical lines. While the return map during the seizure was large and cloud-like, or noisy in appearance, the return map after seizure termination showed much more structure and would understandably have a much larger correlation integral. There is a large difference in the scale of these return maps. Since $r^*$ was fixed, the difference in scale also contributed to a larger correlation integral after seizure termination. The criterion for estimating the termination of a seizure was based on identifying where this abrupt increase occurred. As the correlation integral was determined for an epoch at time t, the value was compared with the mean value calculated over all epochs from t=0, to t=5:859 s (30 epochs). When the value of the correlation integral for the epoch at time t exceeded a specified multiple of the average, then the seizure was deemed to have ended. As in the case of the variance threshold, that multiple was determined using the training set in the optimization calculations.

The optimization of the seizure termination threshold with the training set followed the same general outline as with the variance method. $R_i$ denoted the index of the epoch when the seizure ended as determined clinically. $M_i$ denoted the index of the seizure termination epoch computed by the algorithm. As before, the square differences of $R_i$ and $M_i$ were summed over the training set to produce the error function. The object of the computation was to find parameters that minimize this function. The optimization of parameters for the correlation integral method was more complicated for Lerner's metric than for the variance method since there was more than one parameter to be optimized. In addition to the threshold value, the values of the neighborhood size $r^*$, the embedding dimension m, and the time delay L, all were identified. The lag was fixed using the first minimum of the autocorrelation function of the first epoch. This left three parameters to be optimized. A successive univariate optimization was employed. In this type of optimization one parameter is adjusted until there is no further improvement in the objective function. The second parameter is then adjusted, and so on until each parameter has been adjusted once. In the unlikely event that the parameters are noninteracting, one cycle through this process is sufficient. However, many cycles are usually required. It was also useful to vary the sequence of parameter adjustment to offset the possibility of slowly converging cycles. Therefore beginning with m=1, the threshold value and $r^*$ were varied independently in order to identify possible minima. After these local minima were identified, the process was repeated in smaller parameter increments. This process continued until a range of parameter values producing the same results was found; the median of this range was chosen as the optimal value. Parameter m was then increased, and the process repeated until increasing the embedding dimension did not result in a significantly smaller value of E. This ensured that the smallest feasible embedding dimension was chosen. This helped reduce computational requirements.

The consideration of risks and benefits amounts to considering the risk of premature identification of seizure termination versus the risk of not identifying a seizure endpoint at all. For this application, not identifying a seizure endpoint when the seizure had actually ended (referred to as a Type 1 error) was of less concern. This would lead to the injection of anti-epileptic drugs, intended to stop a presumed ongoing seizure. The risks associated with this are very small. In contrast, if seizure termination was erroneously indicated (referred to as a Type 2 error) this could lead to an undetected prolonged seizure, which could cause substantial memory impairment and increase the risks of cardiac complications. Thus, adjustments of the threshold were made that were operationally equivalent to setting $B_t$ close to zero and $R_t$ close to one.

In the first set of calculations performed using the variance method, the threshold was determined in the previously described minimization calculation. The optimal threshold, which corresponds to the minimum of E, was 5.48%. This was the median of a range of threshold values that gave the same results. Since $M_i$ and $R_i$ are integers and not continuous variables, a range of threshold values can give the same minimum of E.

Figure 9A:
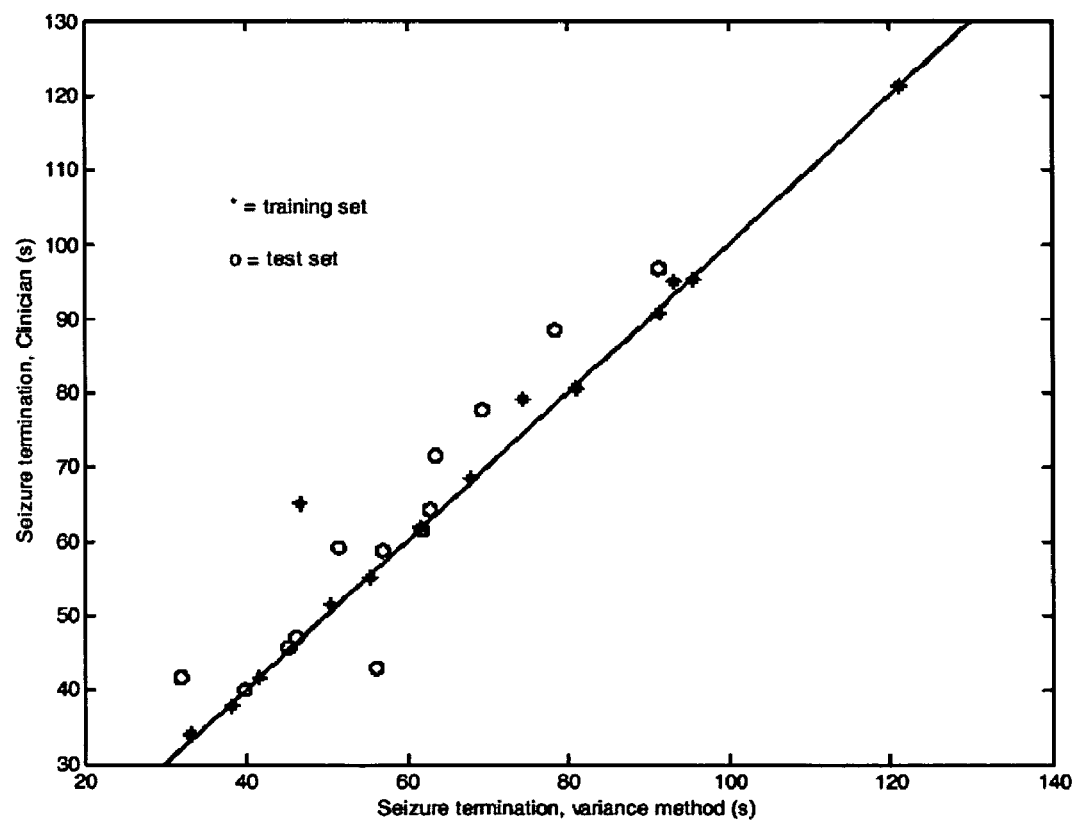
FIGS. 9a through 9e are comparative graphic illustrations showing the results obtained in the second example constructed in accordance with the teachings of the present invention.

FIG. 9a illustrates the method of variance results compared with clinician's indication of seizure termination. This Figure shows the clinically determined seizure termination times plotted against the corresponding algorithmically determined termination times. Perfect agreement between the computed and clinically seizure termination time results in a point that falls on the diagonal. Though a high degree of agreement is seen in the near diagonal result, the failure pattern is troubling. Almost all of the larger differences between the two values are examples of the premature computational indication of seizure termination. That is, the points fall above the diagonal. These are Type 2 errors. This was a potentially dangerous failure pattern.

A further examination of the error pattern was instructive. Even in those instances where there were differences between the computationally and clinically determined endpoints, the algorithm did signal seizure termination. Once the optimal threshold of 5.48% was determined, no failures to signal termination were observed. An examination of the objective function indicated why this was the case.

The function to be minimized was the error function $\{\Sigma(M^i-Ri)^2\}^{1/2}$ where $M_i$ is the computationally determined epoch where the seizure terminated. This objective function grows with the square of $M_i$. This introduced a bias to report small values of $M_i$. Unfortunately, small values of $M_i$ produce Type 2 errors. A response to this failure pattern was to modify the definition of the error function. As originally constructed, the contribution $R_i^2$ was entered into the sum for the ith term, if the algorithm did not detect the termination of the ith seizure. In subsequent calculations, a contribution of $(3 \text{ sec})^2$ was entered. After modifying the function, re-optimization resulted in a lower threshold of 1.2%.

Figure 9B:
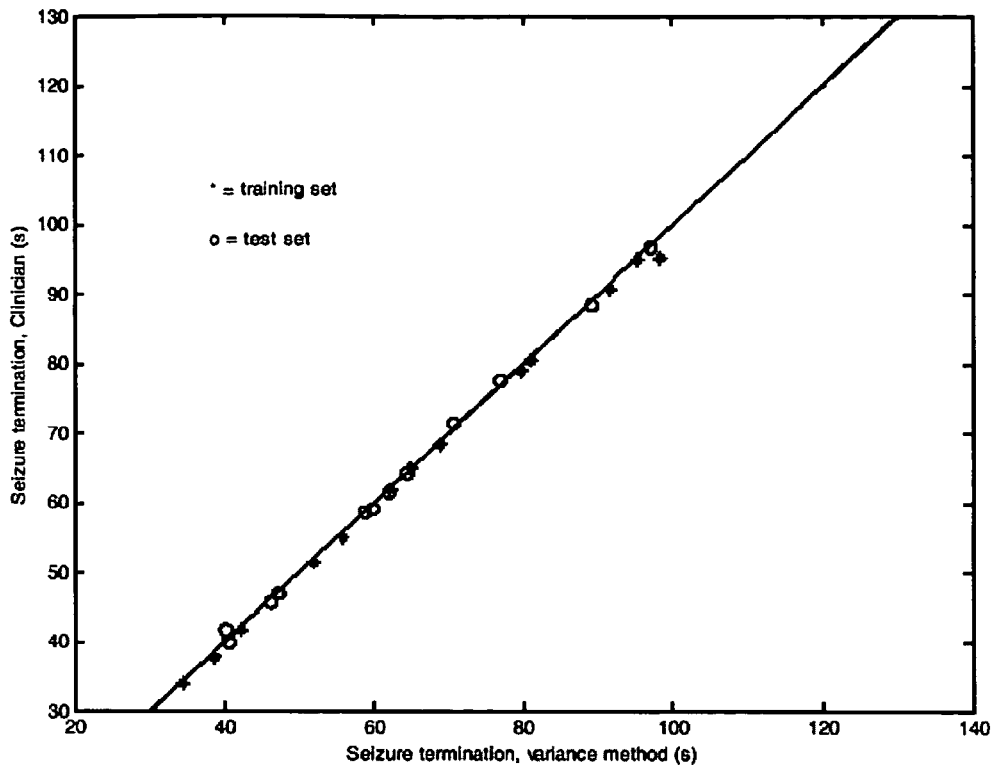

The results obtained after this modification are shown in FIG. 9b. which illustrates the method of variance results using the value of threshold found by optimizing against the training set with the revised objective function. For one seizure of the training set and two seizures of the test set, the end of the seizure was not detected. That is, three Type 1 errors (failures to detect seizure end-point) were introduced. On visual inspection of the EEGs, it was observed that these three seizures were cases where visual identification of seizure termination was most difficult. It is also noteworthy that while the modification introduced Type 1 errors, none of the seizures resulted in the premature indication of seizure termination by more than one second. Accordingly, the second optimization was less likely to produce extreme Type 2 errors.

Figure 9C:
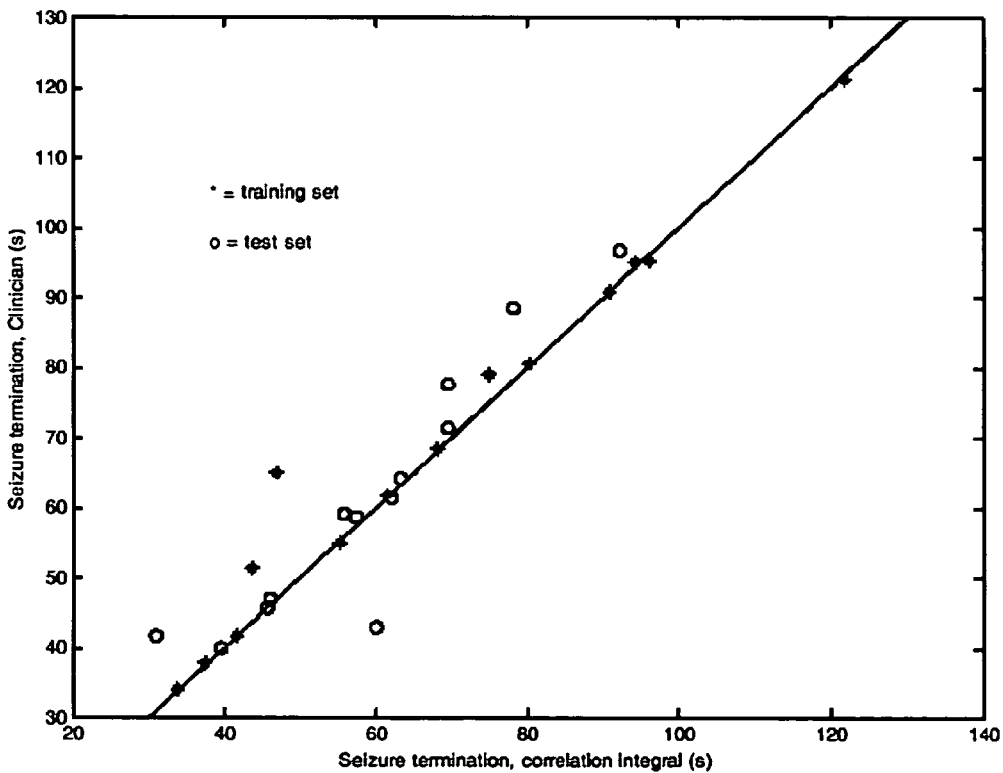
Figure 9D:
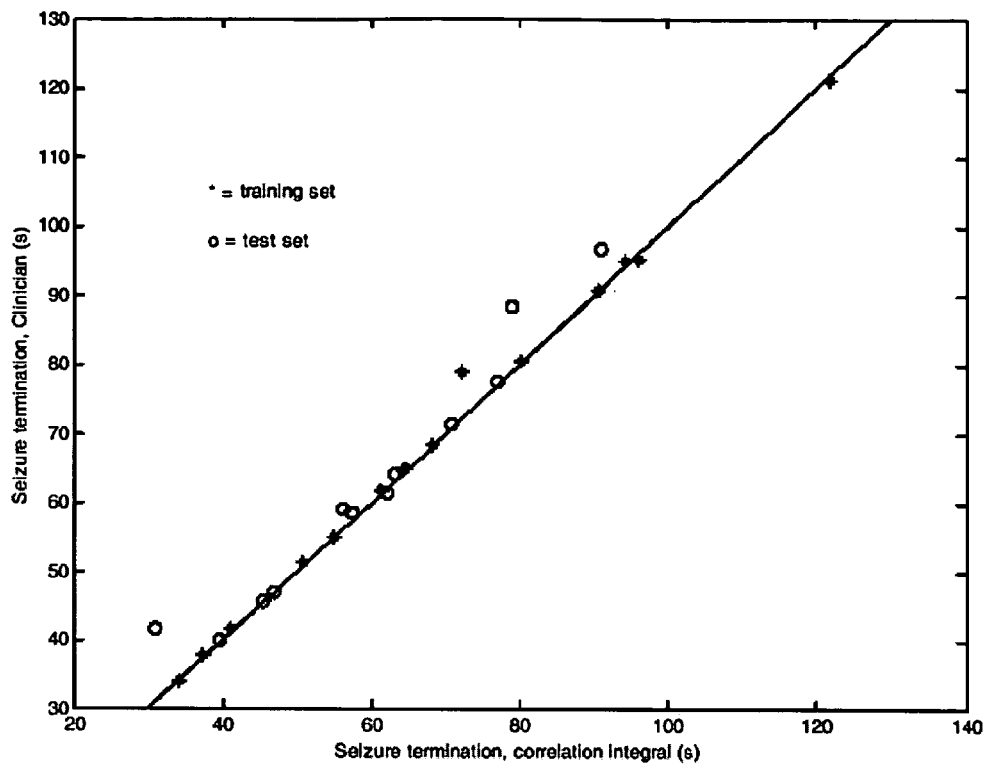

Results of testing the performance of the correlation integral method appear in FIGS. 9c and 9d that depict the results for embedding dimensions one and two, respectively. FIG. 9c illustrates the method of correlation integral results compared with clinician's indication of seizure termination, m=1, r*=0:01, and the threshold value is 2.60. The end of the seizure was not detected for one element of the test set. FIG. 9d illustrates the method of correlation integral results compared with clinician's indication of seizure termination, m=2, r*=0:02, and the threshold value is 11.00. The end of the seizure was not detected for two elements of the test set. Accordingly, dimensions higher than two did not improve the results. The findings presented in FIGS. 9c and 9d were similar to the results obtained using the method of variance. Again the majority of the errors were premature indications of seizure termination.

Figure 9E:
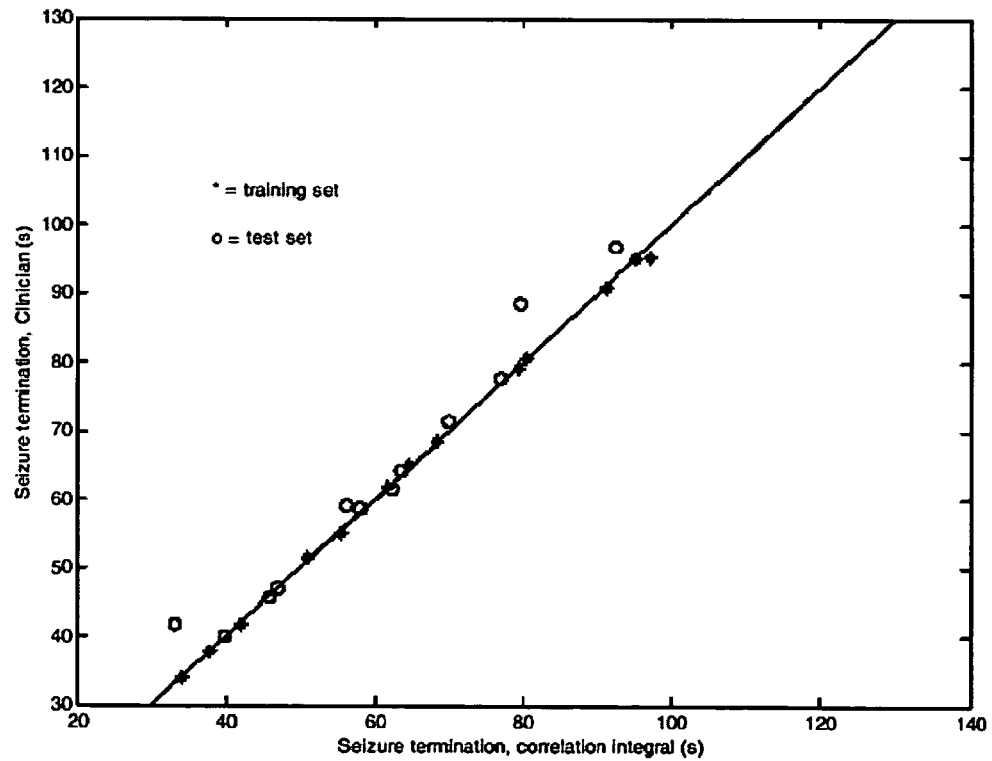

The calculations were performed again for m=1 with the modified objective function. These results are shown in FIG. 9e which illustrates the method of correlation integral results compared with clinician's indication of seizure termination using modified penalty function, m=1, r*=0:06, and the threshold value is 3.60. The end of the seizure was not detected for one element of the training set and one element of the test set. Thus, the agreement with the clinically determined ratings was improved.

This example employed the invention to achieve a high degree of agreement with an expert rater. A number of considerations were observed to effect performance including: the choice of candidate measures used, the differences between linear and nonlinear measures, the definition of successful outcomes, and the incorporation of assessments of risks and benefits of prematurely identifying transitions versus missing transitions.

In addition to considering alternative measures, performance may be improved by combining measures to produce a multivariate transition detector. As a specific example, one can consider detection of seizure onset and termination. In the case of the clinical data examined, the time of seizure onset is known because the seizures were induced artificially. The analysis can, however, also be used to detect the onset of spontaneous seizures. Assuming a baseline EEG record consisting of several epochs is available, a set of Z dynamical measures are applied to each epoch. The values of the measures obtained from the jth baseline epoch form a Z-dimensional measure vector, $(\mu_1^j, \mu_2^j, \ldots \mu_z^j)$ $\hat{u}_k$ denotes the average of the kth measure obtained over all baseline epochs. $\Sigma$ is the covariance matrix of these measures. The degree of a test epoch's departure from baseline can be determined by first applying the same Z measures to that epoch to produce $(\mu_{Test-1}, \mu_{Test-2}, \mu_{Test-3}, \ldots \mu_{Test-z})$. The distance between this test epoch and the baseline recording can then be expressed by the Mahalanobis distance $D_{Test,Baseline}^2$ as:

$$D_{Test,Baseline}^2 = \begin{pmatrix} \mu_{Test-1} - \hat{\mu}_1 \\ \mu_{Test-2} - \hat{\mu}_2 \\ \vdots \\ \mu_{Test-Z} - \hat{\mu}_Z \end{pmatrix}^T \Sigma^{-1} \begin{pmatrix} \mu_{Test-1} - \hat{\mu}_1 \\ \mu_{Test-2} - \hat{\mu}_2 \\ \vdots \\ \mu_{Test-Z} - \hat{\mu}_Z \end{pmatrix}$$

The incorporation of the inverse covariance matrix is crucial to the validity of this distance metric. It corrects for the potential bias that is created when correlated measures are used. Mahalanobis distance can be computed as a function of time by calculating its value as the test epoch is advanced. A change in the signal, in this example, seizure onset or termination, is detected when the value exceeds some empirically determined threshold for a sufficiently long period of time. Additionally, the Mahalanobis distance can be used to compute the probability that vector $(\mu_{Test-1}, \mu_{Test-2}, \mu_{Test-3}, \ldots \mu_{Test-z})$ is an element of the set of baseline measure vectors.

The multivariate signal classification procedure used to detect transitions in signal behavior can be generalized to consider signal prediction. The prediction of spontaneous seizures is considered as an example. Initially it might be supposed that the physiological state of the central nervous system can be dichotomously classified between the ictal state (a seizure is in progress) and the inter-ictal state (a seizure is not present). Seizure prediction algorithms implicitly assume that there is also a pre-ictal state which precedes onset of a clinically discernable seizure and which is distinct from the inter-ictal state. Examples of seizure prediction algorithms are rapidly growing in the art. The assumed presence of a dynamically distinct pre-ictal state can be tested in a multivariate discrimination. Assuming a collection of seizure records, which include inter-ictal and pre-ictal epochs, is available, for each signal, three classes of epoch are defined: ictal epochs, pre-ictal epochs recorded immediately prior to seizure onset, and inter-ictal records that are well displaced temporally from seizure activity. Again a collection of dynamical measures is applied to each epoch. A three-group classification problem results. The between-group Mahalanobis distance can be calculated for each group pair. The probability that any two groups are the same can then be computed. The success of the dynamical measures in establishing the existence of a pre-ictal state is then determined by calculating $P_{SAME}(G_{Inter-ictal}, G_{Pre-ictal})$ which is the probability that the set of measure vectors obtained from the inter-ictal records are different from the set obtained from pre-ictal records. If $P_{SAME}$ is low, then the existence of a dynamically distinct pre-ictal state has been established. In the above example of multivariate transition detection, it was shown that the Mahalanobis distance between the ongoing EEG and its baseline could be computed as a function of time. Similarly, one can compute any given epoch's membership probability in the inter-ictal and pre-ictal groups as the time-dependent functions $P(x_{Test}|G_{Inter-ictal})$ and $P(x_{Test}|G_{Pre-ictal})$. The coincident decrease in $P(x_{Test}|G_{Inter-ictal})$ and increase $P(x_{Test}|G_{Pre-ictal})$ constitutes a prediction of seizure onset.

Two operational points are of note. Suppose that $P_{SAME}(G_{Inter-ictal}, G_{Pre-ictal})$ is high. This constitutes a failure to establish the presence of a pre-ictal state. This does not mean that a pre-ictal state does not exist. It remains possible that the incorporation of different dynamical measures into the analysis will provide convincing evidence for a dynamically distinct pre-ictal state. Secondly, a low value of $P_{SAME}(G_{Inter-ictal}, G_{Pre-ictal})$ does not, of itself, ensure success in predicting seizure onset. The success in seizure prediction is determined by the reliability of pairwise discriminations between the inter-ictal and pre-ictal domains. The pertinent measure in assessing that reliability is not $P_{SAME}(G_{Inter-ictal}, G_{Pre-ictal})$. It is $P_{ERROR}(G_{Inter-ictal}, G_{Pre-ictal})$ which is the probability that an inter-ictal record will be classified as a pre-ictal record (a false alarm) and the probability that a pre-ictal record will be classified as an inter-ictal record (failure to predict). $P_{ERROR}(G_{Inter-ictal}, G_{Pre-ictal})$ is not the same as $P_{SAME}(G_{Inter-ictal}, G_{Pre-ictal})$. It can be much larger. As in the case of $P_{SAME}$, improvements in $P_{ERROR}$ may result from the incorporation of additional measures.

A dynamically distinct pre-ictal state is established by a low value of $P_{SAME}$ while success in prediction is determined, in part, by $P_{ERROR}$. The clinical utility of that prediction is determined by the duration of the pre-ictal state. If the duration of the pre-ictal state is very short, a successful separation of the inter-ictal and pre-ictal period is not necessarily useful. The duration of the warning period can be examined systematically. Let $t_{Onset}$ denote the seizure onset time determined by clinical examination. Let $\Delta_{Pre-ictal}$ denote the duration of the pre-ictal period. In the simplest implementation, it is assumed that the pre-ictal duration is the same for all records and extends from $t_{Onset} - \Delta_{Pre-ictal}$ to $t_{Onset}$. $P_{ERROR}(G_{Inter-ictal}, G_{Pre-ictal})$ can be computed as a function of $\Delta_{Pre-ictal}$. $P_{ERROR}(G_{Inter-ictal}, G_{Pre-ictal})$ will increase as $\Delta_{Pre-ictal}$ increases. The duration of the pre-ictal period, which is to say the length of the warning period, will be the maximum value of $\Delta_{Pre-ictal}$ that gives an acceptable value of $P_{ERROR}$.

EXAMPLE 3

Multi-Channel EEG Sensitivity to Behavioral Changes

In this example both single and multi-channel EEGs were analyzed using measures of signal complexity and algorithmic redundancy, the latter being defined as a sequence-sensitive generalization of Shannon's redundancy. Using a binary partition of EEG activity about the median, redundancy was shown to be insensitive to the size of the data set while being sensitive to changes in the subject's behavioral state (eyes open vs. eyes closed). The covariance complexity, calculated from the singular value spectrum of a multi-channel signal, was also found to be sensitive to changes in behavioral state. Statistical separations between the eyes open and eyes closed conditions were found to decrease following removal of the 8- to 12-Hz content in the EEG, but still remained statistically significant.

In this example the focus was on a class of measures derived from symbolic dynamics. Measures of this type have been successfully applied to the EEG, and differences between signals obtained from healthy controls and schizophrenic patients. Symbolic dynamics have been used to analyze event related potentials elicited by complex linguistic stimuli. Not only have these methods identified well-known components, but they also revealed changes in the signal that were not detected by conventional analytic techniques. Thus, ERP signals are preferably analyzed using procedures from dynamical systems theory and information theory. Although conventional analytic approaches can be augmented very productively by these procedures, the objectives of the present example are more limited.

In this example, free running EEGs were examined and compared via several different measures based on symbolic dynamics to determine the degree to which they can or cannot be used to discriminate between EEG activity in different behavioral states. The Institutional Review Board reviewed all procedures involving human participants. Informed consents were obtained from each participant.

Single-channel EEG recordings were obtained at electrode site Oz from 10 healthy adults who were either resting or doing mental arithmetic. Their eyes were open in both conditions. Electroocular (EOG) activity was recorded from electrodes placed above and below the right eye. In the mental arithmetic condition, participants were instructed to count backwards silently from 763 in steps of seven. The experimenter signaled the beginning and end of each calculation with a verbal command. Recording was not begun until the participant had spent 15 s doing the calculation. The signal to stop was not given until 15 s after the recording had been completed. Continuous 30-s records, not formed by concatenating shorter artifact-free records, were obtained. One record was obtained in each condition for each participant. Calculations were performed with 2, 4, 6, . . . , 20 s subepochs. Signals were digitized at 500 Hz using a 12-bit digitizer. Amplifier cutoffs were set at 0.045 Hz and 30 Hz. Amplifier gain was set at 30,000. Impedances were measured and were less than 5 KΩ. EEG records were monopolar and referenced to linked mastoids. The EOG recording was bipolar. An artifact was operationally defined as either an eye blink detected in the EOG channel or out-of-scale values and amplitude differences larger than 120 mV peakto-peak within 500 ms in any of the other channels. Artifact contaminated records were not included in the analysis. Multi-channel signals were recorded from 13 healthy adults in the second study. Monopolar recordings, referenced to linked earlobes, were obtained from Fz, Cz, Pz, Oz, F3, F4, C3, C4, P3, and P4 using an Electrocap. Vertical and horizontal eye movements were recorded, respectively, from electrode sites above and below the right eye and from near the outer canthi of each eye. These recordings were bipolar. As in the first study, artifact-corrupted records were removed from the analyses. All EEG impedances were less than 5 KΩ. Signals were amplified, gain518,000, and amplifier frequency cutoff settings of 0.03 Hz and 200 Hz were used. Signals were digitized at 1024 Hz using a 12-bit digitizer. Multi-channel records were obtained in two conditions: eyes closed, resting and eyes open, resting. One hundred second recordings were obtained. Calculations were performed with 1,000, 2,000, . . . , 10,000-point subepochs.

The complexity measures constructed in symbolic dynamics quantitatively express the intuitive concept of the degree of disorder in a symbol sequence. For example, a complexity measure provides a systematic procedure for expressing the fact that the symbol sequence:

$S_1$=a a a a b b b b c c c c d d d d e e e e f f f f f g g g g h h h h h i i i i i j j j j is less complex than:

$S_2$=c f d a h e g a j d e h b a b i b a j i c f f g h i h h b f e c i h c g d b j j d i g f e a d j e g c even though they have identical symbol distributions. Several different symbolic complexity measures have been constructed. The class of measure constructed for this example were a nonprobabilistic, model-based, randomness-finding measure. From the point of view of the present development, the most important property of this class of measure is the assignment of highest values of complexity for random sequences and lowest values for highly structured sequences. Even within this category, one can choose from among several candidate measures. Here the Lempel-Ziv complexity measure was selected. When applied to the examples given above, the complexity of the first sequence is 11 and the complexity of the second is 27.

In the case of a stationary process, complexity increases with the number of symbols in the message. This complicates direct comparison of messages of different lengths. A number of normalization procedures have been suggested for comparing messages differing in length. To date, the most successful in the sense of insensitivity to message length is the algorithmic redundancy, which is a sequence-sensitive generalization of the distribution-determined Shannon information redundancy. The redundancy of a symbol sequence is given by:

$R = 1 - (C_{orig} / \langle C_0 \rangle)$:

$C_{orig}$ is the complexity of the original message, which in this implementation is the Lempel-Ziv complexity. $\langle C_0 \rangle$ is the average value of complexity obtained with random equiprobable surrogates of the same length. An equiprobable surrogate is one in which the probability of the ith symbol is $p_i = 1/N_a$, where $N_a$ denotes the number of symbols in the alphabet. Note that $N_a \neq L_M$, the length of the message. In the series given above, $N_a = 10$ and $L_M = 50$. In the computations presented for this example, $\langle C_0 \rangle$ is the average of 10 surrogates. Results obtained from 10 surrogates were found by us to be statistically indistinguishable from those obtained with 50 surrogates. In practice, the appropriate number of surrogates for any given problem can be determined empirically by increasing their number until a stable value of $\langle C_0 \rangle$ is obtained. Redundancy varies between 0 and 1 irrespective of the length of the message. The value of redundancy is dependent on the criterion used to construct the surrogates. There is, therefore, no unique value of redundancy.

The random equiprobable surrogates used in this example provided a primitive test for nonrandom structure. Alternative forms of surrogates such as random-phase surrogates, Gaussian-scaled surrogates, and iterative surrogates provide more demanding tests of structure. Preferably, care is exercised in the construction of surrogates, since surrogate data pathologies can lead to fallacious indications of nonrandom dynamical structure.

An estimate of the uncertainty in redundancy is given by:

$$\Delta R^2 = \left(\frac{\partial R}{\partial C_{orig}}\right)^2 \Delta C_{orig}^2 + \left(\frac{\partial R}{\partial \langle C_0 \rangle}\right)^2 \Delta \langle C_0 \rangle^2$$

$$= \frac{\Delta C_{orig}^2}{\langle C_0 \rangle^2} + \frac{C_{orig}^2}{\langle C_0 \rangle^4} \Delta \langle C_0 \rangle^2$$

where $\Delta \langle C_0 \rangle$ is the standard deviation of the mean $\langle C_0 \rangle$. $\Delta C_{0}$ is the uncertainty in old bum the complexity estimate of the original message. It can be approximated by comparing the complexity value obtained using the first half of the message, $C_A$, and the second half of the message, $C_B$:

$$\Delta C_{orig} \approx \frac{|C_A - C_B|}{(|C_A| + |C_B|)/2} C_{orig}.$$

It has been shown with computationally generated mathematical examples that although the complexity increases with the size of the data set, redundancy is approximately constant. However, long experience with dynamical measures indicates that results obtained with computed data are not necessarily obtained when these measures are applied to noisy biological data. Confirming this theoretical result with electroencephalographic data is demonstrated by this example.

Before a complexity measure can be applied to an EEG signal, it is necessary to reduce the original voltage record to a symbol sequence. There is no single, correct way of doing this. It is nonetheless an important consideration. Inappropriate partitioning of random, real data onto a symbol set can result in the false positive indication of nonrandom structure where none exists. For this example, $N_a = 2$ and partition about the median were selected. That is, every value of voltage less than the median was mapped onto symbol "a" and every value greater than or equal to the median was mapped to symbol "b." The analysis proceeded with an investigation of the resulting symbol sequence. In the absence of a single optimal partitioning procedure, complexity, and hence redundancy, cannot be viewed as having a single value. Rather, these calculations provided a systematic procedure for obtaining an empirical measure of dynamical behavior that can be compared across conditions. Therefore, when reporting the redundancy of a single channel EEG signal, it was preferred to specify (a) the complexity measure used, (b) the number of symbols in the alphabet, (c) the procedure used to partition values of voltage onto a symbol set, (d) the procedure employed to generate the surrogates used to calculate $<C_0>$, and (e) the number of surrogates used. In the results, the Lempel-Ziv complexity measure was used, voltage was partitioned onto a binary symbol set about the median, and 10 random, equiprobable surrogates were used to calculate $<C_0>$.

Additional questions can be addressed when the redundancy of a multi-channel signal is calculated. Several possible ways of applying symbolic measures to multi-channel real data can be considered. In the first, voltage records are reduced to a symbol sequence on a channel-by-channel basis using a specified single channel procedure. Let $S_1^j$, $S_2^j$, $S_3^j$, ... denote the symbol sequence produced by the jth channel. Let M denote the total number of channels. In analogy with embedding of real data, a mathematical process in which observational data is used to construct a set of points in high dimensional space, a multi-channel symbolic analysis can be produced by investigation of the symbol sequence"

$$S_1^1, S_1^2, \ldots S_1^M, S_2^1, S_2^2, \ldots S_2^M, S_3^1, S_3^2, \ldots S_3^M, \ldots$$

Alternately, the multi-channel real data can be embedded in an M-dimensional space. Let $\{V_1^j, V_2^j, V_3^j, \ldots\}$ denote the voltage record obtained from the jth channel. The sequence of points $Z_k = (V_k^1, V_k^2, \ldots V_k^M)$ for $k=1, \ldots, N-M+1$, where N is the number of samples, defines a time dependent trajectory in $\Re^m$. The embedding space can be partitioned into a finite number of elements with a unique symbol assignment to each element. The trajectory can then be mapped to the corresponding symbol sequence.

A simpler procedure is based on the time-dependent distance function, $d_j$:

$$d_j = \{(V_{j+1}^1 - V_j^1)^2 + (V_{j+1}^2 - V_j^2)^2 + \ldots + (V_{j+1}^1 - V_j^1)\}^{1/2}$$

The function $d_j$ can be treated using the previously developed procedures for examining single-channel EEG signals. Procedures based on the singular value decomposition can also be employed. The voltage signal from the jth electrode becomes the jth column of the embedding matrix A:

$$A = \begin{pmatrix} V_1^1 & V_1^2 & \cdots & V_1^M \\ V_2^1 & V_2^2 & \cdots & V_2^M \\ \vdots & \vdots & & \vdots \\ V_N^1 & V_N^2 & \cdots & V_N^M \end{pmatrix}_{N \times M}$$

N is the number of data points in each record. Matrix A is reexpressed using the singular value decomposition:

$$A_{N \times M} = W_{N \times M} D_{M \times M} U^T_{M \times M}$$

D is the diagonal matrix of singular values, $D = \text{diag}(\square_1, \square_2, \ldots, \square_M)$, where the ordering convention is $\square_j \geq \square_{j+1}$ for all j. U is the corresponding orthogonal transformation. Let AU be defined by:

$$AU = WD = \begin{pmatrix} W_i^1 \lambda_1 & W_i^2 \lambda_2 & \cdots & W_i^M \lambda_M \end{pmatrix}.$$

The first column of AU is the first principal component of the multi-channel signal. The second column is the second principal component, and so on. The fraction of total signal variance in the jth principal component is $\text{Var}_j$:

$$\text{Var}_j = \lambda_j^2 \bigg/ \sum_{k=1}^{M} \lambda_k^2.$$

For many physical and biological processes, $\square_i$ can be significantly greater than $\square_{i+1}$; specifically $\square_1$ can be significantly greater than $\square_2$. Over 70% of total signal variance of the 10-channel EEG records examined were in the first principal component. Encouraged by this observation, the analysis proceeded using the first principal component, that is, the first column of AU, as a single channel signal. In this implementation, the Golub-Reinsch algorithm was used to calculate the singular value decomposition.

In addition to the complexity and redundancy of the first principal component, the fraction of variance contained in the first principal component can be used as an empirical measure of the signal. A generalization of this idea can be made in the definition of a covariance complexity, $C_{Co}$, which uses the complete spectrum of M singular values:

$$C_{Co} = -\left(\sum_{k=1}^{M} \text{Var}_j \log \text{Var}_j\right) \bigg/ \log M,$$

where, as noted above, $\text{Var}_j$, the fraction of total signal variance in the jth channel, is dimensionless. Because this is expressed as a ratio, the base of the logarithm is immaterial. $C_{Co}$ is essentially a measure of the degree of departure of the observed variance spectrum from the spectrum produced when a random process forms matrix A. In the case of a random process, variance is uniformly distributed across all channels. $\text{Var}_j = 1/M$, $j=1, \ldots M$ and $C_{Co} = 1$. Using the convexity of $x \log(x)$, it can be shown that this is the maximum possible value of $C_{Co}$. The other extreme is obtained when all variance is confined to the first channel. If $\text{Var}_1 = 1$ and $\text{Var}_j = 0$, $j=2, \ldots M$, then the covariance complexity attains its lowest value $C_{Co} = 0$.

Two implementations of an analysis of multichannel EEGs based on the singular value decomposition are presented. In the first, the voltage signal from each channel was mean normalized. In the second, the voltage signals were first mean normalized and then normalized against the standard deviation on a channel-by-channel basis. In both cases, the first principal component was partitioned onto a two-symbol alphabet about the median. As in the case of single channel signals, the Lempel-Ziv complexity measure was used and redundancy was calculated with 10 random equiprobable surrogates.

Figure 10A:
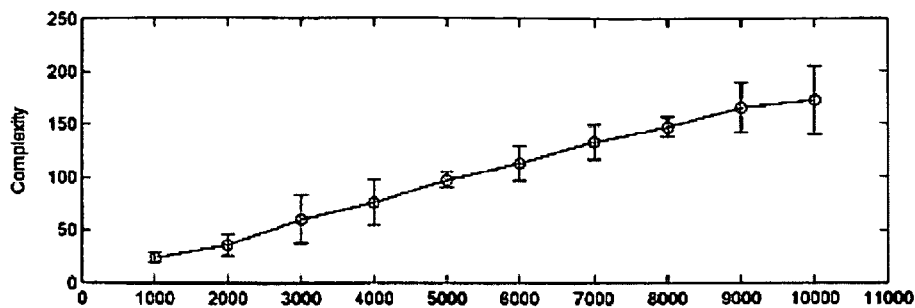
FIGS. 10a and 10b are graphic illustrations showing Lempel-Ziv complexity and redundancy, respectively, computed from a single channel resting EEG as a function of data set size obtained in a third example constructed in accordance with the teachings of the present invention.
Figure 10B:
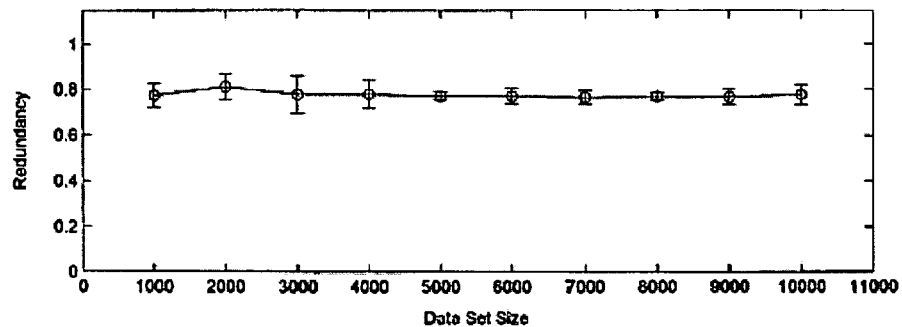

The sensitivity of redundancy as a function of data set length was investigated. The results obtained with 10 single channel EEGs in the rest condition are shown in FIG. 10 which illustrates Lempel-Ziv complexity and redundancy computed from a single channel resting EEG as a function of data set size. The time series was partitioned onto a two-element symbol set about the median. Ten surrogates were used to calculate the redundancy.

As anticipated, the complexity increases as a function of epoch length. In contrast, the values of redundancy are approximately constant. For any given redundancy versus data set size function, the departure of redundancy from its average value is, on average, 2.2%. Thus, the near invariance of redundancy with epoch length observed with computational examples was replicated.

Both the complexity and the redundancy of single-channel records change in response to changes in behavioral state as reflected in Table 3.

TABLE 3

Single Channel Data, Electrode OZ

| Measure | Comparison resting versus arithmetic | p value (paired t test) |
|---|---|---|
| Binary Lempel-Ziv Complexity | Increases | $p < 10^{-5}$ |
| Binary Lempel-Ziv Redundancy | Decreases | $p < 10^{-5}$ |

Figure 11A:
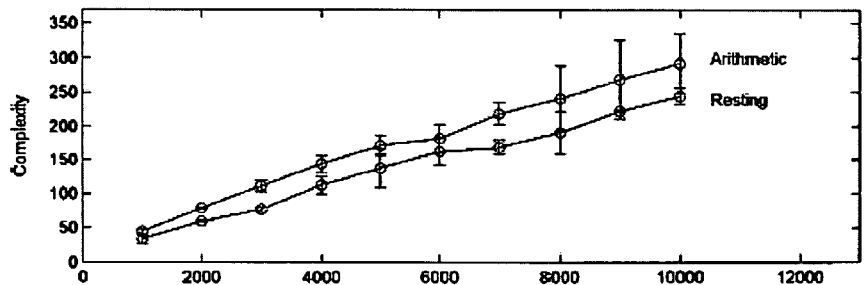
FIGS. 11a and 11b are graphic illustrations showing binary Lempel-Ziv complexity and binary Lempel-Ziv redundancy, respectively, for a single channel EEG obtained in two behavioral conditions in the third example constructed in accordance with the teachings of the present invention.
Figure 11B:
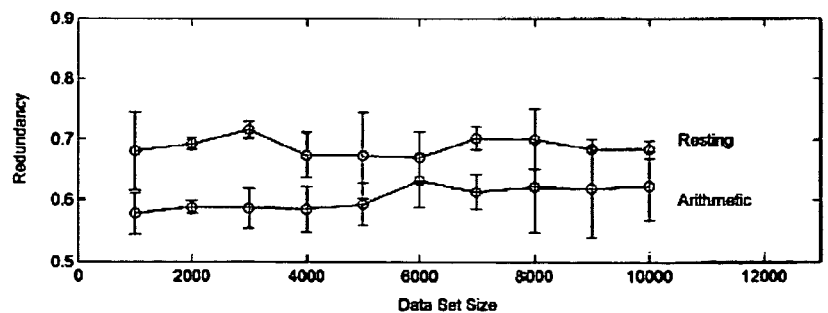

An example is shown in FIGS. 11a and 11b which illustrate binary Lempel-Ziv complexity and binary Lempel-Ziv redundancy, respectively, for a single channel EEG obtained in two behavioral conditions. Results from a single subject are displayed. The complexity of the time series at Oz was greater and the redundancy was lower when the subject was performing mental arithmetic, i.e., the complexity of the EEG is greater when the subject is performing serial arithmetic and the redundancy is lower. A paired t test, which compared the values of complexity obtained with 1,000, 2,000, . . . , 10,000-point data sets across all subjects, was performed. The increase in complexity during the performance of mental arithmetic was found to be statistically significant, $t=4.99$, $p<10^{-5}$. Similarly, the decrease in redundancy was significant, $t=5.10$, $p<10^{-5}$.

Figure 12:
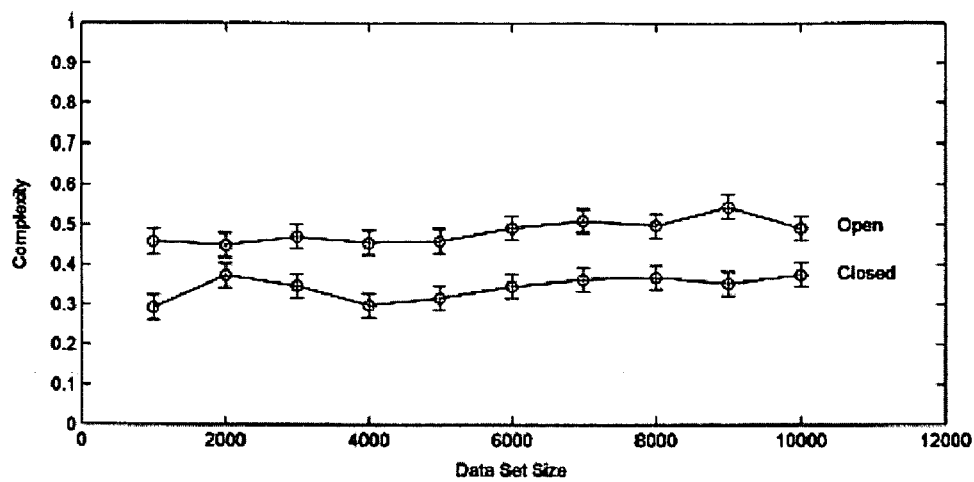
FIG. 12 is a graphic illustration showing covariance complexity for a 10-channel EEG signal obtained in two behavioral conditions in the third example constructed in accordance with the teachings of the present invention.

In the first set of analyses of multichannel data, each channel was mean normalized before the dynamical measures were computed. The previously defined distance function was calculated and it was found that the complexity of the distance function obtained in the eyes-open condition was greater than the complexity of the eyes-closed distance function. In a paired t test of 1,000, 2,000, . . . , 10,000-point records for all 13 subjects, $t=3.46$, $p<10^{-3}$. As suggested by the complexity results, the redundancy is less in the eyes-open condition, $t=2.86$, $p<10^{-2}$. A greater degree of separation across conditions was obtained when the singular value decomposition was performed with mean normalized data. In both the eyes-open and eyes-closed conditions, more than 70% of total signal variance was carried in the first principal component. The fraction of total variance in the first component was greater in the eyes-closed case than in the eyes-open case, $t=4.23$, $p<10^{-4}$. The covariance complexity is also greater in the eyes-open case, $t=5.20$, $p<10^{-6}$. Both of these results were consistent with the expectation that the multichannel signal was more disordered in the eyes-open condition, and, therefore, more of the variance was distributed across higher-order principal components. FIG. 12 shows a comparison of the covariance complexity as a function of data set size in the eyes-open and eyes-closed conditions, specifically, covariance complexity for a 10-channel EEG signal obtained in two behavioral conditions. The covariance complexity is greater in the eyes-open condition than in the eyes-closed condition As previously described, an alternative approach to the analysis of multichannel data is the investigation of the first principal component. The binary Lempel-Ziv complexity of the first principal component of the mean normalized data was found to be greater in the eyes-open condition, $t=6.12$, $p<10^{-7}$, and the redundancy was less in the eyes-open condition, $t=6.62$, $p<10^{-9}$.

The same pattern of results was obtained when the EEG records were both mean normalized and normalized against the standard deviation on a channel-by-channel basis prior to calculating dynamical measures. In some cases, the significance increased. As before, the amount of total variance in the first principal component was greater in the eyes-closed than in the eyes-open condition, $t=3.75$, $p<10^{-3}$, and the covariance complexity was greater when the eyes were open than when they were closed, $t=5.41$, $p<10^{-6}$. The Lempel-Ziv complexity of the first principal component was found once again to be greater in the eyes-open condition, $t=6.89$, $p<10^{-9}$. As before, the redundancy was less when the eyes were open, $t=7.60$, $p<10^{-11}$.

Figure 13A:
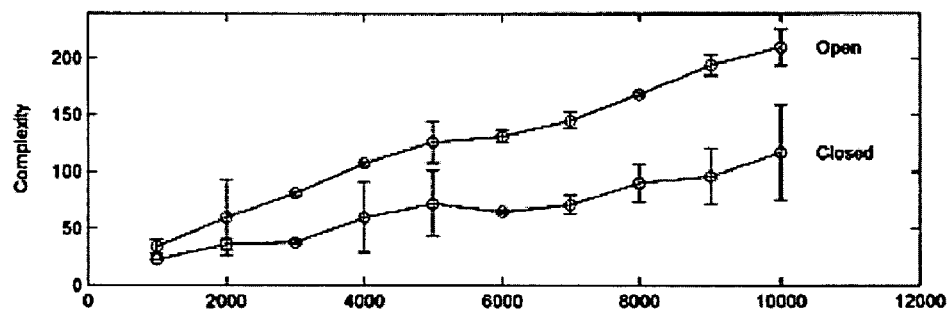
FIGS. 13a and 13b are graphic illustrations showing binary Lempel-Ziv complexity and binary Lempel-Ziv redundancy, respectively, of the first principal component of a 10-channel EEG following mean normalization and normalization against the standard deviation obtained in two behavioral conditions in the third example constructed in accordance with the teachings of the present invention.
Figure 13B:
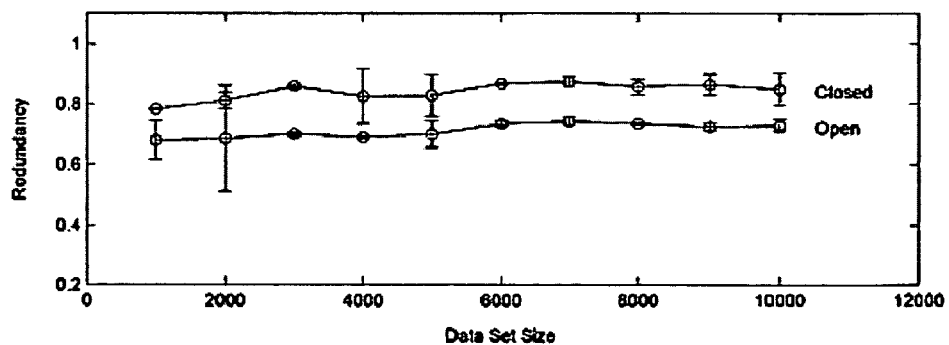

An example is given in FIGS. 13a and 13b which illustrate binary Lempel-Ziv complexity and binary Lempel-Ziv redundancy, respectively of the first principal component of a 10-channel EEG following mean normalization and normalization against the standard deviation obtained in two behavioral conditions. Results from a single subject are displayed. The complexity of the time series was greater when eyes were open. The redundancy was lower.

Results showing the statistical separation between the two conditions when data epochs of 1,000, 2,000, . . . , 10,000 points were compared are presented in Table 4.

TABLE 4

| | | Multichannel Data | | |
|---|---|---|---|---|
| Measure | Comparison eyes-open relative to eyes-closed | Unfiltered p value (paired t test) 1,000, . . . , 10,000 | Unfiltered p value (paired t test) 1,000, . . . , 8,000 | Alpha filtered p value (paired t test) 1,000, . . . , 8,000 |
| 1. Binary Lempel-Ziv complexity of the distance function | Increases | $p < 10^{-3}$ | $p < 10^{-2}$ | $p < .04$ |
| 2. Binary Lempel-Ziv redundancy of the distance function | Decreases | $p < 10^{-2}$ | $p < .03$ | $p < .03$ |
| 3. Fraction of variance in the first principal component (Protocol 1)[a] | Decreases | $p < 10^{-4}$ | $p < 10^{-3}$ | $p < .03$ |

TABLE 4-continued

Multichannel Data

| Measure | Comparison eyes-open relative to eyes-closed | Unfiltered p value (paired t test) 1,000, . . . , 10,000 | Unfiltered p value (paired t test) 1,000, . . . , 8,000 | Alpha filtered p value (paired t test) 1,000, . . . , 8,000 |
|---|---|---|---|---|
| 4. Covariance complexity (Protocol 1) | Increases | $p < 10^{-6}$ | $p < 10^{-4}$ | $p < 10^{-2}$ |
| 5. Binary Lempel-Ziv complexity of the first principal component (Protocol 1) | Increases | $p < 10^{-7}$ | $p < 10^{-5}$ | $p < 10^{-4}$ |
| 6. Binary Lempel-Ziv redundancy of the first principal component (Protocol 1) | Decreases | $p < 10^{-9}$ | $p < 10^{-7}$ | $p < 10^{-5}$ |
| 7. Fraction of variance in the first principal component (Protocol 2)[b] | Decreases | $p < 10^{-3}$ | $p < 10^{-2}$ | $p < 10^{-2}$ |
| 8. Covariance complexity (Protocol 2) | Increases | $p < 10^{-6}$ | $p < 10^{-4}$ | $p < 10^{-4}$ |
| 9. Binary Lempel-Ziv complexity of the first principal component (Protocol 2) | Increases | $p < 10^{-9}$ | $p < 10^{-6}$ | $p < 10^{-4}$ |
| 10. Binary Lempel-Ziv redundancy of the first principal component (Protocol 2) | Decreases | $p < 10^{-11}$ | $p < 10^{-8}$ | $p < 10^{-5}$ |

[a]Protocol 1: Data were mean normalized on a channel-by-channel basis but not normalized with respect to the standard deviation
[b]Protocol 2: Data were mean normalized and normalized with respect to the standard deviation.

The degree of robustness of these results to the length and number of subepochs is a matter of interest because it is known that many dynamical systems require very large data sets and are sensitive to local nonstationarities in the time series, the probability of which increases with the length of the data set. The results depicted in FIGS. 11a-13b suggest that RO(CLZ) and covariance complexity values are approximately stable with as few as 1,000 points, a 1–s recording. This qualitative impression is supported by the numerical results in the second column of Table 4. These values of p were obtained when 1,000, 2,000, . . . , 10,000 element subepochs were compared.

When the transition to 8,000 data point sets is made, the statistical separation between the two behavioral states decreases, but the decrease is not dramatic. The results summarized in the third column of Table 4 were obtained after the alpha band was filtered from the signals.

An important limitation of these results should be recognized. The sensitivity of complexity and redundancy to changes in behavioral state does not immediately demonstrate that these measures can be used for signal classification. Consider the specific example developed here of multichannel signals obtained in the eyes-open and eyes closed conditions. The 10 measures listed in Table 4 were calculated for each signal in the library. In a paired t test, each measure was found to respond to changes in condition (eyes open vs. eyes closed). However, it should be remembered that a paired t test examines changes within individuals. Considered as a population, the distribution of, for example, values of covariance complexity obtained in the eyes-open condition was broad and overlaps with the distribution of values obtained in the eyes-closed condition. Suppose a multichannel signal is obtained and a question raised is: Was this signal recorded in the eyes-open or in the eyes-closed condition? Because of the broad, overlapping distributions, covariance complexity used alone cannot provide an effective means for classifying the signal. However, it is not necessary to attempt a classification based on a single measure. Discriminant analysis is a multivariate procedure.

In the first instance, the procedure was implemented using the 10 dynamical variables listed in Table 4, calculated with 10-channel EEG data obtained in the two conditions (eyes closed vs. eyes open). Each signal was sampled 10,000 times, and each group contained 13 subjects. $P_{ERROR}$ (Open, Closed) is the mathematically predicted error rate in a pairwise classification based on the minimum Mahalanobis distance. It was found to be 15.7%. Because the measures used in the discrimination are highly correlated, one would expect that it should be possible to obtain a nearly equivalent degree of discrimination between the two behavioral conditions using a subset of these 10 variables. This expectation can be tested in a process of backward elimination that begins with the full complement of measures. The Mahalanobis distance and $P_{ERROR}$ are calculated. Additionally, it is instructive to calculate $R^2_{A,B}$, the coefficient of determination between Groups A and B, which gives the fraction of total between-group variance that can be accounted for with these measures. The Mahalanobis distance is then calculated using the 10 possible combinations of nine measures. The measure that makes the smallest contribution to the Mahalanobis distance is eliminated. In this example, this was the binary Lempel-Ziv complexity of the first principal component calculated following mean normalization and normalization with respect to the standard deviation. $P_{ERROR}$ and $R^2_{A,B}$, are recalculated using this reduced variable set. It is seen that elimination of this variable had a negligible impact on discrimination. The process continued sequentially.

Figure 14A:
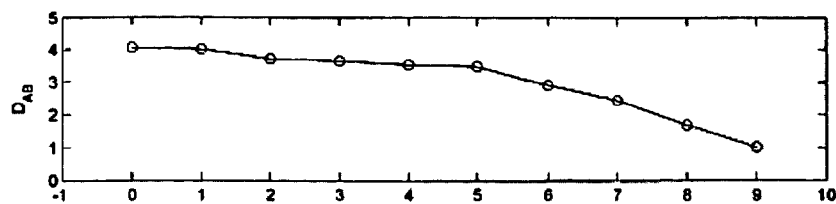
FIGS. 14a, 14b and 14c are graphic illustrations showing sensitivity of discrimination and backward elimination with respect to the between-group Mahalanobis distance, DAB, the coefficient of determination, RAB, and the probability of error in a pairwise discrimination, $P_{ERROR}$, respectively, plotted as a function of the number of measures eliminated from the discrimination obtained in the third example constructed in accordance with the teachings of the present invention.
Figure 14B:
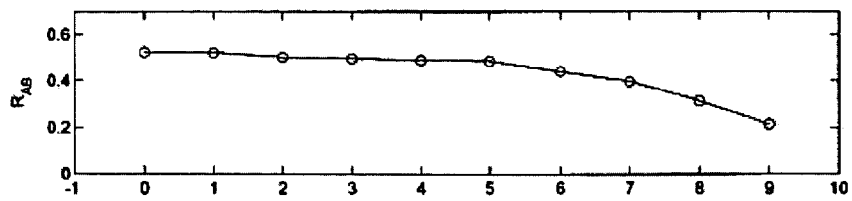
Figure 14C:
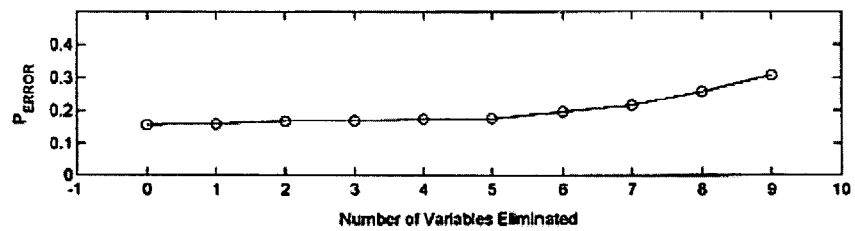

The results are graphically depicted in FIGS. 14a–14c which illustrate sensitivity of discrimination and backward elimination. The between-group Mahalanobis distance, $D_{AB}$, the coefficient of determination, $R_{AB}$, and the probability of error in a pairwise discrimination, $P_{ERROR}$, are plotted, respectively, as a function of the number of measures eliminated from the discrimination. At each step, the least significant variable was removed.

After sequential elimination of 9 of 10 measures, the retained measure was the binary Lempel-Ziv redundancy of the first principal component following mean normalization and normalization with respect to the standard deviation. The theoretical $P_{ERROR}$ had increased from 15.7% to 30.7%. The maximum error rate, corresponding to random assignment, is 50%. The details of this process, including a sequential identification of the eliminated measures, is given in Table 5.

$P_{ERROR}$ estimates can be inaccurate. Both overestimates and underestimates of the operationally observed classification rates are possible. An empirical check of the efficacy of complexity based EEG classification is preferably performed. When considering empirical classification tests, a distinction is preferably drawn between in-sample and out-of-sample classifications. In an in-sample classification, the signal to be classified is retained in the signal library. In an out-of-sample classification, the signal to be classified is eliminated from the library. In-sample classifications can give unrealistically optimistic estimates of classification error rates. This is seen to be the case for these data (Table 6).

TABLE 6

Classification Errors: Multi-channel Data

| | Error rate random assignment | Error rate minimum Mahalanobis distance in-sample classification | Error rate maximum Bayesian likelihood in-sample classification | Error rate minimum Mahalanobis distance out-of-sample classification | Error rate maximum Bayesian likelihood out-of-sample classification |
|---|---|---|---|---|---|
| Eyes-closed | 50% | 7.7% | 0% | 85% | 69% |
| Eyes-open | 50% | 0% | 0% | 46% | 46% |

Signals were classified with two criteria, the minimum Mahalanobis distance, which is the basis of $P_{ERROR}$ calculations, and maximum Bayesian likelihood. There was a dramatic increase in error rate when an out-of sample classification is performed.

There are two reasons for the increase in the error rate when an out-of-sample classification is performed. They are both related to the low number of members in the two groups (eyes-open vs. eyes-closed, N=13 in both cases). If N, the number of elements in each group is low, the within-group average values of the characterizing measures can change significantly if a member is eliminated, as is necessary in an out-of-sample classification. Similarly, if N is small, the elements of the covariance matrix can change when the test element is deleted. Changes in the average value and the within-group covariance matrix result in changes in the Mahalanobis distance and have a potentially damaging impact on the efficacy of the classification process. Thus, as an operational response to the question "How many members should be in each group?" the conclusion was that N must be large enough to ensure that the vector of average values and the within-group covariance matrix were robust against the elimination of any single element from the group.

There is an additional factor associated with errors in the classification process that is preferably considered. If the dynamical measures used in a multivariate discrimination are highly correlated, as in the present example, the within-group covariance matrix can be near singular. The calculation of the Mahalanobis distance requires calculation of the inverse of this matrix. If the matrix is ill conditioned, significant numerical inaccuracies, and hence classification errors, can result. This situation can be exacerbated by the transition from within-sample to out-of-sample classifications because the covariance matrix can become more ill conditioned when the test element is deleted from the signal library. To protect against errors that result from the inaccurate inversion of a near-singular covariance matrix, two

TABLE 5

Backward Elimination of Discriminant Measures

| Eliminated variable | Between-group Mahalanobis distance | Coefficient of determination | $P_{ERROR}$ |
|---|---|---|---|
| None | 4.0510 | .5232 | .1571 |
| Binary Lempel-Ziv complexity of the first principal component (Protocol 2) | 3.9999 | .5200 | .1587 |
| Fraction of variance in the first principal component (Protocol 2) | 3.7086 | .5011 | .1678 |
| Covariance complexity (Protocol 2) | 3.6494 | .4971 | .1697 |
| Covariance complexity (Protocol 1) | 3.5368 | .4892 | .1735 |
| Fraction of variance in the first principal component (Protocol 1) | 3.4797 | .4852 | .1755 |
| Binary Lempel-Ziv redundancy of the distance function | 2.9075 | .4405 | .1969 |
| Binary Lempel-Ziv complexity of the first principal component (Protocol 1) | 2.4551 | .3994 | .2167 |
| Binary Lempel-Ziv complexity of the distance function | 1.6939 | .3145 | .2576 |
| Binary Lempel-Ziv redundancy of the first principal component (Protocol 1) | 1.0191 | .2163 | .3069 | numerical procedures for performing these calculations were coded and comparison tested. Multiplying the matrix and its inverse and then observing the degree of departure from the identity matrix tests the quality of matrix inversion. The first procedure used was the standard LU-decomposition for inverting square, real matrices. When the covariance matrix and its inverse were multiplied, significant departures from identity were observed, and, most particularly, the product $A^{-1}A$ was significantly different from $AA^{-1}$. The LU-decomposition is a generic procedure that can be used to invert any matrix. This method does not exploit explicitly the internal structure of a covariance matrix. An alternative inversion procedure that utilizes this structure and is specific to covariance matrices may be used. When applied to the extremely ill-conditioned matrices encountered in this discrimination, better performance, in the sense that $A^{-1}A$ and $AA^{-1}$ are approximately equal, is obtained.

It is commonly supposed that incorporating additional measures into a multivariate discrimination may or may not improve performance, but will not cause a deterioration in performance. If, however, the added measures are highly correlated with measures already used in the discrimination, their incorporation will result in a near-singular within-group covariance matrix. The consequent numerical errors associated with the inversion of this matrix and the calculation of the Mahalanobis distance can cause a significant increase in the classification error rate. This is illustrated by this third example. The analysis began with an examination of the 10×10 within-group covariance matrix formed using all 10 of the measures listed in Table 5. Calculation of the singular values of these matrices indicated that they were effectively three dimensional. For example, in descending order, the singular values of the covariance matrix of the eyes-open group are: 6311, 218, 165, $10^{-2}$, $10^{-3}$, $10^{-4}$, $10^{-5}$, $10^{-10}$, $10^{-13}$, and $10^{-13}$.

Figure 15:
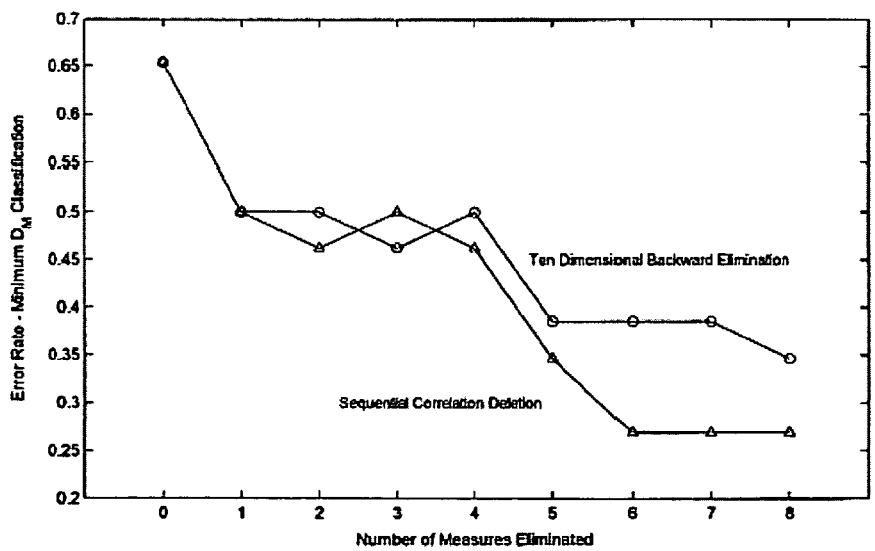
FIG. 15 is a graphic illustration showing error rate in an out-of-sample classification as a function of the number of variables eliminated from the discrimination obtained in the third example constructed in accordance with the teachings of the present invention.
Figure 16A:
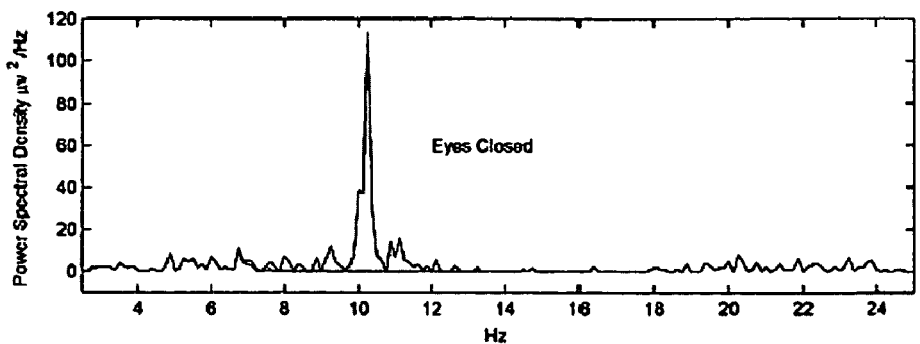
FIGS. 16a and 16b are graphic illustrations showing power spectral density (PSD) of signals before and after removal of the alpha component recorded from a single subject at electrode site PZ obtained in two behavioral conditions, respectively, in the third example constructed in accordance with the teachings of the present invention.
Figure 16B:
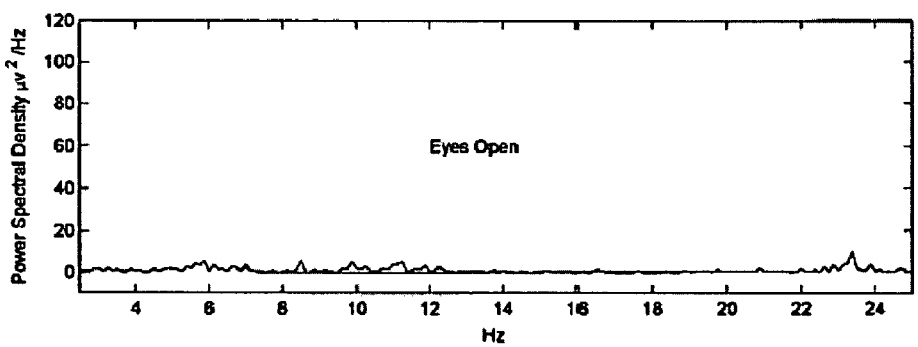

The deleterious impact of carrying redundant measures on the out-of-sample classification error rate is depicted in FIG. 15 which shows error rate as a function of the number of variables eliminated from the discrimination. FIGS. 16a and 16b illustrate power spectral density (PSD) of signals before and after removal of the alpha component recorded from a single subject at electrode site PZ. In the case of the unfiltered, eyes-closed signal, an alpha peak appears at approximately 10.25 Hz. In the case of the filtered signals, the power spectral density in the alpha band is the straight line at PSD50. The two spectra superimpose outside of this frequency range. The upper trace shows performance as variables are eliminated in the sequence determined in a backward elimination. This sequence is shown in Table 4. In contrast with the view "the more measures the better," it is seen that the error rate decreases from 65% to 35% as variables are eliminated from the discrimination.

Sequential correlation elimination, an alternative procedure for eliminating variables from the discrimination, was also tested, and the results are compared with backward elimination in FIG. 15 which illustrates error rate in an out-of-sample classification as a function of the number of variables eliminated from the discrimination. The elimination sequence in the upper trace (denoted by circles) was determined by a backward elimination. The elimination sequence of the lower trace (triangles) was determined in a sequential correlation deletion. The process of sequential correlation elimination began by calculating the coefficient of determination for all 10 candidate measures. The process of elimination was guided by the coefficients of determination and the correlations between measures. Three procedures for assessing correlations were implemented: Pearson linear correlation, Spearman nonparametric correlation, and Kendall's tau. No differences in the elimination sequences resulted when different correlation measures were used.

The process of sequential elimination began with the observation that complexity and redundancy were highly correlated. Eliminating the three redundancy measures (Table 4) and retaining the corresponding complexities did not, therefore, result in a loss of discriminatory power. Their elimination did, however, result in a significant improvement in the accuracy of Mahalanobis distance calculations. The error rate decreases form 65% to 50% with the elimination of redundancies.

The subsequent elimination process was guided by the coefficients of determination of the remaining variables and their correlations. Of the remaining variables, the highest correlation is between Measure 3 (the numbering follows that of Table 4, Measure 3 is the fraction of variance in the first principal component calculated with Protocol 1, which is mean normalization) and Measure 4 (the covariance complexity calculated with Protocol 1) where r=0.956. Of these two measures, the covariance complexity had the highest coefficient of determination. Therefore the third measure was eliminated and the error rate again decreased.

The next highest correlation, r=0.946, was between the fraction of variance in the first component calculated with Protocol 2 (mean normalization followed by channel-by-channel normalization against the standard deviation) and the covariance complexity calculated with Protocol 2. Of the two, the covariance complexity had the higher coefficient of determination. So, as with the corresponding Protocol 1 measures, the fraction of variance in the first principal component was dropped from the discrimination.

Following that elimination, the highest correlation, r=0.927, was between the binary Lempel-Ziv complexity of the first principal component (Protocol 1) and the corresponding Protocol 2 complexity. The Protocol 2 complexity was retained because it had the higher coefficient of determination. At this point in the process, the highest correlation, r=0.831, was between the Protocol 1 and Protocol 2 covariance complexities. In that case, the Protocol 1 variant had a slightly higher coefficient of determination and was retained. As predicted from the singular value spectra, the final three measures, binary Lempel-Ziv complexity of the distance function, covariance complexity (Protocol 1), and binary Lempel-Ziv complexity of the first principal component (Protocol 2), had low correlations (r<0.3). Of these, the covariance complexity (Protocol 1) had the lowest coefficient of determination. By implementing a sequential correlation elimination, the empirically determined error rate in an out-of-sample classification decreased from 65% to 27%. In this example, sequential correlation elimination outperformed backward elimination.

The alpha component of the EEG was attenuated in the eyes-open condition. Accordingly, it was expected that a complexity measurement would discriminate between these two conditions. A more demanding question was: Do the differences in these measures observed across the eyes-closed and eyes-open conditions reflect a change in the signal that cannot be explained by attenuation of alpha content? This question was examined by repeating the calculations of Table 4 with the same data following digital removal of the alpha component. Signals of 8,192 elements were produced with a 1,000-order Hamming filter that removed the 8–12 Hz component. A comparison of the power spectral density of a signal before and after filtering is shown in FIGS. 16a and 16b. The restriction to a signal length equal to a power of two (in this case 8,192) was imposed by the filter. Therefore, direct comparisons with the results of Table 4 in which 10,000-point data sets were used could be misleading. The between-group statistical separation for each measure was computed in a paired test for 1,000, 2,000, 3,000, . . . , 8,000-element epochs. The results are also presented in Table 4. When the values obtained using unfiltered 8,000-point data sets (Table 4) were compared against those obtained with 10,000-point data sets, it was seen that the significance levels were comparatively robust to changes in data set length. When filtered and unfiltered signals were compared (Table 4), it was seen that, although the statistical separation between conditions decreased after removal of the alpha content, the differences remained significant.

An additional issue that is preferably considered when control population and clinical EEGs are compared is that the records obtained from highly cooperative control subjects have much higher signal-to-noise ratios (SNRs) than those obtained from clinical populations. It is, therefore, at least possible that in some instances, the observed differences in dynamical measures reflect different SNRs rather than physiological differences in the dynamical systems that generated the recorded signals. The crossover design employed in this example in which comparisons were made between signals obtained from each subject in two conditions provides a partial means of addressing this concern. Additionally, it is possible to control for noise levels directly. A mathematical procedure provides an empirical estimate of a signal-to-noise ratio in the absence of knowledge of the noise-free signal. By adding observational noise to signals prior to analysis, a dynamical investigation can be performed with uniform SNRs. Such investigation begins with two immediate technical objectives: (a) Construct a measure of signal complexity that, in the case of stationary systems, is invariant to the length of the data set, and (b) construct a procedure that permits application to multichannel signals. The first objective was met by showing that a generalization of Shannon's information redundancy produced a measure that was sequence sensitive (in contrast, Shannon redundancy is distribution determined) and invariant to data set length. Two procedures for applying this measure to multichannel data were considered. The first was based on the calculation of a distance function created by first embedding the multichannel signal in an M-dimensional embedding space. The second procedure constructed the signal's first principal component using the Golub-Reinsch algorithm to calculate the singular value decomposition. It was found that the first principal component carried approximately 70% of total signal variance. Statistically significant between state differences were observed with these measures when they were applied to eyes-open versus eyes-closed multichannel EEGs. Additionally, when the 8-12-Hz component of the signal was removed, the differences observed across behavioral conditions decreased, but remained statistically significant. These results have two distinct domains of application. The first is the use of these measures for the empirical comparison of EEG signals. The second, more abstract, application is the use of complexity measures as metrics of consciousness. Each application is considered separately.

Complexity measurements of EEGs finds application in three interrelated activities: signal classification, the detection of change (smart alarm technology), and the prediction of change. A prima facie case for the potential value in classification is given in the results of this example. It is to be explicitly recognized that differentiation between eyes-closed and eyes-open EEGs obtained from healthy subjects is not a demanding exercise. However, the degree of statistical separation obtained reflects that, when used in combination with other measures, these calculations are useful in more demanding classification problems. Restated in clinical language, EEG classification are the foundation of an EEG-based diagnosis. The results of this example reflect that the resolution of diagnostic algorithms can be improved by adding measures derived from symbolic dynamics. However, diagnosis is a particularly difficult challenge. Other applications can be made by calculating complexity longitudinally in intra-patient studies that assess the response to treatment. Appropriately constructed complexity measures can provide a "unified conceptual framework" for investigating higher CNS function.

In application of dynamical measures to EEGs and ERPs preferably: (a) more than one dynamical measure are used, and higher priority should be given to measures that are known to be more robust against nonstationarities in the data; (b) all computations are validated with surrogate data and more than one surrogate algorithm is used; (c) when possible, multichannel rather than single-channel data is used; and (d) an effort is made either by experimental design or by post-acquisition numerical analysis to control for signal-to-noise ratios when making between group comparisons.

EXAMPLE 4

Individuality of Goldfish Locomotion

Goldfish swimming was analyzed quantitatively to determine if it exhibits distinctive individual spatiotemporal patterns. Due to the inherent variability in fish locomotion, this hypothesis was tested using five nonlinear measures, complemented by mean velocity. A library was constructed of 75 trajectories, each of 5 min duration, acquired from five fish swimming in a constant and relatively homogeneous environment. Three nonlinear measures, the 'characteristic fractal dimension' and 'Richardson dimension', both quantifying the degree to which a trajectory departs from a straight line, and 'relative dispersion', characterizing the variance as a function of the duration, have coefficients of variation less than 7%, in contrast to mean velocity (30%). A discriminant analysis, or classification system, based on all six measures revealed that trajectories are indeed highly individualistic, with the probability that any two trajectories generated from different fish are equivalent being less than 1%. That is, the combination of these measures allows a given trajectory to be assigned to its source with a high degree of confidence. The Richardson dimension and the 'Hurst exponent', which quantifies persistence, were the most effective measures.

Swimming is composed of highly organized spatial and temporal patterns even in a relatively homogeneous environment. Some of these patterns are complex and cannot be characterized with the tools of classical kinematics, as they may exhibit nonlinear properties, such as persistence (the tendency to repeat a given sequence), redundancy (the relationship between the uncertainty of a signal and its length) and scale invariance (a tendency for a signal to have the same structure when observed on different temporal or spatial scales). This example illustrates the application of five nonlinear measures and one linear measure as descriptors of goldfish swimming trajectories in order to quantify this locomotor behavior and the development of a discriminant analysis that allowed the determination of whether a given trajectory could be assigned to an individual within the experimental pool. It was found that, despite the apparent variability of trajectories, such a classification could reliably be achieved.

Mature goldfish (*Carassius auratus* L.) were purchased from a commercial hatchery. Upon arrival in the laboratory, the animals were adapted to laboratory conditions for at least one week. Five female fish with similar body length (9–12 cm) were chosen randomly. They were maintained together in a rectangular glass aquarium (92 cm×41 cm×1 cm; 75 liter), using deionised water conditioned with NovAqua (0.13 ml $l^{-1}$; Novalek Inc., Hayward, Calif.), Instant Ocean (16 mg $l^{-1}$; Aquarium Systems, Mentor, Ohio), Aquarium Salt (0.125 g $l^{-1}$; Jungle Labs, Cibolo, Tex.), Copper Safe (0.32 ml $l^{-1}$; Mardel Laboratories, Inc., Harbor City, Calif.) and pH Stabilizer 7.2 (0.125 g $l^{-1}$; Jungle Labs).

Water quality was monitored regularly and was the same for holding and experimental tanks (temperature 22±1° C.; pH 7±0.2; dissolved oxygen saturated, 8 p.p.m.). Fish were fed on a regular 48-h schedule. A 12 h:12 h light:dark cycle was supplied by room lights (360 lux at the water surface). All video recordings were made during the light period.

A cylindrical Plexiglas tank (20 liter, 50 cm diameter) was used for the experiments. The water column was comparatively shallow (10 cm deep) to prevent fish from swimming out of the camera's focal plane and to minimize errors due to changing swimming depth. To reduce mechanosensory and visual cues, the tank was mounted on an anti-vibration table and its wall and lid were translucent white. Its bottom was clear to allow video recording from below. Translucent white plastic sheets were mounted on the inside frame of the table with a small hole in the bottom sheet for the camera lens.

Illumination was from above with a circular fluorescent bulb (approximately 350 lux at the water surface) and from below with four floodlights (approximately 250 lux at the bottom of the tank). New conditioned water was used for each recording session.

Approximately 30 min prior to all recording sessions, fish were transferred to a translucent white container (20 cm×15 cm×10 cm) filled with aerated, conditioned water, to be marked for automated motion tracking. Two markers were applied with instant adhesive (Quick Tite; Locktite Corp., Avon, Ohio, USA) along the ventral midline of the fish to specify its position on the video image. They were made of double-sided black tape (1 cm×1 cm) with a dot (approximately 4 mm diameter) of white nail polish painted in the centre. For this purpose, the fish was removed from the water, the ventral midline was exposed and the skin was gently dried. The markers were applied between the paired pelvic and pectoral fins and onto the lower jaw in less than 1.5 min, after which the fish recovered in fresh aerated water for at least 10 min. This procedure had no obvious impact on behavior and, in most cases, the marker remained in place for several days.

To analyze locomotion recordings of the ventral view of the fish were obtained from below at 30 Hz using a digital camcorder (Canon Optura; Canon USA, Jamesburg, N.J., USA). Each recording session started 30 s after the fish was introduced into the experimental tank and lasted 15 min. Video capturing software (Adobe Premiere; Adobe Systems Inc., San Jose, Calif., USA) was used to subdivide a recording session into three 5-min trajectories. Five such recording sessions, each obtained on a different day, were collected from five fish and used to construct a library of 75 trajectories.

Figure 17A:
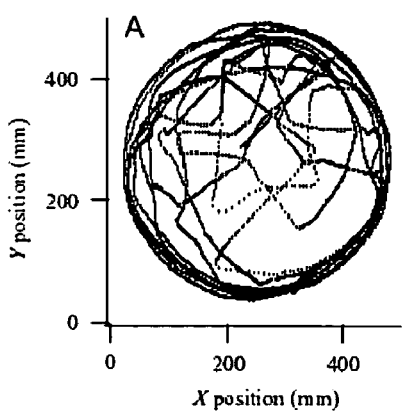
FIGS. 17a and 17b are graphic illustrations showing a representative swimming trajectory from a single fish recorded over a 5-min period with a sampling frequency of 30·Hz and the corresponding instantaneous velocity as a function of time respectively, in a fourth example constructed in accordance with the teachings of the present invention.
Figure 17B:
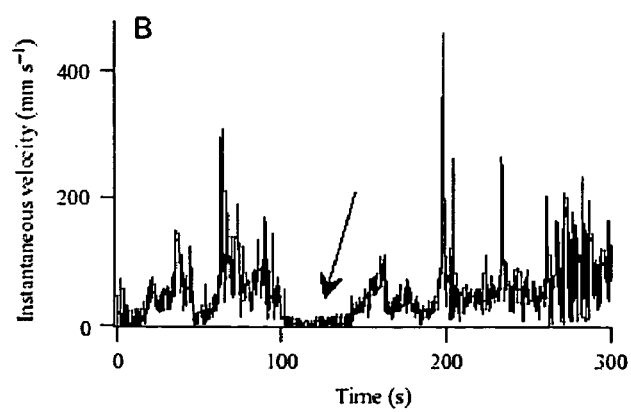

FIG. 17*a* is a graph that shows a representative trajectory from a single fish recorded over a 5-min period with a sampling frequency of 30 Hz. FIG. 17*b* illustrates the corresponding instantaneous velocity as a function of time. The arrow indicates a period of inactivity that was confirmed by direct examination of the video recording.

Commercial motion analysis software (WinAnalyze; Mikromak GmbH, Erlangen, Germany) provided frame-to-frame data on the X and Y position of the markers (FIG. 17*a*). Only the central marker data were used for the calculations in this example. The X and Y position data as functions of time were used as primary data for the multivariate analysis described below. The five nonlinear measures chosen for this example were computed with software; the mean velocity was then taken as the 5-min average of the instantaneous velocity $[(dx/dt)^2+(dy/dt)^2]^{0.5}$. A pragmatic criterion for choosing each nonlinear measure was that it should provide a quantitative value that could be assigned to a trajectory, allowing for statistical comparisons between groups of data.

As noted above, the characteristic fractal dimension (CFD) measures the degree to which a trajectory departs from a straight-line path. It is a measure of the total distance traveled from point to point (or frame to frame) relative to the maximum separation of any two points in the series. In other words, it is an approximation, equal to the distance traveled divided by the diameter of the experimental tank. It is sensitive to the duration of the observation period and to the speed of motion. It has a minimum value of 1 but does not have an upper limit. Since, in this example, the fish were swimming in a cylindrical tank, a circular motion of constant velocity was equivalent to a straight line. As the trajectory deviated from circular motion, the CFD increased.

As noted above, the Richardson dimension ($D_R$) is also an estimate of the degree to which a trajectory departs from a straight line. In contrast with the CFD, $D_R$ also quantifies how the estimate of a curve changes with the precision of the measurement. It is an example of the generic class of dimension measures that have been applied to the analysis of the classical problem of fractal geometry, namely 'How long is the coast line of Britain?' Stated operationally, for a fixed step length one counts the number of steps required to walk around the coast (or, as in this example, along the fish's trajectory). The length of the stride, i.e. the distance covered with each step, is then reduced and the number of steps required using this new step length is determined. The process is repeated and the log of the number of steps required is plotted as a function of the log of the step length. Thus, $D_R$ is a measure for scale invariance. The slope of this curve is used to determine $D_R$. As for the CFD, a value of 1 is obtained from a straight line. The value of 2 is the maximum possible $D_R$ and it represents a theoretical limit when a trajectory covers the entire two-dimensional surface. Given the differences between the factors influencing the CFD and $D_R$, they can diverge.

Measures of fractal analysis comparable to CFD and $D_R$ have been used to describe behavioral sequences, such as swimming and foraging in clownfish, trails in mites, reproductive behavior in fathead minnows, social behavior in chimpanzees and head lifting during feeding behavior in ibex.

As noted above, the Lempel-Ziv complexity (LZC) is a sequence-sensitive measure that characterizes the structure of time-varying signals as a series of symbols. The spatial difference in the fish's position between two consecutive points in time is compared, generating a time series of incremental distance traveled. This distance function is simplified by partitioning it into a binary symbol sequence about the median increment size. For example, a typical sequence might be 'aabaabbab' where 'a' symbolizes values less than the median and 'b' symbolizes those greater. Then, the LZC is calculated for the resulting symbol sequence. It reflects the number of sub-strings in the sequence (e.g. aab) and the rate at which they occur. This measure therefore gives information about the redundancy (or lack thereof) of a trajectory, for example about the irregularity of its velocity.

The value of LZC increases approximately linearly with the number of measurements in the time series and attains a maximum with random numbers. For data sets of the length used in this example (9000), a maximum of approximately 700 would be expected.

As noted above, the Hurst exponent (HE) measures persistence—the tendency of large displacements to be followed by large displacements (e.g. an increase is followed by an increase) and small displacements to be followed by small displacements—and anti-persistence, which is the tendency of large displacements to be followed by small displacements (e.g. an increase is followed by a decrease) and vice versa. In other words, it describes how deterministic a trajectory is, i.e. the extent to which a future component of the trajectory is specified by components of its past. Theoretically, its range of possible values is 0 to 1, with 0.5 as the crossover point between anti-persistence and persistence (since it is estimated from the log-log plot of variability versus epoch length, uncertainty in curve fitting can expand this range slightly). An HE of 0.5 would be obtained if the trajectory was indistinguishable from a random walk. Biological applications of the HE have included investigations of heart interbeat interval sequences and pulmonary dynamics.

As noted above, the Relative dispersion (R. Disp.) measures the dependence of signal variance on the duration of the dataset. It ranges from 1.0 to 1.5 and quantifies the change in the uncertainty in a time series' mean value as the observation period increases. Practically, the R. Disp. is the slope of the linear region of a log-log plot of the coefficient of variation of a signal versus the length of the data set. Its primary applications have been in the analysis of the physics of turbulent flow, but it has also been used in the quantitative characterization of pulmonary perfusion.

All of the algorithms used to calculate these measures were sensitive to noise in the data, non-stationarities in the underlying dynamics and the temporal duration of the examined epoch. For example, filtered noise can mimic low dimensional chaotic attractors and, if inappropriately applied, the method of surrogate data (which is used to validate dynamical calculations) can give false positive indications of non-random structure. These are central concerns if one is trying to establish the absolute value of one of these measures, such as the true value of the $D_R$. However, this was a less crucial consideration in this example because the value of the measures were not calculated in an absolute sense. Rather, approximations of the empirical measures were calculated, which nonetheless was of value in the classification of the signals. The efficacy of the computed values in the classification was assessed quantitatively in the course of the discriminant analysis, as described below.

A multivariate discrimination was constructed to ask specific questions about the behavioral data. For example, can locomotor performance be distinguished between individual fish? For this purpose, each swimming trajectory was represented by its set of values calculated for the five nonlinear measures described above plus its mean velocity. Since it was possible that no measure alone would provide consistent results for such discrimination, all the measures were incorporated into the discriminant analysis and then their relative contributions to the classification process were assessed. The discriminant analysis was thus based on these six measures, and calculations were made between the sets of values defining individual trajectories in a matrix consisting of a six-dimensional space.

$P_{SAME}$(Fish A, Fish B) was defined as the probability that the six-dimensional measurement distributions corresponding to Fish A and Fish B were drawn from the same parent distribution. The estimate of failure in a pairwise discrimination was $P_{ERROR}$(Fish A, Fish B). This was the theoretically estimated probability that a trajectory from Fish A would be incorrectly classified as a Fish B trajectory and vice versa.

Two classification criteria were used for $P_{SAME}$ and $P_{ERROR}$. The first classification is based on the minimum Mahalanobis distance. In the context of the six-dimensional measure space, the Mahalanobis distance was a generalized mathematical distance between the vector from the single trajectory that was to be classified and the collection of measure vectors calculated from all of the trajectories obtained from one of the fish. The test trajectory was deemed to be a member of the group corresponding to the smallest Mahalanobis distance. The second procedure for classifying a trajectory was based on the Bayesian likelihood. The trajectory's vector was classified into the group corresponding to the maximum Bayesian membership probability. Both classification schemes incorporate a correction for correlations between the measures, ensuring that dynamically similar measures did not bias the classification results. In practice, the two procedures usually give identical results. Cases where results differ correspond to classification with low confidence levels. Finally, as the descriptive analysis did not reveal consistent time-dependent differences between three successive 5-min trajectories for most measures, this variable was not incorporated into the discriminant analysis.

A distinction was made between the out-of-sample classifications and within-sample classification. When an out-of-sample classification was performed, the trajectory to be classified was removed from the library before the classification was calculated. For this reason, the error rates of classifications were always greater than, or at best equal to, the error rates obtained using within-sample classifications, where the trajectory to be classified remains in the library during the calculation. If the number of elements in each group was small (here, there were 15 trajectories for each fish), the disparity between within-sample and out-of sample classifications can be large.

A representative trajectory (FIG. 17a) was characterized by a predominance of swimming along the circumference of the cylindrical tank ('wall hugging' effect) which was occasionally interrupted by swimming across the centre and by changing speed (very fast swimming was indicated by a clear separation between successive data points) and/or direction. Periods of fast swimming were observed as swimming in circles along the wall, without significant change in direction, and as occasional fast sprints across the centre of the tank. Additionally, fish did not only swim forward but sometimes propelled themselves backward, which was not obvious with visual inspection of a trajectory. In general, a trajectory gives the impression of moderate irregularity. However, there were also restricted areas signaled by path components of higher density, mostly along the wall, and visual inspection of the video tapes suggests they correspond to small turning movements of the fish while facing the wall or to periods of inactivity. Swimming in the centre occurred in a different way as the fish swims more calmly and slowly without generating a dense accumulation of path components.

The instantaneous velocity calculated from the trajectory in FIG. 17a is shown as a function of time in FIG. 17b. It reveals high variability within the 5-min recording period. During this epoch, the instantaneous velocity of this trajectory ranged from 0 mm s$^{-1}$ to 460 mm s$^{-1}$, with a mean value of 49±45 mm s$^{-1}$ (mean±S.D.). The velocity trace displays several fast bursts, prolonged periods of slower swimming and periods of inactivity. For this trajectory, the characteristic fractal dimension (CFD) was 1.609, indicating that the trajectory was not straight (if straight, CFD=1). The Richardson dimension ($D_R$) was 1.002, which appeared to suggest minimal deviation from a straight line and therefore to be in conflict with the CFD.

As previously mentioned, the $D_R$ additionally incorporated sensitivity to the measurement scale while the CFD depended upon the duration of observation. The two measures can also diverge in the case of noisy data or data digitized over a small range of values. However, repeated analysis of individual trajectories indicated that the measurements were not compromised by noise or a limited range. The Lempel-Ziv complexity (LZC) of this trajectory was 242. Since the expectation for a purely random trajectory was approximately 700, this result therefore indicated that velocity did not vary randomly. The Hurst exponent (HE) was 0.938, indicating that the trajectory was highly persistent; in other words, its components were determined, or preserved, and thus the trajectory corresponded to uniform or consistent motion. Finally, the relative dispersion (R. Disp.) was 1.188. This value was close to the midrange of this measure and indicated that the mean value of the time series was relatively stable as a function of time.

Figure 18A:
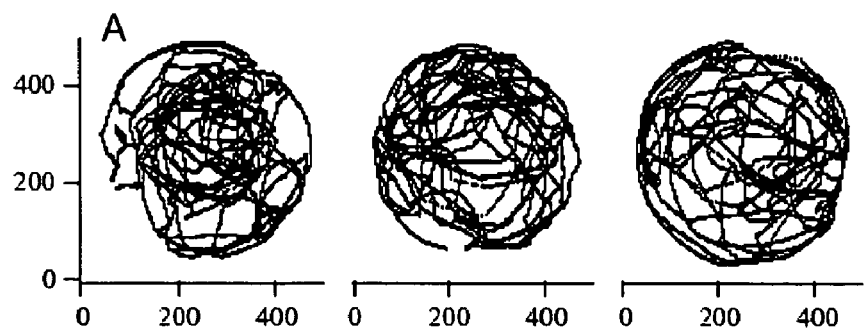
FIGS. 18a, 18b and 18c are graphic illustrations showing variability between swimming trajectories of fish, respectively, in the fourth example constructed in accordance with the teachings of the present invention.
Figure 18B:
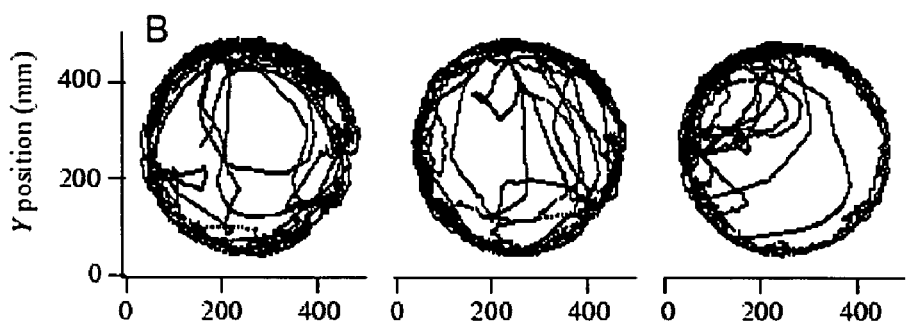
Figure 18C:
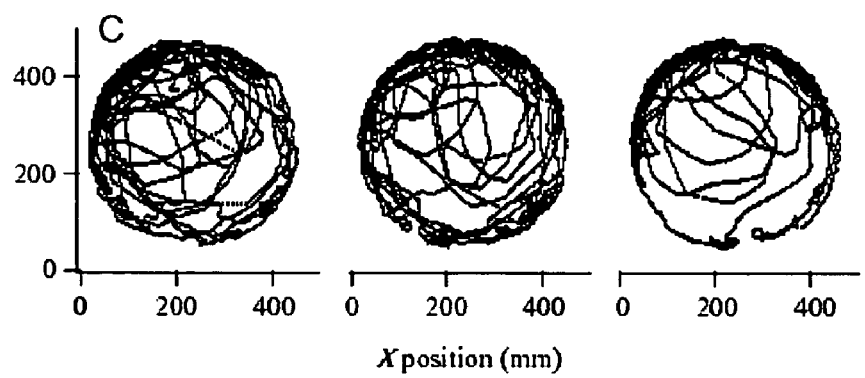

Swimming trajectories of different fish were dissimilar in appearance as shown in FIGS. 18a–18c which illustrate variability between swimming trajectories. FIG. 18a shows three consecutive 5-min recordings obtained from Fish 2 during its first visit to the tank. FIG. 18b shows three consecutive 5-min trajectories from Fish 5 recorded during its first visit to the tank. FIG. 18c shows three consecutive 5-min recordings from Fish 5 during its fifth visit to the tank. Differences between Fish 2 and Fish 5 are distinct. Visual comparison of FIG. 18b and FIG. 18c suggested the presence of a high degree of intra-individual variability, which was confirmed quantitatively with the nonlinear measures.

The distribution of path components in the centre versus the periphery of the tank seemed to be most variable. For example, the three consecutive 5-min trajectories of Fish 2, FIG. 18a, showed more time spent in the centre of the tank than did the three consecutive trajectories of Fish 5, FIG. 18b, which indicated relatively little time spent in the centre or traversing it. Instead, FIG. 18b, there was rather more accumulation of path components near the wall, sometimes forming dense patches, which were not seen in the trajectories of Fish 2, FIG. 18a. In addition, there was session-to-session variation in an individual fish's trajectories, as seen by comparing the first and fifth recording sessions of Fish 5, FIG. 18b and FIG. 18c. In the fifth session, there was a greater tendency to explore the centre than in the first session. This difference was reflected in a significant difference between the mean velocities of the two 15-min sessions (62.6 mm s$^{-1}$ VS58.8 mm s$^{-1}$; P<0.002). Also, there was greater variability between the three successive trajectories of the fifth session than between those in the first session; indeed, the third 5-min trajectory more closely represented those of the first session than the two trajectories preceding it, as it was denser at the periphery and exhibited a smaller number of excursions to the centre of the tank.

An initial overall impression of the nonlinear dynamical analysis was obtained by determining the range and variability of each measure determined across all five fish. These results are stated in Table 7. The coefficient of variation, CV=(S.D./mean)×100%, provided a quantitative characterization of the degree of spread in the observed dynamical measures. A high degree of variation was observed for some measures. The mean velocity had the highest CV (30.2%) and a nearly 10-fold range in values, and the CV of the LZC was also high (25.7%). By contrast, the CVs of the CFD, the $D_R$ and the R. Disp. were less than 7%. With the exception of $D_R$, the mean values of the nonlinear measures were all consistent with properties of a complex dynamical behavior.

TABLE 7

Measured Ranges Of Dynamical Measures

| Measure | Min. | Max. | Mean | S.D. | CV (%) |
|---|---|---|---|---|---|
| Mean velocity (mm · s−1) | 8.9 | 86.6 | 51.5 | 15.6 | 30.2 |
| CFD* | 1.24 | 1.79 | 1.62 | 0.10 | 6.2 |
| DR* | 1.00 | 1.11 | 1.03 | 0.03 | 2.4 |
| LZC | 91 | 379 | 235 | 60.42 | 25.7 |
| HE | 0.57 | 1.13 | 0.82 | 0.13 | 14.9 |
| R. Disp.* | 1.07 | 1.33 | 1.20 | 0.07 | 5.8 |

*Identifies measures with a coefficient of variation (CV) less then 10%.
CFD, characteristic fractal dimension;
DR, Richardson dimension;
LZC, Lempel-Ziv complexity;
HE, Hurst exponent;
R. Disp., relative dispersion.

The data summarized in Table 7 are displayed separately for each fish in Table 8. The latter results were obtained by averaging the values from all recording sessions (five per fish) and all trajectories (three for each recording session). Appreciably different values were obtained for each fish. Nevertheless, given the large S.D.s, the between-fish distributions overlap.

Mean velocity values were similar for Fish 2 and Fish 4 and for Fish 3 and Fish 5. This pattern was repeated for two of the nonlinear measures, CFD and $D_R$, but not for the other three. In general, there did not seem to be a consistent relationship between the mean values of different parameters and individual fish, suggesting that the measures, which, with the exception of mean velocity, were empirical, reflected different properties of the swimming trajectories.

TABLE 8

Mean Dynamical Measures For Each Fish

| Measure | Fish 1 | Fish 2 | Fish 3 | Fish 4 | Fish 5 |
|---|---|---|---|---|---|
| Velocity (mm · s−1) | 34.88 ± 13.72 | 49.49 ± 5.38 | 61.23 ± 17.02 | 49.85 ± 8.89 | 61.79 ± 13.23 |
| CFD | 1.51 ± 0.12 | 1.63 ± 0.03 | 1.67 ± 0.09 | 1.61 ± 0.05 | 1.70 ± 0.07 |

TABLE 8-continued

Mean Dynamical Measures For Each Fish

| Measure | Fish 1 | Fish 2 | Fish 3 | Fish 4 | Fish 5 |
|---|---|---|---|---|---|
| DR | 1.03 ± 0.02 | 1.02 ± 0.01 | 1.03 ± 0.02 | 1.01 ± 0.01 | 1.07 ± 0.02 |
| LZC | 213 ± 60 | 269 ± 41 | 197 ± 45 | 199 ± 23 | 279 ± 52 |
| HE | 0.96 ± 0.11 | 0.70 ± 0.07 | 0.86 ± 0.07 | 0.83 ± 0.07 | 0.74 ± 0.09 |
| R. Disp. | 1.14 ± 0.05 | 1.26 ± 0.051. | 16 ± 0.05 | 1.18 ± 0.06 | 1.24 ± 0.05 |

Values are means ± S.D.
CFD, characteristic fractal dimension;
DR, Richardson dimension;
LZC, Lempel-Ziv complexity;
HE, Hurst exponent;
R. Disp., relative dispersion.

Figure 19:
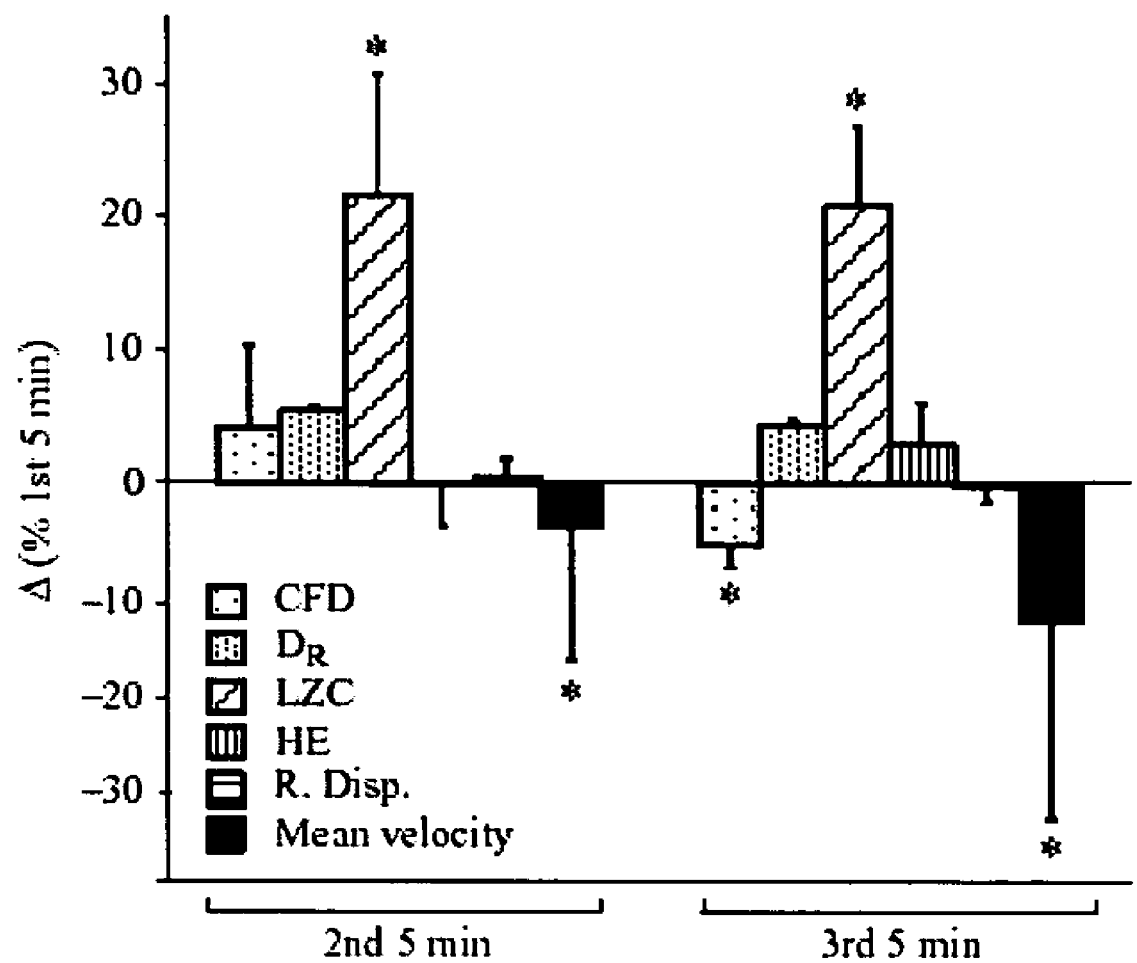
FIG. 19 is a graphic illustration showing time-dependent adaptation of swimming trajectories of fish in the fourth example constructed in accordance with the teachings of the present invention.

Three of the six measures had time-dependent changes during the 15-min recording periods. Mean velocity decreased by 77% from the first to the last 5-min recordings (from 58.41 mm s$^{-1}$ to 45.01 mm s$^{-1}$), and the mean CFD decreased by 5% from 1.62 to 1.54. By contrast, the average LZC increased by 15% from 214 to 248, while the other measures did not change appreciably. Since the data were pooled for multiple exposures of the five fish, a repeated-measures analysis of variance (ANOVA) was used to ask if there were significant changes in a given measure between the three subsequent 5-min epochs of a 15-min recording session. The results, shown in Table 9, indicated significant differences (P<0.015) between subsequent 5-min trajectories for mean velocity and CFD. Also, in the case of LZC, the first 5-min trajectory was significantly different from both the second and third ones. These time-dependent changes in the six measures relative to each other during a 15-min recording are illustrated in FIG. 19 which illustrates time-dependent adaptation. Values of the six measures averaged over all fish are displayed. Separate means were calculated for each trajectory of 5-min duration. The displayed values were normalized against the average value obtained during the first 5-min period. Asterisks identify statistically significant differences (P<0.015) compared with the first 5-min period.

TABLE 9

Statistical Comparison Of 5 Min Swimming Trajectories

| | 1st vs 3rd 5 min | | 1st vs 2nd 5 min | | 2nd vs 3rd 5 min | |
|---|---|---|---|---|---|---|
| Measure | t | P | t | P | t | P |
| Mean velocity (mm · s-1) | 5.20 | <0.0001* | 3.15 | 0.002* | 2.49 | 0.015* |
| CFD | 4.3 | 0.001* | 2.05 | 0.04* | 2.51 | 0.01* |
| DR | -1.18 | 0.240 | -1.70 | 0.09 | 0.30 | 0.767 |
| LZC | -2.83 | 0.006* | -2.47 | 0.0162* | -5.3 | 0.599 |
| HE | -0.18 | 0.857 | 0.78 | 0.435 | 0.98 | 0.332 |
| R. Disp. | 0.34 | 0.732 | -0.24 | 0.81 | 0.60 | 0.548 |

Repeated-measures ANOVA for significant testing across the five min periods
(*P < 0.015); d.f. = 68;
CFD, characteristic fractal dimension;
DR, Richardson dimension;
LZC, Lempel-Ziv complexity;
HE, Hurst exponent;
R. Disp., relative dispersion.

The repeated-measures ANOVA was also used to ask if there were differences between the five subsequent sessions in which data were collected from each fish, and the results were negative. Since the changes that occurred within a 15-min recording session were minimal, the discriminant analysis did not treat successive 5-min trajectories separately.

Three questions were addressed in the discriminant analysis: (1) based on the application of these six dynamical measures, would it be possible to conclude that the five fish are different; (2) given a trajectory and its dynamical characterization, would it be possible to correctly determine which fish produced the trajectory and (3) of the six measures used, which ones were the most effective in discriminating between different fish?

These questions were addressed by performing a discriminant analysis based on the six measures, with each fish providing a total of 15 trajectories. For this analysis, no distinction was made between first, second and third 5-min trajectories. Using these measures, we calculated $P_{SAME}$ (Fish A, Fish B), which was the probability that the six-dimensional measurement distributions corresponding to Fish A and Fish B were drawn from the same parent distribution. The results from the 10 possible pairwise discriminations are shown in Table 10. As an example from that table, it is seen that $P_{SAME}(1, 2) = 0.19 \times 10^{-5}$; that is, the probability that Fish 1 and Fish 2 trajectories were produced by the same fish is $0.19 \times 10^{-5}$. Accordingly, Fish 1 and Fish 2 had very different dynamical profiles.

TABLE 10

$P_{SAME}$, The Probability That Two Fish Are The Same

| Fish | 1 | 2 | 3 | 4 | 5 |
|---|---|---|---|---|---|
| 1 | | 0.19 × 10$^{-5}$ | 0.61 × 10$^{-2}$ | 0.19 × 10$^{-4}$ | 0.38 × 10$^{-4}$ |
| 2 | | | 0.15 × 10$^{-7}$ | 0.71 × 10$^{-9}$ | 0.36 × 10$^{-6}$ |
| 3 | | | | 0.90 × 10$^{-2}$ | 0.70 × 10$^{-6}$ |
| 4 | | | | | 0.81 × 10$^{-7}$ |
| 5 | | | | | |

$P_{SAME}$ is calculated with the between-group Mahalanobis distance.

The error rate also can be determined empirically by performing a classification. The results of an out-of-sample classification are shown in Table 11 for both minimum Mahalanobis distance and maximum Bayesian likelihood criteria, respectively.

TABLE 11

Classification Results Obtained With Fish Trajectories

| Fish | Assigned classification (frequency) | | | | |
|---|---|---|---|---|---|
| | 1 | 2 | 3 | 4 | 5 |
| 1 | 13/12 | 0/0 | 0/0 | 0/0 | 2/3 |
| 2 | 3/2 | 11/12 | 0/0 | 0/0 | 1/1 |
| 3 | 5/3 | 0/0 | 8/8 | 0/2 | 2/2 |
| 4 | 2/1 | 1/1 | 7/2 | 5/11 | 0/0 |
| 5 | 1/1 | 0/0 | 3/3 | 0/0 | 11/11 |

Trajectories of individual fish were classified using two criteria (minimum Mahalanobis distance/maximum Bayesian likelihood).
The source of the trajectory is listed to the left, and its assigned classification is on the upper row.
The identity line is in bold.

For example, the entry 13/12 in the Fish 1-Fish 1 box means that 13 out of 15 Fish 1 trajectories were classified as Fish 1 using the minimum distance criterion and 12 were correctly classified as Fish 1 using the maximum likelihood crieterion. The entry 2/3 in the Fish 1-Fish 5 box means that two Fish 1 trajectories were classified as Fish 5 using minimum distance and three Fish 1 trajectories were classified as Fish 5 using maximum likelihood as the criterion. Thus, more than 75% of the trajectories from Fish 1, 2 and 5 were correctly classified with both criteria. Also, a comparison based on mean velocity alone suggests similarities between Fish 1 and 4 and between Fish 3 and 5; the discriminant analysis, which uses six measures, does not often confuse these fish.

The expectation error rate is the error rate that would be observed if the classifications were performed randomly. There are five fish. If trajectories were assigned randomly, four out of five trajectories would be misclassified. This gives an expectation error rate of 80%. For these data, the overall error rate using minimum Mahalanobis distance as the classification criterion was 36%. The overall error rate using the maximum Bayesian likelihood was 28%.

The third question addressed with discrimination analysis asked, 'of the measures used, which were the most effective in discriminating between different fish?' This question is not easily answered when there were five groups (five fish) as opposed to only two. In the case of a pairwise, two group comparison, a measure's coefficient of determination establishes the amount of total between-group variance that can be accounted for by the measure. Then, the larger a measure's coefficient of determination, the more effective it is in discriminating between groups. A large coefficient of determination corresponds to a large between group Mahalanobis distance (specifically, the partial derivative of the coefficient of determination with respect to the Mahalanobis distance is positive).

The effectiveness of the six measures in the 10 pairwise between-group discriminations was assessed empirically. Table 12 gives the rank ordering of the coefficients of determination for each measure for each pairwise discrimination (ordered from the largest to the smallest). For example, when Fish 1 and Fish 2 are compared, the HE is most effective in discriminating between the two groups while the $D_R$ is the least effective. When the rank ordering of the 10 pairwise discriminations is compared, none of the measures stands out as being exceptionally effective. However, if the rank order is treated as a score for each pair, the data indicated that the $D_R$ and the HE have the lowest cumulative scores, suggesting they are the most effective.

Interestingly, the mean values of these two measures (Table 7) were consistent with trajectories that were relatively stable or determined (i.e. mean of HE=0.82 indicates a high degree of persistence and mean $D_R$=1.06 indicated high similarity to a straight line trajectory). The lack of a consistent pattern in the results presented in Table 12 was not surprising, since the results established that the fish trajectories are highly individualistic (Table 10) using a statistic, P SAME, that combines all six measures.

TABLE 12

Rank Ordering Of The Coefficients Of Determination

| Compared fish | 1st | 2nd | 3rd | 4th | 5th | 6th |
|---|---|---|---|---|---|---|
| Fish 1 vs Fish 2 | HE | R. Disp. | V' | CFD | LZC | $D_R$ |
| Fish 1 vs Fish 3 | V' | CFD | HE | R. Disp. | LZC | $D_R$ |
| Fish 1 vs Fish 4 | HE | V' | $D_R$ | CFD | R. Disp. | LZC |
| Fish 1 vs Fish 5 | $D_R$ | HE | R. Disp. | V' | CFD | LZC |
| Fish 2 vs Fish 3 | HE | R. Disp. | LZC | V' | CFD | $D_R$ |
| Fish 2 vs Fish 4 | LZC | $D_R$ | HE | R. Disp. | CFD | V' |
| Fish 2 vs Fish 5 | $D_R$ | V' | CFD | LZC | HE | R. Disp. |
| Fish 3 vs Fish 4 | $D_R$ | V' | CFD | HE | R. Disp. | LZC |
| Fish 3 vs Fish 5 | LZC | $D_R$ | R. Disp. | HE | CFD | V' |
| Fish 4 vs Fish 5 | $D_R$ | LZC | CFD | R. Disp. | HE | V' |

V' = mean velocity.

Another approach for obtaining an estimate of the comparative effectiveness of each dynamical measure was to calculate each measure's average coefficient of determination, taking the average over the 10 pairwise discriminations. These average values are shown in Table 13 and again suggest that $D_R$ and the HE are the most effective measures when used alone.

The results demonstrated that a set of nonlinear measures can be used in a discriminant analysis, or classification system, to distinguish between swimming trajectories of individual fish. That is, any two trajectories generated from different fish are distinguishable with a high confidence level. This discrimination was possible when nonlinear measures, along with the linear measure mean velocity, were applied collectively, as no single measure had a high coefficient of determination. The results also showed that the nonlinear measures used provide a perspective on a basic behavior, swimming in a sparse environment, that complements insights obtained with more classical kinematic measures. In general, the values for the different measures suggested that swimming is not purely random but is rather complex, with detectable redundancy.

TABLE 13

Mean Coefficient Of Determination

| Measure | Mean coefficient of determination |
|---|---|
| Mean Velocity (mm · s−1) | 0.247 |
| Characteristic Fractal Dimension (CFD) | 0.233 |
| Richardson Dimension (DR) | 0.382 |
| Lempel-Ziv Complexity (LZC) | 0.287 |
| Hurst Exponent (HE) | 0.351 |
| Relative Dispersion (R. Disp.) | 0.298 |

The five nonlinear measures applied in this example were empirical measures of complexity of swimming behavior, and each reduced a trajectory into a single value. With the exception of the Richardson dimension, the values of these nonlinear measures were consistent with the notion that goldfish swimming in even a relatively sparse environment is a mixture of random and nonlinear deterministic activities. Their empirical nature may explain the finding that two of the measures, the characteristic fractal dimension and Richardson dimension, which are expected to reflect similar properties, often diverged. Accordingly, the nonlinear measures and discriminant analysis employed in this example can be applied to detect subtle changes in behavioral sequences altered by changes in the environment. In this example, a relatively small but significant decrease during the 15-min period was not only detected in mean velocity but also in CFD and Lempel-Ziv complexity. The results in the CFD were consistent with reports that fractal dimension decreases in conditions characterized as stressful.

In this example, a discriminant analysis based on six measures was used to characterize between-group differences and to classify individuals amongst the groups, with each fish defining its own group. Five fish were used and five recordings consisting of three consecutive 5-min trajectories were obtained from each fish. Thus, in the language of discriminant analysis, there were five groups, 15 elements in each group and six-dimensional measure space. Addressed were a sequence of three questions. First, it was asked if we were able to conclude that the fish are different, computing $P_{SAME}$ for each pair of fish. Although direct visual observation of the fish did not suggest that their swimming behavior was dramatically different, the calculations of $P_{SAME}$ indicate that trajectories are highly individual, and each fish has a very different swimming profile. Then the problem of classification of individual 5-min trajectories among the five possible groups was addressed by calculating $P_{ERROR}$ for each pairwise classification. As expected, $P_{ERROR}$ was larger than $P_{SAME}$, with an average value of 5.7%. However, $P_{ERROR}$ was a theoretical estimate of the error in a pairwise classification based on the between-group Mahalanobis distance. An empirical test of this classification was produced by computing an out-of-sample classification that used the minimum individual-to-group Mahalanobis distance as the classification criterion. It gave an error rate of 36%, in contrast to the expected error rate obtained with random assignment of 80%. The error rate using maximum Bayesian likelihood as the assignment criterion was even less, 28%. It might seem surprising that, while the average $P_{ERROR}$ was 5.7%, the empirically determined classification error rate was greater. Yet, $P_{ERROR}$ was the predicted error rate in a single pairwise classification. The empirically determined error rate was more appropriately compared against a classification procedure based on a sequence of pairwise classifications in which several individual pairwise errors accumulated to produce the overall result. When the distinction between pairwise and global error was taken into account, it was seen that the error rates were similar.

The third question concerned the identification of the measure or measures that were most successful in discriminating between fish. This was investigated by calculating the coefficient of determination in each pairwise classification for each measure. The results indicated that no single measure emerged as the most effective. However, it was possible to conclude that the nonlinear measures were more effective than the mean velocity, with the most effective being the HE and $D_R$, values which were consistent with the general conclusion that fish swimming in a sparse environment have a relatively low degree of complexity.

Although the invention was described above in connection with specific examples, they are not limiting as to the scope and applicability of the invention to classification systems in general. Other modifications and variations of the systems and methods described will be apparent to those skilled in the art.

What is claimed is:

1. A method for performing a categorical analysis on one or more time dependent dynamic processes, the method comprising:
    capturing a time series associated with a selected type of dynamic process;
    based on the selected type of dynamic process, selecting a reference library of data of different quantifiable dynamic characteristics of reference time series, wherein the data is segmented into at least one classification of groups where each classification's segmentation into groups represents a correlation of quantified dynamic data of a predefined set of a plurality of quantifiable dynamic classification characteristics from among the different quantifiable dynamic characteristics;
    processing quantified dynamic data of the captured time series for the predefined set of quantifiable dynamic classification characteristics of a selected classification of groups within the reference library; and
    classifying the captured time series with respect to the groups of the selected classification based on the processed quantified dynamic data of the captured time series.

2. The method of claim 1 where the time series are bio-metric signals and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processing of quantified dynamic data of the captured time series is done for the first set of quantifiable dynamic classification characteristics of the first classification of groups within the reference library and the classifying of the captured time series with respect to the groups of the first classification.

3. The method of claim 2 where a second set of quantifiable dynamic classification characteristics for a second classification of groups includes at least two characteristics from the group consisting of fractal dimension, Richardson dimension, Lempel-Ziv complexity, Hurst exponent and relative dispersion wherein the processing of quantified dynamic data of the captured time series is also done for the second set of quantifiable dynamic classification characteristics of the second classification of groups within the reference library and the classifying of the captured time series is also done with respect to the groups of the second classification.

4. The method of claim 2 wherein:
    the classifying of the captured time series with respect to the groups of the selected classification based on the processed quantified dynamic data of the captured time series includes calculating the probability of the processed quantified dynamic data of the captured time series is a member of each group of the first classification and classifying the captured time series in the group for which a highest probability of membership is calculated.

5. The method of claim 4 wherein the calculating of the probability of the processed quantified dynamic data of the captured time series is a member of each group of the selected classification includes calculating probabilities using at least one criteria from the group consisting of minimum Mahalanobis distance or maximum Bayesian likelihood.

6. The method of claim 1 where a first set of quantifiable dynamic classification characteristics for a first classification of groups includes at least two characteristics from the group consisting of fractal dimension, Richardson dimension, Lempel-Ziv complexity, Hurst exponent and relative dispersion wherein the processing of quantified dynamic data of the captured time series is done for the first set of quantifiable dynamic classification characteristics of the first classification of groups within the reference library and the classifying of the captured time series with respect to the groups of the first classification.

7. The method of claim 1 wherein a first set of quantifiable dynamic classification characteristics for a first classification of groups includes fractal dimension, Richardson dimension, Lempel-Ziv complexity, Hurst exponent and relative dispersion wherein the processing of quantified dynamic data of the captured time series is done for the first set of quantifiable dynamic classification characteristics of the first classification of groups within the reference library and the classifying of the captured time series with respect to the groups of the first classification.

8. The method of claim 1 wherein the classifying of the captured time series with respect to the groups of the selected classification based on the processed quantified dynamic data of the captured time series includes calculating the probability of the processed quantified dynamic data of the captured time series is a member of each group of the selected classification and classifying the captured time series in the group for which a highest probability of membership is calculated.

9. The method of claim 1 wherein the calculating of the probability of the processed quantified dynamic data of the captured time series is a member of each group of the selected classification includes calculating probabilities using at least one criteria from the group consisting of minimum Mahalanobis distance or maximum Bayesian likelihood.

10. The method of claim 1 wherein the classifying of the captured time series with respect to the groups of the selected classification based on the processed quantified dynamic data of the captured time series includes calculating the probability of the processed quantified dynamic data of the captured time series is a member of each group of the selected classification and classifying the captured time series as a member of each group for which a calculated probability of membership exceeds a membership threshold.

11. The method of claim 1 wherein the classifying of the captured time series with respect to the groups of the selected classification based on the processed quantified dynamic data of the captured time series includes calculating the probability of the processed quantified dynamic data of the captured time series is a member of each group of the selected classification and classifying the captured time series as not a member of each group for which a calculated probability of membership does not exceed a membership threshold.

12. The method of claim 1 where the dynamic process is locomotive behavior and the time series are movement trajectories and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processing of quantified dynamic data of the captured time series is done for the first set of quantifiable dynamic classification characteristics of the first classification of groups within the reference library and the classifying of the captured time series with respect to the groups of the first classification.

13. The method of claim 1 where the dynamic process is brain wave activity and the time series are electroencephalograms (EEGs) and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processing of quantified dynamic data of the captured time series is done for the first set of quantifiable dynamic classification characteristics of the first classification of groups within the reference library and the classifying of the captured time series with respect to the groups of the first classification.

14. The method of claim 1 where the dynamic process is heart activity and the time series are electrocardiograms (ECGs) and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processing of quantified dynamic data of the captured time series is done for the first set of quantifiable dynamic classification characteristics of the first classification of groups within the reference library and the classifying of the captured time series with respect to the groups of the first classification.

15. A system for categorical analysis of time dependent dynamic processes, the system comprising:
 a processor having an input for receiving data of quantified dynamic characteristics of a captured time series associated with a selected type of dynamic process;
 a memory unit coupled with the processor;
 the memory unit including a reference library of data of different quantifiable dynamic characteristics of reference time series associated with the selected type of dynamic process wherein the data is segmented into at least one classification of groups where each classification's segmentation into groups represents a correlation of quantified dynamic data of a predefined set of a plurality of quantifiable dynamic classification characteristics from among the different quantifiable dynamic characteristics; and
 the processor being configured to process quantified dynamic characteristic data of the captured time series for the set of classification characteristics of a selected classification of groups within the reference library to classify the captured time series with respect to the groups of the selected classification based on the processed quantified dynamic characteristic data.

16. The system of claim 15 where the time series are bio-metric signals and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processor is configured to process quantified dynamic data of the captured time series for the first set of quantifiable dynamic classification characteristics of the first classification of groups within the reference library to classify the captured time series with respect to the groups of the first classification by calculating the probability of the processed quantified dynamic data of the captured time series is a member of each group of the first classification and classifying the captured time series in the group for which a highest probability of membership is calculated.

17. The system of claim 16 wherein the processor is configured to calculate the probability of the processed quantified dynamic data of the captured time series is a member of each group of the selected classification by using at least one criteria from the group consisting of minimum Mahalanobis distance or maximum Bayesian likelihood.

18. The system of claim 15 where the dynamic process is locomotive behavior, the time series are movement trajectories and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processor is configured to process quantified dynamic data of the captured time series for the first set of quantifiable dynamic classification characteristics of the first classification of groups within the reference library to classify the captured time series with respect to the groups of the first classification.

19. The system of claim 15 where the dynamic process is brain wave activity, the time series are electroencephalograms (EEGs) and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processor is configured to process quantified dynamic data of the captured time series for the first set of quantifiable dynamic classification characteristics of the first classification of groups within the reference library to classify the captured time series with respect to the groups of the first classification.

20. The system of claim 15 where the dynamic process is heart activity, the time series are electrocardiograms (ECGs) and a first set of quantifiable dynamic classification characteristics for a first classification of groups includes at least one characteristic from the group consisting of fractal dimension, Richardson dimension, Lempel-Ziv complexity, Hurst exponent and relative dispersion wherein the processor is configured to process quantified dynamic data of the captured time series for the first set of quantifiable dynamic classification characteristics of the first classification of groups within the reference library to classify the captured time series with respect to the groups of the first classification.

21. A method for creating a reference library of data for use in performing categorical analysis of time dependent dynamic processes, the method comprising:
  capturing reference time series associated with a selected type of dynamic process;
  deriving data of selected quantifiable dynamic characteristics for each reference time series; and
  segmenting the data into at least one classification of groups where each classification's segmentation into groups represents a correlation of data of a predefined set of quantified dynamic classification characteristics from among the selected quantified dynamic characteristics whereby a subject captured time series of the selected type of dynamic process can be classified into a group of the selected classification based on correlating quantified dynamic data derived from the subject captured time series corresponding to the predefined set of quantified dynamic classification characteristics of the selected classification of groups.

22. The method of claim 21 further comprising defining a first set of quantifiable dynamic classification characteristics for a first classification of groups by:
  deriving data for at least three quantifiable dynamic characteristics for at least a selected minimum number of reference time series from each group of the first classification of groups;
  calculating effectiveness with respect to each quantifiable dynamic characteristic based on the respective data derived for the reference time series of each respective group; and
  selecting at least two quantifiable dynamic characteristics that have the highest calculated effectiveness for inclusion in the first set of quantifiable dynamic classification characteristics for the first classification of groups.

23. The method of claim 22 where the time series are bio-metric signals and wherein data is derived for at least one quantifiable dynamic characteristic from the group consisting of fractal dimension, Richardson dimension, Lempel-Ziv complexity, Hurst exponent and relative dispersion.

24. The method of claim 22 wherein data is derived for quantifiable dynamic characteristics including fractal dimension, Richardson dimension, Lempel-Ziv complexity, Hurst exponent and relative dispersion.

25. The method of claim 22 further comprising defining a second set of quantifiable dynamic classification characteristics for a second classification of groups by:
  deriving data for at least three quantifiable dynamic characteristics for at least a selected minimum number of reference time series from each group of the second classification of groups;
  calculating effectiveness with respect to each quantifiable dynamic characteristic based on the respective data derived for the reference time series of each respective group of the second classification of groups; and
  selecting at least two quantifiable dynamic characteristics that have highest calculated effectiveness for inclusion in the second set of quantifiable dynamic classification characteristics for the second classification of groups.

26. The method of claim 25 where the time series are bio-metric signals and wherein data is derived for defining the first set of quantifiable dynamic classification characteristics is also used for defining the second set of quantifiable dynamic classification characteristics where a first reference time series is included in a group of the first classification of groups and also a group of the second classification of groups.

27. The method of claim 26 wherein data is derived for at least one quantifiable dynamic characteristic from the group consisting of fractal dimension, Richardson dimension, Lempel-Ziv complexity, Hurst exponent and relative dispersion.

28. The method of claim 26 wherein data is derived for quantifiable dynamic characteristics including fractal dimension, Richardson dimension, Lempel-Ziv complexity, Hurst exponent and relative dispersion.

29. The method of claim 22 where the dynamic process is locomotive behavior and the time series are movement trajectories and wherein data is derived for at least one quantifiable dynamic characteristic from the group consisting of fractal dimension, Richardson dimension, Lempel-Ziv complexity, Hurst exponent and relative dispersion.

30. The method of claim 22 where the dynamic process is brain wave activity and the time series are electroencephalograms (EEGs) and wherein data is derived for at least one quantifiable dynamic characteristic from the group consisting of fractal dimension, Richardson dimension, Lempel-Ziv complexity, Hurst exponent and relative dispersion.

31. The method of claim 22 where the dynamic process is heart activity and the time series are electrocardiograms (ECGs) and wherein data is derived for at least one quantifiable dynamic characteristic from the group consisting of fractal dimension, Richardson dimension, Lempel-Ziv complexity, Hurst exponent and relative dispersion.

32. The method of claim 22 wherein the calculating effectiveness with respect to each quantifiable dynamic characteristic based on the respective data derived for the reference time series of each respective group includes calculating partial F-values with respect to each quantifiable dynamic characteristic based on the respective data derived for the reference time series of each respective group.

* * * * *